United States Patent
Jaffrey et al.

(10) Patent No.: US 11,021,703 B2
(45) Date of Patent: Jun. 1, 2021

(54) METHODS AND KIT FOR CHARACTERIZING THE MODIFIED BASE STATUS OF A TRANSCRIPTOME

(71) Applicant: CORNELL UNIVERSITY, Ithaca, NY (US)

(72) Inventors: Samie R. Jaffrey, New York, NY (US); Kate D. Meyer, New York, NY (US); Christopher E. Mason, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/377,680

(22) PCT Filed: Feb. 18, 2013

(86) PCT No.: PCT/US2013/026593
§ 371 (c)(1),
(2) Date: Aug. 8, 2014

(87) PCT Pub. No.: WO2013/123481
PCT Pub. Date: Aug. 22, 2013

(65) Prior Publication Data
US 2016/0060622 A1   Mar. 3, 2016

Related U.S. Application Data

(60) Provisional application No. 61/599,714, filed on Feb. 16, 2012.

(51) Int. Cl.
*C12Q 1/6804* (2018.01)
*C12N 15/10* (2006.01)

(52) U.S. Cl.
CPC ....... *C12N 15/1093* (2013.01); *C12Q 1/6804* (2013.01)

(58) Field of Classification Search
CPC ............ C12Q 1/6804; C12Q 2600/106; C12Q 1/6806; C12N 15/1093
See application file for complete search history.

(56) References Cited

U.S. PATENT DOCUMENTS

| 6,114,114 A | 9/2000 | Seilhamer et al. |
| 6,610,504 B1 * | 8/2003 | Yuan ........................ C12Q 1/34 435/15 |
| 7,906,288 B2 | 3/2011 | Nelson et al. |
| 2005/0153316 A1 | 7/2005 | Jeddeloh et al. |
| 2005/0272070 A1 | 12/2005 | Enrich et al. |
| 2007/0042365 A1 | 2/2007 | Millar et al. |
| 2007/0178506 A1 | 8/2007 | Martienssen et al. |
| 2009/0176655 A1 | 7/2009 | Esteller |
| 2009/0270482 A1 | 10/2009 | Schuebeler et al. |
| 2010/0092951 A1 | 4/2010 | Tetzner et al. |
| 2012/0208193 A1 | 8/2012 | Okino et al. |
| 2012/0219949 A1 | 8/2012 | Sakai et al. |
| 2012/0288509 A1 | 11/2012 | Schuebeler et al. |

FOREIGN PATENT DOCUMENTS

| EP | 1761639 B1 | 1/2013 |
| WO | 2012143481 A2 | 10/2012 |

OTHER PUBLICATIONS

Bodi et al. Yeast targets for mRNA methylation. Nucleic Acids Research, vol. 38, No. 16, pp. 5327-5335, Apr. 26, 2010, including Supplementary Data, printed as pp. 1/7-7/7.*
Tenenbaum et al. Identifying mRNA subsets in messenger ribonucleoprotein complexes by using cDNA arrays. Proceedings of the National Academy of Sciences, USA, vol. 97, No. 26, pp. 14085-14090, Dec. 2000.*
Talla et al. A novel design of whole-genome microarray probes for *Saccharomyces cerevisiae* which minimizes cross-hybridization. BMC Genomics, vol. 4, p. 38, Sep. 2003.*
Sephton et al. Identification of neuronal RNA targets of TDP-43-containing ribonucleoprotein complexes. The Journal of Biological Chemistry, vol. 286, No. 2, pp. 1204-1215, Jan. 14, 2011, including pp. 1/43-43/43 of Supplemental Data.*
Keene et al. RIP-Chip: the isolation and identification of mRNAs, microRNAs and protein components of ribonucleoprotein complexes from cell extracts. Nature Protocols, vol. 1, No. 1, pp. 302-307, 2006.*
Bokar, JA. The biosynthesis and functional roles of methylated nucleosides in eukaryotic mRNA. Topics in Current Genetics, vol. 12, pp. 141-177, Jan. 7, 2005.*
Squires et al. Widespread occurrence of 5-methylcytosine in human coding and non-coding RNA. Nucleic Acids Research, vol. 40, No. 11, pp. 5023-5033, Feb. 16, 2012. (Year: 2012).*
Supplementary Information for Jia et al. N6-methyladenosine in nuclear RNA is a major substrate of the obesity-associated FTO. Nature Chemical Biology, vol. 7, pp. 885-887, 2012, published online Oct. 2011, pp. S1-S26. (Year: 2011).*

(Continued)

*Primary Examiner* — Jennifer Dunston
(74) *Attorney, Agent, or Firm* — Troutman Pepper Hamilton Sanders LLP (Rochester)

(57) ABSTRACT

This invention relates to a method of characterizing the modified base status of a transcriptome, which involves contacting a transcriptome comprising one or more modified bases with an antibody specific to the modified bases under conditions effective to bind the antibody to the modified bases; isolating, from the transcriptome, a pool of RNA transcripts to which the antibody binds; and identifying isolated RNA transcripts that are present in a higher abundance in the isolated pool relative to the transcriptome, where each of the isolated RNA transcripts that are present in a higher abundance in the isolated pool together characterize the modified base status of the transcriptome. Also disclosed are a method of diagnosis or prognosis of a disease, a method of determining the effect of a treatment on modified base levels in RNA, and a kit for characterizing the modified base status of a transcriptome.

19 Claims, 20 Drawing Sheets

Specification includes a Sequence Listing.

(56) References Cited

OTHER PUBLICATIONS

Motorin et al. 5-methylcytosine in RNA: detection, enzymatic formation and biological functions. Nucleic Acids Research, vol. 38, No. 5, pp. 1415-1430, 2010, published online Dec. 8, 2009. (Year: 2009).*
Hershfield et al. Cancer Research, vol. vol. 43, pp. 3451-3458, Jul. 1983. (Year: 1893).*
Tseng et al. Specific inhibition of transfer RNA methylation and modification in tissues of mice treated with 5-fluorocuracil. Cancer Research, vol. 38, pp. 1250-1257, May 1978. (Year: 1978).*
Supplemental Information for Myer, KD., Salestore, Y., Zumbo, P., Elemento, O., Mason, CE., and Jaffrey, SR. Cell, vol. 149, pp. 1635-1646, Jun. 22, 2012, EPub May 17, 2012, pp. S1-S15. (Year: 2012).*
Dominissini et al. Topology of hte human and mouse mA6A RNA methylomes revealed by m6A-seq. Nature, vol. 485, pp. 201-206, pp. 1/2-2/2 of Online Methods, and pp. 1-22-22/22 of Supplementary Information, May 2012, published online Apr. 29, 2012. (Year: 2012).*
Haukanes et al. Application of magnetic beads in bioassays. Nature Biotechnology, vol. 11, pp. 60-63, Jan. 1993. (Year: 1993).*
Chi et al. Agronaute HITS-CLIP decodes microRNA-mRNA interaction maps. Nature, vol. 460, pp. 479-486, Jul. 2009. (Year: 2009).*
Chen et al., "Development of Cell-Active N6-Methyladenosine RNA Demethylase FTO Inhibitor," J. Am. Chem. Soc. 134:17963-17971 (2012).
Cole et al., "Specific Regulation of mRNA Cap Methylation by the c-Myc and E2F1 Transcription Factors," Oncogene 28(9):1169-1175 (2009).

Dominissini et al., "Transcriptome-wide Mapping of N6-methyladenosine by m6A-seq based on Immunocapturing and Massively Parallel Sequencing," Nature Protocols 8(1):176-189 (2013).
Horowitz et al., "Mapping of N6-methyladenosine Residues in Bovine Prolactin mRNA," Proc. Natl. Acad. Sci. USA 81:5667-5671 (1984).
Jia et al., "N6-Methyladenosine in Nuclear RNA is a Major Substrate of the Obesity-Associated FTO," Nat Chem Biol. 7(12):885-887 (2012).
Kellner et al., "Detection of RNA Modifications," RNA Biology 7(2):237-247 (2010).
Meyer et al., "Comprehensive Analysis of mRNA Methylation Reveals Enrichment in 3' UTRs and near Stop Codons," Cell 149(7):1635-1646 (2012).
Munns et al., "Immunospecific Retention of Oligonucleotides Possessing N6-Methyladenosine and 7-Methylguanosine," The Journal of Biological Chemistry 252(9):3102-3104 (1977).
Saletore et al., "The Birth of the Epitranscriptome: Deciphering the Function of RNA Modifications," Genome Biology 13(175):1-11 (2012).
Van Vliet, "Next Generation Sequencing of Microbial Transcriptomes: Challenges and Opportunities," FEMS Microbiol Lett 302:1-7 (2010).
Xiao et al., "DamIP: A Novel Method to Identify DNA Binding Sites in vivo," NRS 8:1-6 (2010).
Zheng et al., "ALKBH5 Is a Mammalian RNA Demethylase that Impacts RNA Metabolism and Mouse Fertility," Molecular Cell 49:1-12 (2013).
International Search Report and Written Opinion for corresponding application No. PCT/US13/26593 (dated May 13, 2013).

* cited by examiner

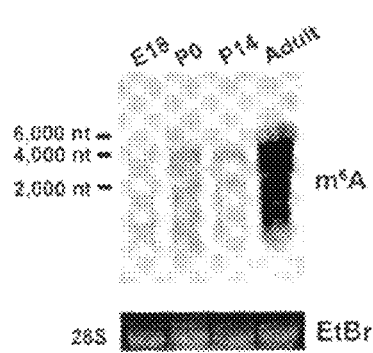
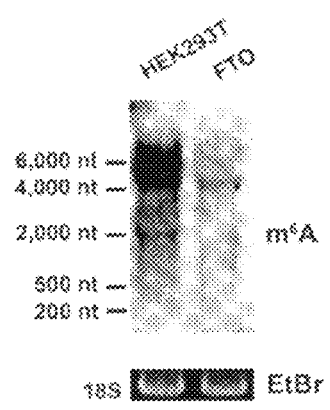
FIG. 3A
FIG. 3B

FIG. 6B
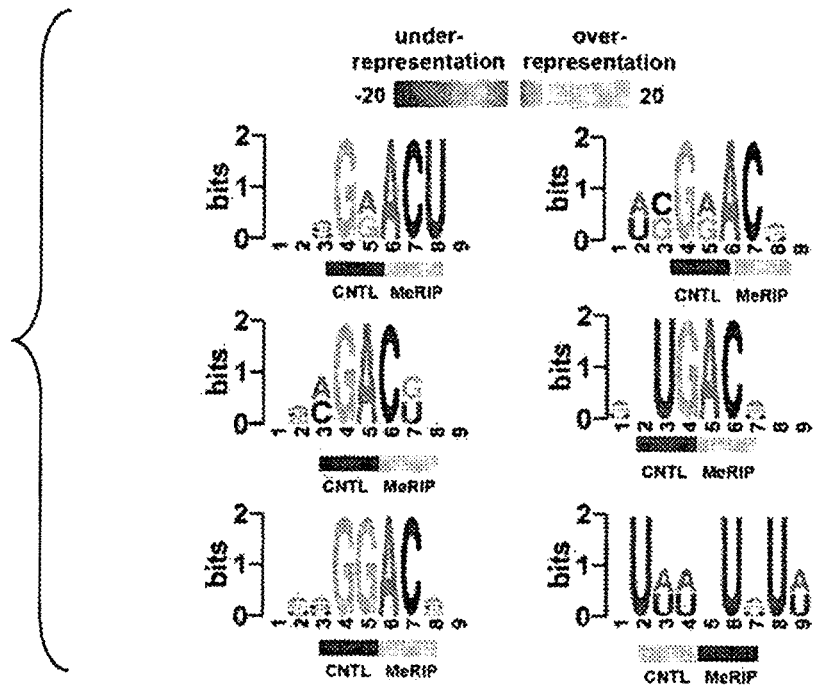
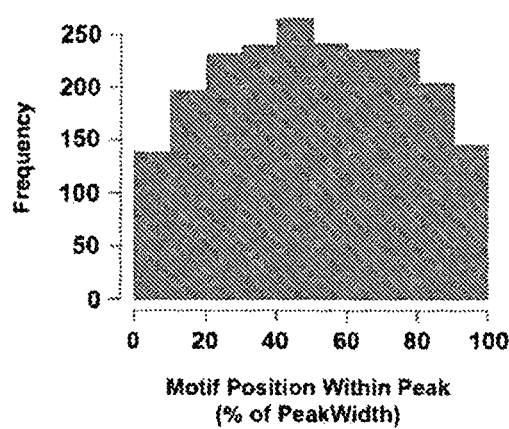
FIG. 6C

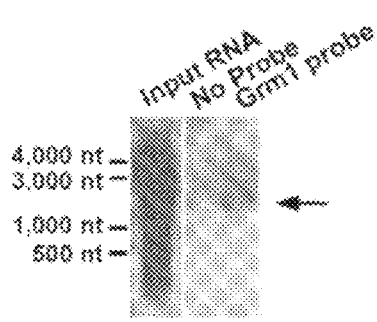
FIG. 7B
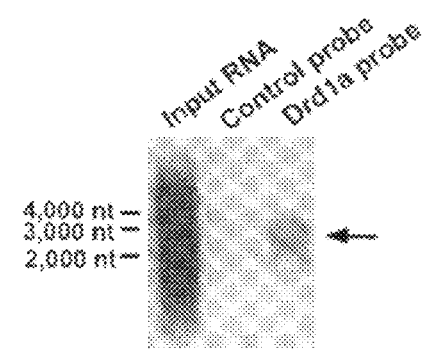
FIG. 7D
FIG. 7C
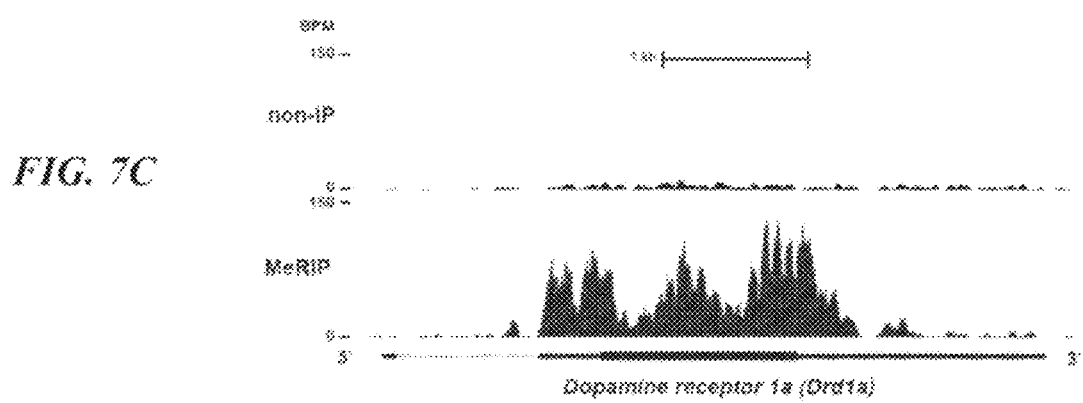

METHODS AND KIT FOR CHARACTERIZING THE MODIFIED BASE STATUS OF A TRANSCRIPTOME

This application is a national stage application under 35 U.S.C. § 371 of PCT Application No. PCT/US2013/026593, filed Feb. 18, 2013, which claims the priority benefit of U.S. Provisional Patent Application Ser. No. 61/599,714, filed Feb. 16, 2012 which is hereby incorporated by reference in its entirety.

This invention was made with government support under MH080420 awarded by the National Institutes of Health. The government has certain rights in the invention.

FIELD OF THE INVENTION

This invention relates to methods and a kit for characterizing the modified base status of a transcriptome.

BACKGROUND OF THE INVENTION

The distribution of modified bases in RNA is poorly understood. For example, previous studies have found that the base modification of $N^6$-methyladenosine ("$m^6A$") exists in RNA in a variety of organisms, including viruses, yeast, and mammals (Beemon et al., "Localization of N6-Methyladenosine in the Rous Sarcoma Virus Genome," *J. Mol. Biol.* 113:165-179 (1977); Bodi et al., "Yeast Targets for mRNA Methylation," *Nucleic Acids Res.* 38:5327-5335 (2010)). Moreover, $m^6A$ is found in tRNA (Saneyoshi et al., "Isolation and Characterization of N6-Methyladenosine from *Escherichia coli* Valine Transfer RNA," *Biochim. Biophys. Acta.* 190:264-273 (1969)), rRNA (Iwanami et al., "Methylated Bases of Ribosomal Ribonucleic Acid from HeLa Cells," *Arch. Biochem. Biophys.* 126:8-15 (1968)), and viral RNA (Beemon et al., "Localization of N6-Methyladenosine in the Rous Sarcoma Virus Genome," *J. Mol. Biol.* 113:165-179 (1977); Dimock et al., "Sequence Specificity of Internal Methylation in B77 Avian Sarcoma Virus RNA Subunits," *Biochemistry* 16:471-478 (1977)). However, while $m^6A$ is detectable in mRNA-enriched RNA fractions (Desrosiers et al., "Identification of Methylated Nucleosides in Messenger RNA from Novikoff Hepatoma Cells," *Proc. Natl. Acad. Sci. U.S.A.* 71:3971-3975 (1974)), it has been confirmed in vivo in only one mammalian mRNA (Horowitz et al., "Mapping of N6-Methyladenosine Residues in Bovine Prolactin mRNA," *Proc. Natl. Acad. Sci. U.S.A.* 81:5667-5671 (1984)). Preliminary experiments showed that $m^6A$ appeared to be enriched in the nucleus, indicating that it may be added before splicing (Chen-Kiang et al., "N-6-methyl-adenosine in Adenovirus Type 2 Nuclear RNA is Conserved in the Formation of Messenger RNA," *J. Mol. Biol.* 135:733-752 (1979)), but this was only a speculation about which transcripts were affected. It was not known if $m^6A$ is found on just a few transcripts, subset of transcripts, or on all transcripts, and it was not know if the $m^6A$ is randomly distributed within any given transcript or if it has unique localizations in mRNA.

Moreover, the abundance of $m^6A$ has been shown to be 0.1-0.4% of total adenosine residues in cellular RNA (Dubin et al., "The Methylation State of Poly A-Containing Messenger RNA from Cultured Hamster Cells," *Nucleic Acids Res.* 2:1653-1668 (1975); Perry et al., "The Methylated Constituents of L Cell Messenger RNA: Evidence for an Unusual Cluster at the 5' Terminus," *Cell* 4:387-394 (1975); Wei et al., "Methylated Nucleotides Block 5' Terminus of HeLa Cell Messenger RNA," *Cell* 4:379-386 (1975)), indicating that this modification may be widespread throughout the transcriptome.

Although the existence of modified bases in RNAs is known, transcriptome-wide characterization of modified bases in RNA has not previously been accomplished. This is due, in part, to the lack of available methods for detecting the presence of modified bases in RNA. Moreover, certain base modifications, such as $m^6A$, do not alter their ability to base pair with thymidine or uracil, so they are not amenable to detection with standard hybridization or sequencing-based methods.

The present invention is directed to overcoming these and other limitations in the art.

SUMMARY OF THE INVENTION

A first aspect of the present invention relates to a method of characterizing the modified base status of a transcriptome. This method involves contacting a transcriptome comprising one or more modified bases with an antibody specific to the one or more modified bases under conditions effective to bind the antibody to the one or more modified bases; isolating, from the transcriptome, a pool of RNA transcripts to which the antibody binds; and identifying isolated RNA transcripts that are present in a higher abundance in the isolated pool relative to the transcriptome, where each of said isolated RNA transcripts that are present in a higher abundance in the isolated pool together characterize the modified base status of the transcriptome.

A second aspect of the present invention relates to a method of diagnosis or prognosis of a disease or disorder associated with a modified base in RNA in a subject. This method involves obtaining a transcriptome from a subject, where the transcriptome comprises one or more modified bases; characterizing the modified base status of the transcriptome; and comparing the modified base status of the transcriptome to a known modified base status of a comparable transcriptome from a healthy and/or diseased subject to provide a diagnosis or prognosis of a disease or disorder in the subject.

A third aspect of the present invention relates to a method of determining the effect of a treatment on modified base levels of a transcriptome from a subject. This method involves characterizing the modified base status of a transcriptome comprising one or more modified bases from a subject before a treatment is administered to the subject; characterizing the modified base status of the transcriptome from the subject after a treatment is administered to the subject; and comparing the modified base status of the transcriptome after said treatment to the modified base status of the transcriptome before said treatment to determine the effect of the treatment on modified base levels of the transcriptome in the subject.

A fourth aspect of the present invention relates to a kit for characterizing the modified base status of a transcriptome. The kit includes an antibody that binds a modified base in RNA; one or more buffer solutions for carrying out antibody binding to a modified base in RNA, isolation of antibody-bound RNA, and/or sequencing of RNA molecules; and a computer-readable medium having stored thereon computer-readable instructions for comparing the abundance of an RNA transcript fragment in an isolated pool of RNA transcripts from a transcriptome to the abundance of that RNA transcript in the transcriptome prior to isolation thereof to identify isolated RNA transcripts that are present in a higher abundance in the isolated pool relative to the transcriptome, where each of said isolated RNA transcripts that are present in a higher abundance in the isolated pool together characterize the modified base status of the transcriptome.

The methods and kit of the present invention enable the characterization of the prevalence, regulation, and functional roles of modified bases in the transcriptome. Using antibodies that recognize modified bases in RNA transcripts, an affinity enrichment strategy has been developed which, when coupled with next-generation sequencing, allows for the high-throughput identification of modified base sites. Using this approach, the first transcriptome-wide profile of the modified base $m^6A$ in RNA is presented. Using the methods of the present invention it was found that $m^6A$ is a widespread modification that is present in the mRNAs of over 7,600 genes and in over 300 noncoding RNAs. Additionally, $m^6A$ is highly enriched near the stop codon and in the 3' UTR. Furthermore, bioinformatic analysis of $m^6A$ localization reveals consensus sites for $m^6A$ and identifies a potential interaction between $m^6A$ and microRNA pathways.

The present invention allows the identification of all the transcripts (coding and non-coding) in a given cell or tissue that contain modified (or substituted) base residues. In carrying out the methods of the present invention, it was found that a significant portion of the cellular transcriptome contains transcripts which contain one or more $m^6A$ residues. Thus, for example, the present invention allows for identification of transcripts which contain, or do not contain, detectable levels of $m^6A$.

The present invention also relates to identifying the sites within transcripts that are likely to contain modified base residues. It is possible that some disease states involve the loss of modified base residues at certain sites and not others. According to the present invention, one can determine the relative amount of any particular modified base in a transcript, relative to the amount of that modified base in the same transcript, but a different tissue. For example, based on a comparison between normal cells and cancer cells, predictions can be made about whether the modified base levels at specific sites within the tubulin transcript have increased or decreased.

The recent discovery that FTO, an obesity risk gene, encodes an $m^6A$ demethylase implicates $m^6A$ as an important regulator of physiological processes. The present invention shows that $m^6A$ is a highly prevalent base modification present in all tested tissues, but that also exhibits tissue-specific regulation and is markedly increased throughout brain development. Using a novel method for transcriptome-wide $m^6A$ localization, mRNAs of 7,676 genes were identified which contain $m^6A$, indicating that $m^6A$ is a common modification of mRNA. It was found that $m^6A$ sites are enriched near stop codons and in 3' UTRs, and an association between the presence of $m^6A$ residues and microRNA binding sites within 3' UTRs was uncovered. These findings provide a resource for identifying transcripts that are substrates for modified bases of RNA transcripts and reveal novel insights into the epigenetic regulation of the mammalian transcriptome.

BRIEF DESCRIPTION OF THE DRAWINGS

FIG. 1A depicts a dot blot analysis that demonstrates antibody specificity for $m^6A$. Increasing amounts of an oligonucleotide containing either $m^6A$ or unmodified adenosine were spotted onto a membrane and probed with the $m^6A$ antibody. While increased $m^6A$ immunoreactivity is observed in the presence of increasing concentrations of the $m^6A$ oligonucleotide (top), only background levels of immunoreactivity are observed at the highest concentrations of the A oligonucleotide (bottom). Blots shown are representative of results from three experiments. FIG. 1B shows competition dot blot assays that were performed on membranes spotted with 100 ng of $m^6A$-containing oligonucleotide. Antibody binding to the $m^6A$ oligonucleotide is attenuated by pre-incubation with increasing amounts of $m^6A$-containing competitor RNA (top), but not with RNA containing unmodified adenosine (bottom). Amount of competitor RNA used (left to right): 0 ng (0 nM), 10 ng (0.1 nM), 100 ng (1.1 nM), 1 μg (11.2 nM). Blots shown are representative of results from four experiments. In FIG. 1C, competition dot blot assays were performed as in FIG. 1B. The antibody was pre-incubated with increasing amounts of $N^6$-methyladenosine triphosphate ($N^6$-MeATP), adenosine triphosphate (ATP), $N^1$-methyladenosine triphosphate ($N^1$-MeATP), or 2'-O-methyladenosine triphosphate (2'-O-MeATP). Only $N^6$-MeATP is able to compete with antibody binding. Concentration of competitor nucleotide used (left to right): 0 μM, 1 μM, 2 μM, 4 μM. Blots shown are representative of results from three experiments. FIG. 1D illustrates detection of $m^6A$ in cellular DNA. Genomic DNA isolated from dam+ (containing $m^6A$) or dam– (lacking $m^6A$) E. coli was sheared and subjected to immunoblotting with the anti-$m^6A$ antibody. Although 1.5 times as much DNA from dam– E. coli was loaded (left panel), the antibody only recognizes the $m^6A$ present in DNA from dam+ E. coli (right panel). The blot shown is representative of results from three experiments.

FIG. 2A depicts widespread distribution of $m^6A$ levels in a variety of tissues. Total RNA isolated from mouse brain, heart, lung, liver, and kidney (top) was subjected to $m^6A$ immunoblot analysis. Ethidium bromide staining of the 28S rRNA is shown as a loading control (bottom). FIG. 2B is a graph showing quantification of $m^6A$ abundance within various tissues. Quantification of $m^6A$ immunoreactivity in FIG. 2A was measured by densitometry and normalized to the intensity of the corresponding 28S rRNA band for each tissue (n=3; data are presented as mean+SEM). FIG. 2C shows $m^6A$ that is enriched within mRNAs. Oligo(dT) DYNABEADS were used to isolate poly(A) RNA from total mouse brain RNA, and the unbound "flow-through" RNA was saved as the poly(A)-depleted fraction. Equal amounts of total RNA, poly(A) RNA, and poly(A)-depleted RNA were then subjected to $m^6A$ immunoblot analysis (top). Ethidium bromide staining of 28S rRNA is shown as a loading control (bottom). Intense $m^6A$ immunoreactivity is observed in the poly(A) RNA fraction, consistent with high levels of $m^6A$ within mature mRNAs. FIG. 2D shows that depletion of poly(A) tails from mRNA does not reduce levels of $m^6A$ in mRNA. Poly(A) RNA was isolated from total mouse brain RNA using oligo(dT) DYNABEADS. Half the sample was then subjected to poly(A) tail depletion by hybridizing to oligo(dT) primers and digestion with RNase H. Immunoblot analysis with the $m^6A$ antibody (top panel) shows that levels of $m^6A$ in poly(A) RNA (left) and poly(A) tail-depleted RNA (right) are comparable. Removal of poly(A) tails was confirmed using 3'RACE and RT-PCR to detect β-actin; no product is detected in the tail-depleted sample when oligo (dT) primers are used for cDNA synthesis (middle panel). As a control, use of random hexamers successfully generates a product in both samples (bottom panel).

FIGS. 3A-3B depict regulation of m⁶A levels in cells and during development. FIG. 3A shows ontogeny of m⁶A abundance throughout brain development. Total RNA was isolated from mouse brain at embryonic day 18 (E18), postnatal day 0 (P0), postnatal day 14 (P14), and adulthood (Adult), then subjected to immunoblot analysis to detect m⁶A-containing transcripts. Ethidium bromide staining of 28S rRNA bands is shown as a loading control. FIG. 3B shows that FTO demethylates a wide range of cellular transcripts. FTO was expressed in HEK293T cells for 48 hours, and cellular RNA was subjected to immunoblot analysis to detect m⁶A.

FIG. 4A is a schematic representation of MeRIP-Seq. Total RNA is subjected to RiboMinus treatment to remove rRNA species. RNAs containing m⁶A are then immunoprecipitated by mixing the RNA with m⁶A antibody-coupled Dynabeads. m⁶A-containing RNAs are then eluted from the antibody-coupled beads and subjected to a second round of m⁶A immunoprecipitation. The resulting RNA pool, which is highly enriched for m⁶A-containing RNAs, is then subjected to next-generation sequencing. FIG. 4B shows a schematic of sequencing reads and their alignment to locations in the genome surrounding an m⁶A site. The top figure shows an mRNA that contains a single m⁶A residue along its length. The middle figure shows individual, 100 nt-wide mRNA fragments which are isolated following m⁶A immunoprecipitation, each of which contains the same m⁶A residue from the mRNA depicted above. The bottom figure is a histogram showing predicted frequency of MeRIP-Seq reads obtained by sequencing individual immunoprecipitated fragments. Read frequency is predicted to increase with closer proximity to the m⁶A site, forming a "peak" which is roughly 200 nt wide at its base and 100 nt wide at its midpoint. FIG. 4C shows that sequencing reads from MeRIP-Seq converge over m⁶A sites. Representative UCSC Genome Browser plot from MeRIP-Seq data which demonstrates typical read frequency peak formation surrounding a site of m⁶A (shown here is the 3' UTR of Pax6). Peak height is displayed as reads per base per million mapped reads (BPM).

FIG. 5A shows that different sequencing platforms and antibodies result in similar m⁶A profiles. UCSC Genome Browser tracks displaying read clusters from three MeRIP-Seq replicates (MeRIP1, MeRIP2, and MeRIP3) are shown along the length of the Ldlr transcript. The upper-most track (non-IP) represents the non-immunoprecipitated control sample. FIG. 5B shows validation of m⁶A-containing mRNA identified with MeRIP-Seq. Hybridization-based RNA pulldown was used to isolate Ldlr mRNA from total brain RNA, followed by confirmation of m⁶A presence (arrow) by immunoblot analysis with anti-m⁶A. A control sample using a non-specific probe of equal size (Control Probe) was run in parallel. Total mouse brain RNA (Input RNA) is shown as a reference for m⁶A labeling. FIG. 5C illustrates transcriptome-wide distribution of m⁶A peaks. Pie charts show the percentage of m⁶A peaks (top) and non-IP sample reads (bottom) within distinct RNA sequence types. m⁶A is highly enriched in 3' UTRs and coding sequences ("CDSs") compared to the distribution of reads in the non-IP samples. FIG. 5D is a graph showing the distribution of m⁶A peaks across the length of mRNA transcripts. 5' UTRs, CDSs, and 3' UTRs of RefSeq mRNAs were individually binned into regions spanning 1% of their total length, and the percentage of m⁶A peaks that fall within each bin was determined. The moving averages of mouse brain peaks percentage and HEK293T peak percentage are shown. FIG. 5E shows that highly similar m⁶A peak distribution is observed within many human and mouse transcripts. UCSC Genome Browser plots are used to show MeRIP-Seq read clusters in the representative transcript SREK1. MeRIP-Seq reads cluster at the same distinct regions of SREK1 in both HEK293T cell RNA (top) and mouse brain RNA (bottom).

FIGS. 6A-6F show that MeRIP-Seq reveals features of m⁶A in mRNA. FIG. 6A shows phylogenetic conservation of m⁶A peaks. PhyloP scores of m⁶A peak regions were compared to those of randomly shuffled regions throughout gene exons. There was a significantly higher median conservation score (K-S test, * p≤2.2e⁻¹⁶) in m⁶A peaks (0.578) than in the random regions (0.023). FIG. 6B shows sequence motifs identified within m⁶A peaks. The motif G[AG]ACU and variants thereof ([AC]GAC[GU], GGAC, [AU][CG]G[AG] AC, and UGAC) were highly enriched in m⁶A peaks. Additionally, one U-rich motif (bottom right) was identified as being significantly underrepresented within m⁶A peaks. Bars under each motif indicate the degree of underrepresentation (black) or overrepresentation (gray) within regions of m⁶A peaks in the non-IP control sample (CNTL) and the MeRIP sample (MeRIP). FIG. 6C illustrates that m⁶A motif sequences frequently lie near the center of m⁶A peaks. Shown is a plot of the cumulative distribution of m⁶A motif positions within m⁶A peaks containing a single motif. Motifs cluster in the center of peaks, indicating that the methylated adenosines in these motifs account for the m⁶A peaks identified in MeRIP-Seq. FIG. 6D is an example of a m⁶A motif sequence (SEQ ID NO:26) near the center of a peak. A UCSC Genome Browser plot containing tracks for MeRIP-Seq reads (red) and non-IP control reads (black) at the Ilf2 locus is shown. The m⁶A peak within the Ilf2 3' UTR contains a single m⁶A motif identified in FIG. 6B. The sequence of this motif (highlighted in gray) is located at the center of the m⁶A peak. FIG. 6E shows distribution of m⁶A peaks and miRNA target sites within 3' UTRs. The frequency of m⁶A peaks and miRNA target sites along the length of 3' UTRs is shown. FIG. 6F shows the association between 3' UTR methylation and miRNA abundance. The 25 most abundant miRNAs in brain have a significantly greater percentage of m⁶A peaks within their target mRNA 3' UTRs than do the 25 most weakly expressed brain miRNAs (*p<0.05, Wilcoxon test).

FIGS. 7A-7E show validation of MeRIP-Seq target mRNAs. FIG. 7A shows that MeRIP-Seq identifies Drd1a as an mRNA containing m⁶A. UCSC Genome Browser tracks displaying read clusters from a MeRIP-Seq sample (bottom) and a non-IP control sample (top). Drd1a exhibits distinct m⁶A peaks in the MeRIP sample, whereas it lacks these peaks in the non-IP sample. Peak height is displayed as reads per base per million mapped reads (BPM). FIG. 7B shows confirmation of the presence of m⁶A in Drd1a, an mRNA identified with MeRIP-Seq. Drd1a mRNA was isolated from total mouse brain RNA using a biotinylated oligonucleotide probe in an RNA pull-down. Immunoblot analysis with the anti-m⁶A antibody was then performed to confirm m⁶A presence in Drd1a. A control sample using a probe of equal size that is not specific for any known mouse mRNA (Control Probe) was run in parallel. Total mouse brain RNA (Input) is also shown as a reference for m⁶A labeling. Arrows indicate m⁶A-immunoreactive band following pull-down of Drd1a. The size of the band is consistent with known molecular weights of Drd1a transcript variants (Thierry-Mieg et al., "AceView: A Comprehensive cDNA-Supported Gene and Transcripts Annotation," *Genome Biol.* 7 (Suppl. 1):11-14 (2006), which is hereby incorporated by reference in its entirety). FIG. 7C illustrates that MeRIP-Seq identifies Grm1 as an mRNA $m^6A$-containing mRNA. UCSC Genome Browser tracks displaying read clusters from a MeRIP-Seq sample (bottom) and the control sample, which comprised the RNA sample prior to immunoprecipitation with the anti-$m^6A$ antibody ("non-IP," top). Grm1 exhibits distinct $m^6A$ peaks along its length in the MeRIP sample, whereas it lacks these peaks in the non-IP sample. Peak height is displayed as reads per base per million mapped reads (BPM). FIG. 7D shows validation of the presence of $m^6A$ in the Grm1 mRNA. Grm1 mRNA was isolated from total mouse brain RNA using a target-specific, biotinylated oligonucleotide probe as in FIG. 7B. Immunoblot analysis with anti-$m^6A$ was subsequently performed to confirm $m^6A$ presence. Total mouse brain RNA (Input) is also shown, as is the results of a control sample using no probe (No Probe). An $m^6A$ immunoreactive band is observed following pull-down of Grm1 (arrow). The size of the band is consistent with known molecular weights of Grm1 transcript variants (Thierry-Mieg et al., "AceView: A Comprehensive cDNA-Supported Gene and Transcripts Annotation," *Genome Biol.* 7 (Suppl. 1):11-14 (2006), which is hereby incorporated by reference in its entirety). FIG. 7E shows immunodepletion of $m^6A$-containing mRNAs from complex RNA samples following $m^6A$ immunoprecipitation. RiboMinus-treated mouse brain RNA was fragmented and subjected to $m^6A$ immunoprecipitation. Unbound RNAs were isolated, and the abundance of target RNAs was measured by qRT-PCR. All transcripts were normalized to the amount of Rps14 mRNA within each sample. Rps14 was chosen because it is an abundant transcript which does not have $m^6A$ peaks. Compared to the input RNA, the levels of Rps21 and Ndel1, two transcripts which lack $m^6A$ peaks, show only slight decreases in the unbound sample (which might be due to non-specific binding of RNA to the magnetic beads used during immunoprecipitation). However, the levels of Drd1a, Grm1, Ptpn4, and Tlr3, all transcripts which contain $m^6A$ peaks, are dramatically decreased in the unbound RNA fraction, indicating that the $m^6A$ antibody selectively immunodepletes these methylated transcripts from the unbound RNA pool.

FIG. 8A is a graph illustrating that many transcripts contain adjacent $m^6A$ peaks. The number of transcriptome-wide $m^6A$ peaks that are contiguous with neighboring $m^6A$ peaks is shown. Many $m^6A$ peaks occur singly (1 peak within a cluster), although the majority of peaks are part of adjacent peak pairs (2 peaks within a cluster) or contiguous peak triplets (3 peaks within a cluster). A small number of peaks are highly clustered (4 or more peaks within a cluster). This data demonstrates that some transcripts contain a single region of adenosine methylation, whereas other transcripts are multi-methylated on several adenosine residues which cluster in distinct regions of a transcript. FIG. 8B depicts a number of motifs found in $m^6A$ peaks. The percentage of $m^6A$ peaks that contain various numbers of the motifs identified (in FIG. 8B) was determined. Only 10% of $m^6A$ peaks lack a motif, whereas the majority of peaks (57.3%) contain one or two motifs. 28.5% of $m^6A$ peaks have only a single motif within their sequence, indicating that a single $m^6A$ residue accounts for these peaks. FIG. 8C shows the relationship between $m^6A$ peak enrichment and mRNA abundance in mouse brain. Plotted is the peak enrichment value (the ratio of MeRIP sample reads to non-IP sample reads within the area of a peak, each normalized to the number of reads within the sample) relative to the abundance of the transcript within the input RNA. The RPKM (reads per kilobase per million mapped reads) of mRNAs in the non-IP sample (y-axis) provides an estimate of transcript abundance within the input RNA. The most highly enriched $m^6A$ peaks are often observed in transcripts of low abundance. FIG. 8D shows the relationship between $m^6A$ peak enrichment and mRNA abundance in HEK293T cells. The enrichment of individual $m^6A$ peaks is plotted relative to the abundance of the transcript in which the peak resides as in FIG. 8C. As in the mouse brain dataset, there is a tendency for highly enriched $m^6A$ peaks to occur in weakly expressed transcripts.

FIG. 9A indicates distribution of $m^6A$ peaks surrounding the CDS start site. The distribution of $m^6A$ peaks 1 kb upstream and downstream of the CDS start sites of known RefSeq genes is shown. A steady increase in the number of peaks is observed which plateaus approximately 500 nt after the CDS start site. FIG. 9B shows distribution of $m^6A$ peaks surrounding the CDS end site. The distribution of $m^6A$ peaks 1 kb upstream and downstream of the CDS end sites of known RefSeq genes is shown. A strong and very distinct enrichment of $m^6A$ peaks surrounding the stop codon is observed. In FIG. 9C, distribution of $m^6A$ enrichment along the length of mRNA transcripts in mouse is shown. Peaks that fell within gene exons were mapped to percentile locations within the 5' UTR, CDS and 3' UTR segments of the mature transcript. Shown is the sum of the enrichments of the peaks that fell within each percentile bin. $m^6A$ enrichment is particularly strong at the 3' end of the CDS and the 5' end of the 3' UTR. In FIG. 9D, transcriptome-wide distribution of HEK293T $m^6A$ peaks is shown. The pie chart of FIG. 9D shows the percentage of $m^6A$ peaks within distinct RNA sequence types. $m^6A$ is highly enriched in 3' UTRs and CDSs, similar to the pattern observed in mouse brain RNA (FIG. 5C).

In FIG. 10A, cell line-specific changes in the levels of $m^6A$ indicate its dynamic nature. RNA was isolated from various mammalian cell lines and subjected to immunoblot analysis with the anti-$m^6A$ antibody. The levels of $m^6A$ vary substantially across different cell lines. For instance, the cancer cell lines HEPG2 and MCF7 appear to have relatively high levels of $m^6A$, whereas the prostate cancer cell lines PC3 and PC9 have comparatively low levels. $m^6A$ immunoblotting of total mRNA often reveals two bands of low signal intensity that are approximately 1.9 kb and 5 kb in size, which correspond to the 18S and 28S rRNA species, respectively. This likely indicates low levels of $m^6A$ within these rRNAs. FIG. 10B shows that developmentally regulated increases in $m^6A$ abundance are observed in cultured neurons. RNA was collected from cultured neurons isolated from embryonic day 18 (E18) and postnatal day 3 (P3) rat brain and subjected to immunoblot analysis with the anti-$m^6A$ antibody. A substantial increase in $m^6A$ abundance is observed in P3 neurons compared to E18 neurons, despite loading of less RNA in the P3 sample (indicated by ethidium bromide (EtBr) staining of 28S rRNA bands, bottom panel). Additionally, compared to RNA isolated from adult rat brain tissue, the $m^6A$ content of E18 or P3 cultured neuronal RNA is significantly enriched in lower molecular weight RNA species.

In FIG. 11A, $m^6A$ is increased in brain RNA from Alzheimer's disease patients. Dot blot analysis was performed using equal amounts of total human brain RNA from five Alzheimer's disease patients and two healthy controls. An anti-$m^6A$ antibody was used for the detection of $m^6A$. $m^6A$ levels are substantially elevated in Alzheimer's disease samples compared to samples from healthy human brain, indicating that increased adenosine methylation might be a feature of Alzheimer's disease brain mRNA. FIG. 11B shows that $m^6A$ levels are increased in a cellular model of human cancer. Lymphoma B cells were subjected to heat shock treatment (HS), which induces the expression of cancer-related genes. Total RNA was isolated and subjected to dot blot analysis using an anti-$m^6A$ antibody for detection of $m^6A$ levels. Compared to untreated cells (No HS), heat shock treatment increases the level of $m^6A$ in lymphoma B cells, indicating that elevated $m^6A$ levels are a potential feature of some human cancers.

DETAILED DESCRIPTION OF THE INVENTION

Figure 1A:
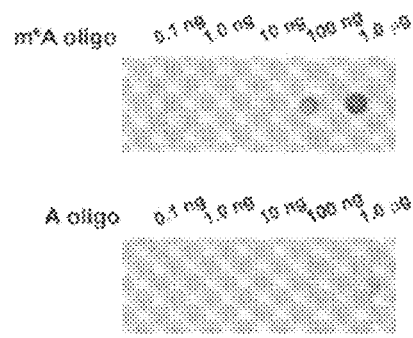
FIGS. 1A-1D demonstrate the specificity and sensitivity of $m^6A$-specific antibody. In particular.

The present invention is directed to characterizing a transcriptome according to the presence of modified bases in the RNA transcripts contained in the transcriptome. Thus, in one aspect of the present invention, a transcriptome is characterized by the presence of modified bases in the RNA transcripts contained in the transcriptome by contacting a transcriptome comprising one or more modified bases with an antibody specific to the one or more modified bases under conditions effective to bind the antibody to the one or more modified bases.

As used herein, the term "transcriptome" refers to all RNA molecules produced in one or a population of cells, or a selection of specific types of RNA molecules (e.g., mRNA vs. ncRNA, or specific mRNAs within an mRNA transcriptome) contained in a complete transcriptome. A person of ordinary skill in the art will appreciate that there are many types of RNA molecules in any given transcriptome, including coding RNA (i.e., RNA that is translated into a protein, e.g., mRNA) and non-coding RNA. Table 1 below provides a listing of the various types of RNA molecules found in a transcriptome, all of which may contain modified bases, and each of which is a type of RNA molecule contemplated by the present invention.

TABLE 1

| RNA Types | | |
|---|---|---|
| Full Name | Abb. Name | Functional Description |
| 7SK RNA | 7SK | Negatively regulating CDK9/cyclin T complex |
| Signal recognition particle RNA | 7SRNA | Membrane integration |
| Antisense RNA | aRNA | Regulatory |
| CRISPR RNA | crRNA | Resistance to parasites |
| Guide RNA | gRNA | mRNA nucleotide modification |
| Long noncoding RNA | lncRNA | XIST (dosage compensation), HOTAIR (cancer) |
| MicroRNA | miRNA | Gene regulation |
| Messenger RNA | mRNA | Codes for protein |
| Piwi-interacting RNA | piRNA | Transposon defense, maybe other functions |
| Repeat associated siRNA | rasiRNA | Type of piRNA; transposon defense |
| Retrotransposon | retroRNA | self-propagation |
| Ribonuclease MRP | RNase MRP | rRNA maturation, DNA replication |
| Ribonuclease P | RNase P | tRNA maturation |
| Ribosomal RNA | rRNA | Translation |
| Small Cajal body-specific RNA | scaRNA | Guide RNA to telomere in active cells |
| Small interfering RNA | siRNA | Gene regulation |
| SmY RNA | SmY | mRNA trans-splicing |
| Small nucleolar RNA | snoRNA | Nucleotide modification of RNAs |
| Small nuclear RNA | snRNA | Splicing and other functions |
| Trans-acting siRNA | tasiRNA | Gene regulation |
| Telomerase RNA | telRNA | Telomere synthesis |
| Transfer-messenger RNA | tmRNA | Rescuing stalled ribosomes |
| Transfer RNA | tRNA | Translation |
| Viral Response RNA | viRNA | Anti-viral immunity |
| Vault RNA | vRNA | self-propagation |
| Y RNA | yRNA | RNA processing, DNA replication |

As used herein, a "modified base" is, according to one embodiment, a ribonucleotide base of uracil, cytosine, adenine, or guanine that possesses a chemical modification from its normal structure. For example, one type of modified base is a methylated base, such as $N^6$-methyladenosine ($m^6A$). According to another embodiment, a modified base according to the present invention is a substituted base, meaning the base possesses a structural modification that renders it a chemical entity other than uracil, cytosine, adenine, or guanine. For example, pseudouridine is one type of substituted RNA base. Modified bases of the present invention include those now known, and those yet to be discovered. This method of the present invention is applicable to many other types of modifications. Table 2 below provides a list of modified bases encompassed by the present invention.

TABLE 2

| List of Base Modifications | |
|---|---|
| Abbreviation | Chemical name |
| $m^1acp^3Y$ | 1-methyl-3-(3-amino-3-carboxypropyl) pseudouridine |
| $m^1A$ | 1-methyladenosine |
| $m^1G$ | 1-methylguanosine |

TABLE 2-continued

List of Base Modifications

| Abbreviation | Chemical name |
|---|---|
| $m^1I$ | 1-methylinosine |
| $m^1Y$ | 1-methylpseudouridine |
| $m^1Am$ | 1,2'-O-dimethyladenosine |
| $m^1Gm$ | 1,2'-O-dimethylguanosine |
| $m^1Im$ | 1,2'-O-dimethylinosine |
| $m^2A$ | 2-methyladenosine |
| $ms^2io^6A$ | 2-methylthio-$N^6$-(cis-hydroxyisopentenyl) adenosine |
| $ms^2hn^6A$ | 2-methylthio-$N^6$-hydroxynorvalyl carbamoyladenosine |
| $ms^2i^6A$ | 2-methylthio-$N^6$-isopentenyladenosine |
| $ms^2m^6A$ | 2-methylthio-$N^6$-methyladenosine |
| $ms^2t^6A$ | 2-methylthio-$N^6$-threonyl carbamoyladenosine |
| $s^2Um$ | 2-thio-2'-O-methyluridine |
| $s^2C$ | 2-thiocytidine |
| $s^2U$ | 2-thiouridine |
| Am | 2'-O-methyladenosine |
| Cm | 2'-O-methylcytidine |
| Gm | 2'-O-methylguanosine |
| Im | 2'-O-methylinosine |
| Ym | 2'-O-methylpseudouridine |
| Um | 2'-O-methyluridine |
| Ar(p) | 2'-O-ribosyladenosine (phosphate) |
| Gr(p) | 2'-O-ribosylguanosine (phosphate) |
| $acp^3U$ | 3-(3-amino-3-carboxypropyl)uridine |
| $m^3C$ | 3-methylcytidine |
| $m^3Y$ | 3-methylpseudouridine |
| $m^3U$ | 3-methyluridine |
| $m^3Um$ | 3,2'-O-dimethyluridine |
| imG-14 | 4-demethylwyosine |
| $s^4U$ | 4-thiouridine |
| $chm^5U$ | 5-(carboxyhydroxymethyl)uridine |
| $mchm^5U$ | 5-(carboxyhydroxymethyl)uridine methyl ester |
| $inm^5s^2U$ | 5-(isopentenylaminomethyl)-2-thiouridine |
| $inm^5Um$ | 5-(isopentenylaminomethyl)-2'-O-methyluridine |
| $inm^5U$ | 5-(isopentenylaminomethyl)uridine |
| $nm^5s^2U$ | 5-aminomethyl-2-thiouridine |
| $ncm^5Um$ | 5-carbamoylmethyl-2'-O-methyluridine |
| $ncm^5U$ | 5-carbamoylmethyluridine |
| $cmnm^5Um$ | 5-carboxymethylaminomethyl-2'-O-methyluridine |
| $cmnm^5s^2U$ | 5-carboxymethylaminomethyl-2-thiouridine |
| $cmnm^5U$ | 5-carboxymethylaminomethyluridine |
| $cm^5U$ | 5-carboxymethyluridine |
| $f^5Cm$ | 5-formyl-2'-O-methylcytidine |
| $f^5C$ | 5-formylcytidine |
| $hm^5C$ | 5-hydroxymethylcytidine |
| $ho^5U$ | 5-hydroxyuridine |
| $mcm^5s^2U$ | 5-methoxycarbonylmethyl-2-thiouridine |
| $mcm^5Um$ | 5-methoxycarbonylmethyl-2'-O-methyluridine |
| $mcm^5U$ | 5-methoxycarbonylmethyluridine |
| $mo^5U$ | 5-methoxyuridine |
| $m^5s^2U$ | 5-methyl-2-thiouridine |
| $mnm^5se^2U$ | 5-methylaminomethyl-2-selenouridine |
| $mnm^5s^2U$ | 5-methylaminomethyl-2-thiouridine |
| $mnm^5U$ | 5-methylaminomethyluridine |
| $m^5C$ | 5-methylcytidine |
| $m^5D$ | 5-methyldihydrouridine |
| $m^5U$ | 5-methyluridine |
| $tm^5s^2U$ | 5-taurinomethyl-2-thiouridine |
| $tm^5U$ | 5-taurinomethyluridine |
| $m^5Cm$ | 5,2'-O-dimethylcytidine |
| $m^5Um$ | 5,2'-O-dimethyluridine |
| $preQ_1$ | 7-aminomethyl-7-deazaguanosine |
| $preQ_0$ | 7-cyano-7-deazaguanosine |
| $m^7G$ | 7-methylguanosine |
| $G^+$ | archaeosine |
| D | dihydrouridine |
| oQ | epoxyqueuosine |
| galQ | galactosyl-queuosine |
| OHyW | hydroxywybutosine |
| I | inosine |
| imG2 | isowyosine |
| $k^2C$ | lysidine |
| manQ | mannosyl-queuosine |
| mimG | methylwyosine |
| $m^2G$ | $N^2$-methylguanosine |
| $m^2Gm$ | $N^2$,2'-O-dimethylguanosine |
| $m^{2,7}G$ | $N^2$,7-dimethylguanosine |
| $m^{2,7}Gm$ | $N^2$,7,2'-O-trimethylguanosine |
| $m^2_2G$ | $N^2,N^2$-dimethylguanosine |
| $m^2_2Gm$ | $N^2,N^2$,2'-O-trimethylguanosine |
| $m^{2,2,7}G$ | $N^2,N^2$,7-trimethylguanosine |
| $ac^4Cm$ | $N^4$-acetyl-2'-O-methylcytidine |
| $ac^4C$ | $N^4$-acetylcytidine |
| $m^4C$ | $N^4$-methylcytidine |
| $m^4Cm$ | $N^4$,2'-O-dimethylcytidine |
| $m^4_2Cm$ | $N^4,N^4$,2'-O-trimethylcytidine |
| $io^6A$ | $N^6$-(cis-hydroxyisopentenyl)adenosine |
| $ac^6A$ | $N^6$-acetyladenosine |
| $g^6A$ | $N^6$-glycinylcarbamoyladenosine |
| $hn^6A$ | $N^6$-hydroxynorvalylcarbamoyladenosine |
| $i^6A$ | $N^6$-isopentenyladenosine |
| $m^6t^6A$ | $N^6$-methyl-$N^6$-threonylcarbamoyladenosine |
| $m^6A$ | $N^6$-methyladenosine |
| $t^6A$ | $N^6$-threonylcarbamoyladenosine |
| $m^6Am$ | $N^6$,2'-O-dimethyladenosine |
| $m^6_2A$ | $N^6,N^6$-dimethyladenosine |
| $m^6_2Am$ | $N^6,N^6$,2'-O-trimethyladenosine |
| $o_2yW$ | peroxywybutosine |
| Y | pseudouridine |
| Q | queuosine |
| OHyW | undermodified hydroxywybutosine |
| $cmo^5U$ | uridine 5-oxyacetic acid |
| $mcmo^5U$ | uridine 5-oxyacetic acid methyl ester |
| yW | wybutosine |
| imG | wyosine |

Antibodies specific to modified bases have previously been described. For example, antibodies to $m^6A$ have been described by Munns et al., "Characterization of Antibodies Specific for $N^6$-Methyladenosine and for 7-Methylguanosine," *Biochemistry* 16:2163-2168 (1977), which is now commercially available through Synaptic Systems (SySy; Germany) and Kong et al., "Functional Analysis of Putative Restriction-Modification System Genes in the *Helicobacter pylori* J99 Genome," *Nucleic Acids Res.* 28:3216-3223 (2000), both of which are hereby incorporated by reference in their entirety. Antibodies specific to 5-methylcytidine ($m^5C$) have been shown to react with $m^5C$ in mammalian DNA bound to nitrocellulose paper (Achwal et al., "Immunochemical Evidence for the Presence of 5mC, 6mC and 7mG in Human, *Drosophila* and Mealybug DNA," *FEBS Lett.* 158:353-358 (1983); Achwal & Chandra, "A Sensitive Immunochemical method for Detecting 5mC in DNA Fragments," *FEBS Lett.* 150:469-472 (1982), each of which is hereby incorporated by reference in its entirety). Immunofluorescence has also been used to determine chromosomal regions with a high frequency of $m^5C$ (Barbin et al., "New Sites of Methylcytosine-rich DNA Detected on Metaphase Chromosomes," *Hum. Genet.* 94:684-692 (1994), which is hereby incorporated by reference in its entirety). Mouse monoclonal antibody against 5-methylcytidine has also been used previously to detect alterations in the urinary excretion of nucleosides by cancer patients (Tebib et al., "Relationship Between Urinary Excretion of Modified Nucleosides and Rheumatoid Arthritis Process," *Br. J. Rheumatol.* 36:990-995 (1997), which is hereby incorporated by reference in its entirety) and to visualize the distribution of methylated sequences along mammalian chromosomes in normal and malignant cells (Hernandez-Blazquez et al., "Evaluation of Global DNA Hypomethylation in Human Colon Cancer Tissues by Immunohistochemistry and Image Analysis," *Gut* 47:689-693 (2000); Mayer et al., "Demethylation of the Zygotic Paternal Genome," *Nature* 403:501-502 (2000), each of which are hereby incorporated by reference in their entirety).

Antibodies specific to methylated bases are available commercially. For example, a mouse monoclonal antibody against m$^5$C is available from Eurogentec S.A. (Belgium) and a rabbit polyclonal serum is available from Megabase Research Products (USA). Polyclonal rabbit antisera against other methylated bases (6-methyladenosine and 7-methylguanosine) are also available (Megabase Research Products, USA).

An antibody against inosine is described in Inouye et al., "Detection of Inosine-containing Transfer Ribonucleic Acid Species by Affinity Chromatography on Columns of Anti-Inosine Antibodies," *J. Biol. Chem.* 248:8125-8129 (1973), which is hereby incorporated by reference in its entirety.

Several companies sell antibodies against hm$^5$C, including Active Motif, Millipore, and Sigma.

Antibodies useful in the methods of the present invention can also be developed according to methods known and practiced by persons of ordinary skill in the art. Such antibodies may be monoclonal antibodies, polyclonal antibodies, or functional fragments or variants thereof. The term "antibody" as used herein should be construed as covering any specific binding substance having a binding domain with the required specificity. Thus, this term covers antibody fragments, derivatives, functional equivalents, and homologues of antibodies, including any polypeptide comprising an immunoglobulin binding domain, whether natural or synthetic, monoclonal or polyclonal. Chimeric molecules comprising an immunoglobulin binding domain, or equivalent, fused to another polypeptide are also included, as described in more detail infra.

Monoclonal antibody production can be effected by techniques that are well known in the art. Basically, the process involves first obtaining immune cells (lymphocytes) from the spleen of a mammal (e.g., mouse) that has been previously immunized with the antigen of interest either in vivo or in vitro. The antibody-secreting lymphocytes are then fused with myeloma cells or transformed cells, which are capable of replicating indefinitely in cell culture. The resulting fused cells, or hybridomas, are immortal, immunoglobulin-secreting cell lines that can be cultured in vitro. Upon culturing the hybridomas, the resulting colonies can be screened for the production of desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, "Continuous Cultures of Fused Cells Secreting Antibody of Predefined Specificity," *Nature* 256:495 (1975), which is hereby incorporated by reference in its entirety.

Mammalian lymphocytes are immunized by in vivo immunization of the animal (e.g., a mouse, rat, rabbit, or human). Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (see Milstein and Kohler, "Derivation of Specific Antibody-producing Tissue Culture and Tumor Lines by Cell Fusion," *Eur. J. Immunol.* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described. Human hybridomas can be prepared using the EBV-hybridoma technique monoclonal antibodies (see Cole et al., in *Monoclonal Antibodies and Cancer Therapy*, Alan R. Liss, Inc., pp. 77-96 (1985), which is hereby incorporated by reference in its entirety). Human antibodies may be used and can be obtained by using human hybridomas (Cote et al., "Generation of Human Monoclonal Antibodies Reactive with Cellular Antigens," *Proc. Natl. Acad. Sci. USA* 80:2026-2030 (1983), which is hereby incorporated by reference in its entirety) or by transforming human B cells with EBV virus in vitro (Cole et al., in *Monoclonal Antibodies and Cancer Therapy*, Alan R. Liss, Inc., pp. 77-96 (1985), which is hereby incorporated by reference in its entirety). In addition, monoclonal antibodies can be produced in germ-free animals (see PCT/US90/02545, which is hereby incorporated by reference in its entirety).

Procedures for raising polyclonal antibodies are also well known. Typically, such antibodies can be raised by administering the antigen subcutaneously to rabbits, mice, or rats which have first been bled to obtain pre-immune serum. The antigens can be injected as tolerated. Each injected material can contain adjuvants and the selected antigen (preferably in substantially pure or isolated form). Suitable adjuvants include, without limitation, Freund's complete or incomplete mineral gels such as aluminum hydroxide, surface active substances such as lysolecithin, pluronic polyols, polyanions, peptides, oil emulsions, dinitrophenol, and potentially useful human adjuvants such as bacille Calmette-Guerin and *Carynebacterium parvum*. The subject mammals are then bled one to two weeks after the first injection and periodically boosted with the same antigen (e.g., three times every six weeks). A sample of serum is then collected one to two weeks after each boost. Polyclonal antibodies can be recovered from the serum by affinity chromatography using the corresponding antigen to capture the antibody. This and other procedures for raising polyclonal antibodies are disclosed in Harlow & Lane, editors, *Antibodies: A Laboratory Manual* (1988), which is hereby incorporated by reference in its entirety.

In addition, techniques developed for the production of chimeric antibodies (Morrison et al., "Chimeric Human Antibody Molecules: Mouse Antigen-binding Domains with Human Constant Region Domains," *Proc. Natl. Acad. Sci. USA* 81:6851-6855 (1984); Neuberger et al., "Recombinant Antibodies Possessing Novel Effector Functions," *Nature* 312:604-608 (1984); Takeda et al., "Construction of Chimaeric Processed Immunoglobulin Genes Containing Mouse Variable and Human Constant Region Sequences," *Nature* 314:452-454 (1985), each of which is hereby incorporated by reference in its entirety) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (see e.g., U.S. Pat. No. 4,816,567 to Cabilly et al., and U.S. Pat. No. 4,816,397 to Boss et al., each of which is hereby incorporated by reference in its entirety).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associate with each other to form an antigen binding site: antigen binding sites are formed by the association of the first domain of one polypeptide within the multimer with the second domain of another polypeptide within the multimer (see WO94/13804).

Alternatively, techniques described for the production of single chain antibodies (see e.g., U.S. Pat. No. 4,946,778 to Ladner et al.; Bird et al., "Single-chain Antigen-binding Proteins," *Science* 242:423-426 (1988); Huston et al., "Protein Engineering of Antibody Binding Sites: Recovery of Specific Activity in an Anti-dogoxin Single-chain Fv Analogue Produced in *Escherichia coli,*" *Proc. Natl. Acad. Sci. USA* 85:5879-5883 (1988); Ward et al., "Binding Activities of a Repertoire of Single Immunoglobulin Variable Domains Secreted from *Escherichia coli,*" *Nature* 334:544-546 (1989), each of which is hereby incorporated by reference in its entirety) can be adapted to produce single chain antibodies against modified bases. Single chain antibodies are formed by linking the heavy and light chain fragments of the Fv region via an amino acid bridge, resulting in a single chain polypeptide.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, Academic Press (New York), pp. 98-118 (1983), which is hereby incorporated by reference in its entirety. Alternatively, the Fab fragments can be generated by treating the antibody molecule with papain and a reducing agent. Alternatively, Fab expression libraries may be constructed (see Huse et al., "Generation of a Large Combinatorial Library of the Immunoglobulin Repertoire in Phage Lambda," *Science* 246:1275-1281 (1989), which is hereby incorporated by reference in its entirety) to allow rapid and easy identification of monoclonal Fab fragments with the desired specificity.

Antibodies may be isolated by standard techniques known in the art, such as immunoaffinity chromatography, centrifugation, precipitation, etc. The antibodies (or fragments or variants thereof) are preferably prepared in a substantially purified form (i.e., at least about 85% pure, more preferably 90% pure, even more preferably at least about 95% to 99% pure).

In one embodiment, the antibody used in the methods of the present invention is an anti-m$^6$A antibody.

According to the present invention, conditions effective to bind an antibody to a modified base are known or can be determined by persons of ordinary skill in the art. For example, an appropriate ionic balance in the sample can assist the antibody in effectively binding to the modified base. The pH of a sample can be controlled by addition of suitable buffers such as sodium phosphate, which will maintain the pH at approximately 7.0. Salts, such as sodium chloride may also be added to the buffer and/or the sample. Moreover, maintenance of the sample at approximately 1° to 5° C., whilst contacting it with the antibody, may be preferred.

Obtaining a transcriptome for use in the methods of the present invention may be from a cell or tissue using methods well known to persons of ordinary skill in the art. Such methods may include, for example, polysome fractionation, poly(A) purification, exome capture, ribo-depletion, size fractionation, phenol-chloroform extraction, 70% ethanol elution, 100% ethanol elution, microRNA/small RNA isolation, or isolation of any RNA type. RNA transcripts of a transcriptome may also be obtained by coprecipitation/copurification with any protein, or with any complex, including ribosomal complexes. Thus, the methods of the present invention may be used to determine the base modification status of a transcriptome across an entire transcriptome group of RNA transcripts, or RNA transcripts of a particular RNA subtype, depending on which particular methods of obtaining the transcriptome are employed.

The methods of the present invention involve isolating, from the transcriptome, a pool of RNA transcripts to which the antibody binds. The pool of RNA transcripts may include full-length RNA transcripts or fragments of RNA derived from the full-length RNA transcripts. Thus, antibody-bound RNA transcripts can be separated from RNA transcripts to which no antibody is bound. Such isolating step can be carried out by various methods which are known by those of ordinary skill in the art.

According to one embodiment, isolating (or separating) is carried out by immunoprecipitation methods by attaching or binding an antibody to a solid phase or substrate (the terms are used interchangeably) and separating this solid phase from a sample liquid phase. Thus, addition of a solid substrate that binds specifically to an antibody facilitates the separation of an RNA transcript containing a modified base from an RNA transcript not having a modified base to which the antibody binds. Specific binding of the solid substrate to the antibody can be achieved by using a solid substrate that comprises a second antibody specific for the first antibody. For example, if the first antibody (i.e., the antibody specific to a modified base) is a mouse anti-m$^6$A antibody, a goat anti-mouse antibody would be suitable.

A solid substrate in the form of beads is particularly useful as this gives a large surface area over which binding can occur. Magnetic beads such as DYNABEADS (Dynal Biotech) or paramagnetic beads allow simple separation of modified and non-modified RNA transcripts as the beads (and, therefore, the nucleic acid bound to them) can be easily removed from a sample using a magnet. Other substrates, such as resin (e.g., agarose) or glass or other solid supports (e.g., ELISA plates) may also be used. Alternatively, the solid substrate could be separated from the non-bound nucleic acid using techniques such as centrifugation and/or filtration. A person of ordinary skill in the art can readily determine a suitable way to separate the solid substrate from non-bound (i.e. non-modified) RNA transcripts.

If desired, RNA can also be crosslinked to the antibody to facilitate RNA pulldown, which is common in the CLIP and PAR-CLIP type approaches. In some cases, the crosslinking is made more efficient if the RNA contains a nucleotide that has chemical modifications that enable it to crosslink to protein more efficiently.

In the methods of the present invention, RNA transcripts from the transcriptome may be fragmented before contacting the transcriptome with an antibody. Thus, the transcriptome that is contacted by the antibody may be a collection of RNA transcript fragments or full-length, and, therefore, the pool of RNA transcripts isolated from the transcriptome (as a result of antibody binding) would also constitute RNA transcript fragments.

Suitable RNA transcript fragments may include fragments having an average length of about 200 nucleotides, 150 nucleotides, 100 nucleotides, 50 nucleotides, 25 nucleotides, 10 nucleotides, or any combination thereof.

Fragmentation can be carried out by standard methods known in the art, e.g., sonication, chemical means such as hydrolysis, or enzyme digestion.

In carrying out the methods of the present invention, it may be desirable to sequence the RNA transcripts or RNA transcript fragments, both in the transcriptome and in the isolated pool. In one embodiment, sequencing of RNA transcripts is carried out by next-generation sequencing.

In addition, conventional nucleic acid analysis techniques may be applied to the RNA transcripts to perform additional analyses. For example, the presence of sequences of interest in the RNA transcripts may be determined using techniques such as PCR, slot blots, microarrays, etc., all of which are well known to those of ordinary skill in the art. According to one embodiment, a microchip system comprising a microarray of oligonucleotides or longer nucleotide sequences on a glass support is employed. Sample nucleic acid (e.g., fluorescently labelled) may be hybridized to the oligonucleotide array and sequence specific hybridization may be detected by scanning confocal microscopy and analyzed automatically (see Marshall & Hodgson, "DNA Chips: An Array of Possibilities," *Nature Biotechnology* 16:27-31 (1998); see also Schulze et al., "Navigating Gene Expression Using Microarrays—A Technology Review," *Nature Cell Biology* 3:E190-E195 (2001), each of which is hereby incorporated by reference in its entirety). A list of currently used techniques in microarray assembly and DNA detection can be found in the book *DNA Microarrays: A Molecular Cloning Manual*, eds. Bowtell and Sambrook, CSHL 2002.

Before sequencing and/or analyzing the isolated RNA transcripts, it may be desirable to detach the RNA molecule from the antibody (and any solid substrate used). Detaching methods for isolating RNA are known to persons of ordinary skill in the art. In carrying out detaching methods, care should be given to not damage the RNA transcript during the detaching process.

According to one embodiment, RNA transcripts are detached from antibodies by digesting the antibodies. This may be achieved by incubating the RNA transcript bound to the antibody with a proteinase such as Proteinase K. In addition, slightly altering the pH around the RNA transcript bound to the antibody may weaken the binding between the antibody and the RNA transcript, further facilitating detachment. This may be achieved by adding a suitable buffer (e.g., 50 mM Tris pH 8.0) to the RNA transcript and the antibody bound to it. EDTA (Ethylenediaminetetraacetic acid) and SDS (sodium dodecyl sulphate) may also be added to the buffer to assist in antibody detachment.

Figure 13:
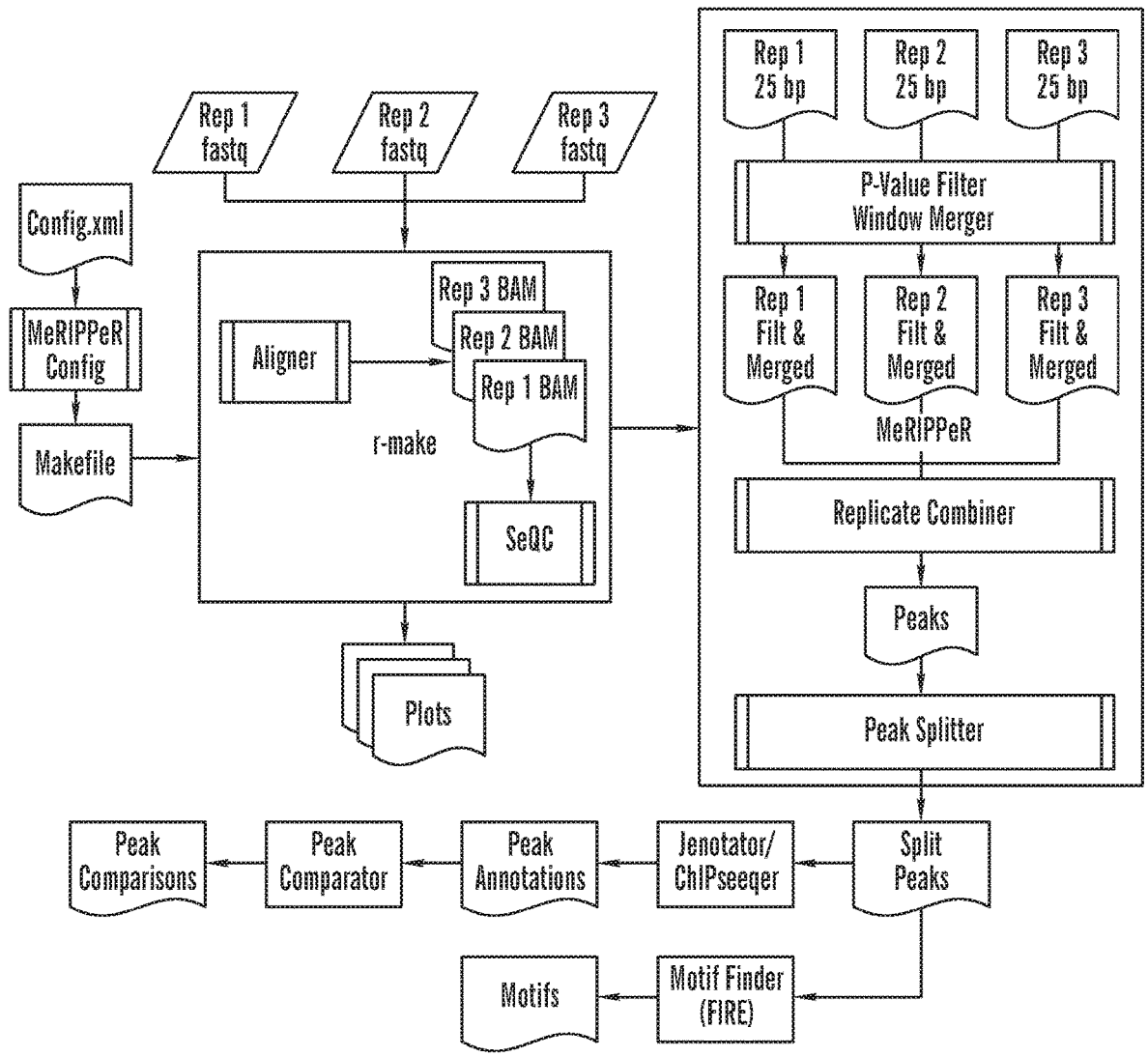
FIG. 13 is a flowchart showing a computational algorithm for analysis of RNA-IP data. Raw sequence data (fastq, top) is first taken and a gapped alignment of the reads to the genome is performed, which also estimates spliced and fragmented transcripts, a step called "r-make" that utilizes the parallelized and provenance-tracking tools (including the config.xml and .sh scripts) from UNIX's "make" but programmed to work with RNA data; hence, r-make. These alignments created sorted .bam files that store the alignment of the reads to the genome and transcriptome, which are then fed into the MeRIPPer algorithm, which carries out a window-based approach across the genome to find regions of 25 bp (this value is modular) that are significantly different using Fisher's Exact Test, using the IP'd sample vs. the control. These p-values are then corrected for multiple testing, merged, and peaks are called and ranked for significance and degree of change. If peaks are larger than the known fragment size, they are split into sub-peaks. These peaks may then be annotated, searched for motifs, or further analyzed by other tools like FIRE or Jenotator. These comparisons include the examination of peaks as they change in regards to sequence complexity, splicing level changes, gene expression change, peak location shift, peak intensity shift, motif change, or any other aspect of the sequences' changes, their effect on gene function, or interactions with other gene products.

Once they have been detached from the antibodies and the solid substrate and sequenced, the RNA transcripts/fragments are analyzed further to determine the relative abundance of the isolated RNA transcripts present in the isolated pool. Measuring the abundance of an isolated RNA transcript fragment is carried out using a computational algorithm (FIG. 13). The parameters of the computational algorithm can be adjusted to enable more/less stringent detection of modified base sites in RNA transcripts, and also as to whether or not the user wants to require the presence of a peak across all replicates. See Saletore et al., "The Birth of the Epitranscriptome: Deciphering the Function of RNA Modifications," *Genome Biology* 13:175 (2012), which is hereby incorporated by reference in its entirety. According to the methods of the present invention, isolated RNA transcripts that are present in a higher abundance in the isolated pool relative to the transcriptome are identified. Each of the isolated RNA transcripts that are present in a higher abundance in the isolated pool together characterize the modified base status of the transcriptome.

The modified base status of a transcriptome is also characterized by detecting clusters of modified base reads that form a peak using the algorithm described in FIG. 13 (see also Meyer et al., "Comprehensive Analysis of mRNA Methylation Reveals Enrichment in 3' UTRs and Near Stop Codons," *Cell* 149:1635-1646 (2012) and Dominissini et al, "Topology of the Human and Mouse m$^6$A RNA Methylomes Revealed by m$^6$A-seq," *Nature* 485:201-206 (2012), each of which is hereby incorporated by reference in its entirety). Generally, this involves the following steps: (1) taking raw sequence data; (2) performing a gap alignment of reads to the genome (r-make); (3) applying the MeRIPPeR algorithm to find regions that are significantly different; (4) calling and ranking peaks for significance and degree of change; and (5) annotating and analyzing the peaks. In all likelihood, these RNA fragments will be higher in relative abundance in the isolated pool than in the non-isolated pool (i.e., transcriptome), but the specific appearance of a "peak" is used to characterize the modified base status of the transcriptome.

Figure 12:
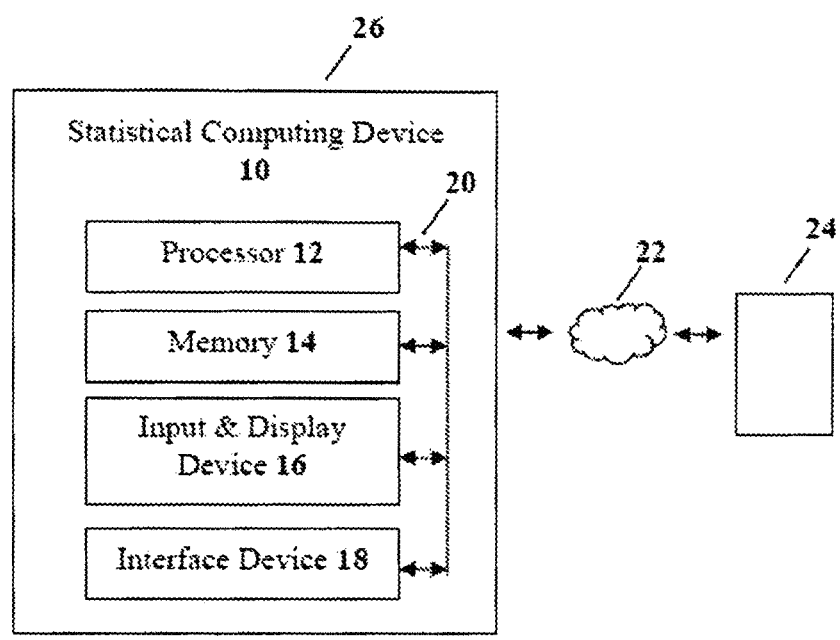
FIG. 12 is an exemplary environment comprising a statistical computing device for characterizing a transcriptome according to the presence of modified bases in the RNA transcripts contained in the transcriptome.

Application of the computational algorithm for measuring the abundance of an isolated RNA transcript fragment to characterize the modified base status of a transcriptome may be carried out with certain systems and devices. An exemplary environment 26 with a statistical computing device 10 that can be used to identify isolated RNA transcripts that are present in a higher abundance in the isolated pool relative to the transcriptome to characterize the modified base status of the transcriptome is illustrated in FIG. 12. The environment 26 includes statistical computing device 10, communication network 22 and database server 24, although the environment can include other types and numbers of devices, components, elements and communication networks in other topologies and deployments. This technology/process provides a number of advantages including providing more effective methods, non-transitory computer readable medium, and devices for characterizing the modified base status of a transcriptome.

The statistical computing device 10 assists with sequencing and quantifying the abundance of RNA transcripts, although the statistical computing device 10 may perform other types and numbers of functions. The statistical computing device 10 includes at least one processor 12, memory 14, input and display devices 16, and interface device 18 which are coupled together by a bus 20 or other link, although the statistical computing device 10 may comprise other types and numbers of elements in other configurations.

Processor(s) 12 may execute one or more computer-executable instructions stored in the memory 14 for the methods illustrated and described with reference to the examples herein, although the processor(s) can execute other types and numbers of instructions and perform other types and numbers of operations. The processor(s) 12 may comprise one or more central processing units ("CPUs") or general purpose processors with one or more processing cores, such as AMD® processor(s), although other types of processor(s) could be used (e.g., Intel®).

Memory 14 may comprise one or more tangible storage media, such as RAM, ROM, flash memory, CD-ROM, floppy disk, hard disk drive(s), solid state memory, DVD, or any other memory storage types or devices, including combinations thereof, which are known to those of ordinary skill in the art. Memory 14 may store one or more non-transitory computer-readable instructions of this technology as illustrated and described with reference to the examples herein that may be executed by the one or more processor(s) 12.

The flow shown in FIG. 13 is representative of example steps or actions of this technology that may be embodied or expressed as one or more non-transitory computer or machine readable instructions stored in memory 14 that may be executed by the processor(s) 12.

Input and display devices 16 enable a user, such as an administrator, to interact with statistical computing device 10, such as to input and/or view data and/or to configure, program, and/or operate it by way of example only. Input devices may include a keyboard and/or a computer mouse and display devices may include a computer monitor, although other types and numbers of input devices and display devices could be used.

The interface device 18 in the statistical computing device 10 is used to operatively couple and communicate between the statistical computing device 10 and the database server 24 which are coupled together by a communication network. The communication network 22 can be a local area network (LAN) and/or a wide area network (WAN), although other types and numbers of communication networks or systems with other types and numbers of connections and configurations to other devices and elements can also be used. By way of example only, the local area networks (LAN) and the wide area network (WAN) can use TCP/IP over Ethernet and industry-standard protocols, including NFS, CIFS, SOAP, XML, LDAP, and SNMP, although other types and numbers of communication networks, can be used. In this example, the bus 20 is a hyper-transport bus, although other bus types and links may be used, such as PCI.

The database server 24 processes requests received from the statistical computing device 10 via communication network 22 according to the HTTP-based application, RFC protocol, the CIFS or NFS protocol, or other application protocols. A series of applications may run on the database server 24 that allow the transmission of data, such as sequence data, requested by the statistical computing device 10. The patient database server 24 may provide data or receive data in response to requests directed toward the respective applications on the database server 24 from the statistical computing device 10. It is to be understood that the database server 24 may be hardware or software or may represent a system with multiple servers 16, which may include internal or external networks. In this example the patient database server 24 may be any version of Microsoft® IIS servers or Apache® servers, although other types of servers may be used.

Furthermore, each of the systems of the examples may be conveniently implemented using one or more general purpose computer systems, microprocessors, digital signal processors, and micro-controllers, programmed according to the teachings of the examples, as described and illustrated herein, and as will be appreciated by those of ordinary skill in the art.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including, by way of example only, teletraffic in any suitable form (e.g., voice and modem), wireless traffic media, wireless traffic networks, cellular traffic networks, G3 traffic networks, Public Switched Telephone Network (PSTNs), Packet Data Networks (PDNs), the Internet, intranets, and combinations thereof.

The examples may also be embodied as a non-transitory computer readable medium having instructions stored thereon for one or more aspects of the technology as described and illustrated by way of the examples herein, which when executed by a processor (or configurable hardware), cause the processor to carry out the steps necessary to implement the methods of the examples, as described and illustrated herein.

As used herein, "characterizing the modified base status of a transcriptome" means whether and/or to what extent the RNA transcripts of the transcriptome, as identified by the isolated RNA transcripts in the isolated pool, contain modified bases. Thus, the transcriptome is characterized by which bases of its RNA transcripts are modified, as well as the proportion of bases in the transcriptome that are modified.

The methods of the present invention provide the ability to perform high-resolution mapping of individual modified base sites in RNA. To this end, a variety of techniques related to the mapping of protein-RNA interactions could be employed, such as RIP-Seq or CLIP-Seq. Increased fragmentation of RNA may be performed prior to both (i) contacting the transcriptome with an antibody and (ii) isolating antibody bound transcript fragments, RNase digestion could be employed following antibody/RNA binding to decrease the size of immunoprecipitated RNA transcript fragments, and/or UV-crosslinking of antibody/RNA transcript fragment complexes and detection of polymerase stalls/mutations induced by antibody-RNA adducts could all be used to map individual modified base sites.

The methods of the present invention can also be utilized to determine the regulatory interaction of modified base sites with transcription factors and protein cofactors in vivo and within in vitro systems. For example, it may be desirable to determine the specific proteins and factors that influence the levels of modified bases on a particular transcript, and the method of the present invention can be utilized to target such proteins. In addition, the method of the present invention can be used to determine the effect of modified base levels and cellular machinery for the metabolism and use-rate of modified bases in a cell or in vitro systems.

In one embodiment, characterization of the transcriptome is based on the presence of substituted bases. In another embodiment, characterization of the transcriptome is based on the presence of a methylated base, such as $m^6A$, or any other modified (whether methylated or not) base, as described herein. In yet another embodiment, characterization of the transcriptome is based on the presence of both substituted and methylated bases.

In one embodiment, the methods of the present invention are employed to establish how modified base residues are distributed in the transcriptome of various types of cells. Thus, transcriptomes that may be used in the methods of the present invention include those obtained from a single cell type, a single tissue type, a diseased cell or tissue, or a non-diseased cell or tissue. Thus, for example, the transcriptome may be from a cancer biopsy or a blood sample so that the modified base status of a transcriptome from such a cell type may be characterized.

In another embodiment, the modified base status of a transcriptome from a first cell type or tissue type is compared to the modified base status of a transcriptome from a second cell type or tissue type. By comparing the modified base status of one transcriptome obtained from cell or tissue type to another cell or tissue type, it may be possible to determine if a particular biological sample has base modifications that are compatible with a specific disease. Also, such a method could be useful in determining the causes and/or effects of modified bases of a transcriptome. For example, in one embodiment, the first cell type or tissue type is from a non-diseased cell or tissue and the second cell type or tissue type is from a diseased cell or tissue. According to this particular embodiment, the modified base status of a diseased cell or tissue can be compared to the modified base status of a non-diseased cell or tissue to decipher the effect the modified base status of the transcriptome has on a particular disease state.

In another embodiment, the method of the present invention is carried out to determine how a modified base status of a transcriptome from one cell or tissue type is different from one disease state to another, thereby establishing etiology of a disease or biomarkers for disease states.

For example, the fat mass and obesity-associated (FTO) gene is a major regulator of metabolism and energy utilization (Church et al., "A Mouse Model for the Metabolic Effects of the Human Fat Mass and Obesity Associated FTO Gene," *PLoS Genet* 5:e1000599 (2009); Church et al., "Overexpression of Fto Leads to Increased Food Intake and Results in Obesity," *Nat. Genet* 42:1086-1092 (2010); Fischer et al., "Inactivation of the Fto Gene Protects From Obesity," *Nature* 458:894-898 (2009), each of which is hereby incorporated by reference in its entirety). In humans, FTO polymorphisms that increase FTO expression are associated with elevated body mass index and increased risk for obesity (Fawcett et al., "The Genetics of Obesity: FTO Leads the Way," *Trends Genet.* 26:266-274 (2010), which is hereby incorporated by reference in its entirety). FTO is a member of the Fe(II)- and oxoglutarate-dependent AlkB oxygenase family, and was originally shown to catalyze the oxidative demethylation of methylated thymidine and uracil (Gerken et al., "The Obesity-Associated FTO Gene Encodes a 2-Oxoglutarate-Dependent Nucleic Acid Demethylase," *Science* 318:1469-1472 (2007); Jia et al., "Oxidative Demethylation of 3-Methylthymine and 3-Methyluracil in Single-Stranded DNA and RNA by Mouse and Human FTO," *FEBS Lett.* 582:3313-3319 (2008), each of which is hereby incorporated by reference in its entirety). However, FTO exhibits low activity toward these base modifications, and they are relatively infrequent with unclear physiological relevance (Klagsbrun, M., "An Evolutionary Study of the Methylation of Transfer and Ribosomal Ribonucleic Acid in Prokaryote and Eukaryote Organisms," *J. Biol. Chem.* 248:2612-2620 (1973), which is hereby incorporated by reference in its entirety). Thus, the physiologically relevant targets of FTO was unclear until recent studies that showed that FTO can demethylate the naturally occurring adenosine modification $N^6$-methyladenosine (Jia et al., "N6-Methyladenosine in Nuclear RNA Is a Major Substrate of the Obesity-Associated FTO," *Nat. Chem. Biol.* 7(12):885-887 (2011) and Meyer et al., "Comprehensive Analysis of mRNA Methylation Reveals Enrichment in 3' UTRs and Near Stop Codons," *Cell* 149:1635-1646 (2012), each of which is hereby incorporated by reference in its entirety). These studies link adenosine methylation to physiological roles in human biological processes.

In another example, Zheng et al., "ALKBH5 Is a Mammalian RNA Demthylase that Impacts RNA Metabolism and Mouse Fertility," *Mol. Cell* 49:1-12 (2013), which is hereby incorporated by reference in its entirety, describes a demethylase that oxidatively reverses $m^6A$ modification, and this reversible modification was shown to have a fundamental and broad function in mammalian cells.

Transcriptomes may also be obtained from experimentally treated cells, such as cancer cells treated with a test compound. By comparing the modified base status of a transcriptome from a treated sample to a non-treated sample, researchers could determine the affect of a test compound on the modified base status in a transcriptome and/or at a specific site within a specific RNA transcript. Thus, this method of the present invention may be useful in drug discovery. Recently, Chen et al., "Development of Cell-Active $N^6$-Methyladenosine RNA Demethylase FTO Inhibitor," *J. Am. Chem. Soc.* 134:17963-17971 (2012), which is hereby incorporated by reference in its entirety, described small-molecule inhibitors of human FTO demethylase that exhibit good inhibitory activity on $m^6A$ demethylation inside cells.

In another embodiment, the transcriptome may be obtained from genetically modified cells, such as cells that are expressing either a control construct or a construct that expresses a target gene of interest or a knockdown construct. By comparing the modified base status of a transcriptome from such a sample, it may be possible to determine whether a gene can be used to normalize modified base levels, or if a gene has a role in regulating modified base levels.

In a further embodiment, the transcriptome is obtained from stem cells, such as embryonic stem cells, differentiated stem cells, or induced pluripotent stem (IPS) cells. By comparing the modified base profiles from transcriptomes from such cell types, it may be possible to determine whether changes in modified base levels accompany cellular differentiation which is important for cell fate decisions and embryonic development.

Another aspect of the present invention relates to a method of diagnosis or prognosis of a disease or disorder associated with a modified base in RNA in a subject. This method involves obtaining a transcriptome from a subject, where the transcriptome comprises one or more modified bases; characterizing the modified base status of the transcriptome; and comparing the modified base status of the transcriptome to a known modified base status of a comparable transcriptome from a healthy and/or diseased subject to provide a diagnosis or prognosis of a disease or disorder in the subject.

In one embodiment, obtaining a transcriptome from a subject involves obtaining a sample of RNA. In another embodiment, obtaining a transcriptome from a subject involves obtaining a complete transcriptome from a subject.

A further aspect of the present invention relates to a method of determining the effect of a treatment on modified base levels of a transcriptome from a subject. This method involves characterizing the modified base status of a transcriptome comprising one or more modified bases from a subject before a treatment is administered to the subject; characterizing the modified base status of the transcriptome from the subject after a treatment is administered to the subject; and comparing the modified base status of the transcriptome after said treatment to the modified base status of the transcriptome before said treatment to determine the effect of the treatment on modified base levels of the transcriptome in the subject.

In carrying out these methods of the present invention, characterizing the modified base status involves contacting the transcriptome with an antibody specific to the one or more modified bases under conditions effective to bind the antibody to the one or more modified bases; isolating, from the transcriptome, a pool of RNA transcripts to which the antibody binds; and identifying isolated RNA transcripts that are present in a higher abundance in the isolated pool relative to the transcriptome, where each of said isolated RNA transcripts that are present in a higher abundance in the isolated pool together characterize the modified base status of the transcriptome.

In one embodiment, characterizing the modified base status of the transcriptome may involve isolating and purifying cells or tissues from the subject using standard techniques, and then characterizing the modified base status of the transcriptome from that cell or tissue.

According to one embodiment, modified base status may be detected in just one transcript, or group of transcripts, rather than the entire transcriptome.

The present invention also relates to a kit for characterizing the modified base status of a transcriptome. The kit includes an antibody that binds a modified base in RNA; one or more buffer solutions for carrying out antibody binding to a modified base in RNA, isolation of antibody-bound RNA, and/or sequencing of RNA molecules; and a computer-readable medium having stored thereon computer-readable instructions for comparing the abundance of an RNA transcript fragment in an isolated pool of RNA transcripts from a transcriptome to the abundance of that RNA transcript in the transcriptome prior to isolation thereof to identify isolated RNA transcripts that are present in a higher abundance in the isolated pool relative to the transcriptome, where each of said isolated RNA transcripts that are present in a higher abundance in the isolated pool together characterize the modified base status of the transcriptome.

The antibody and buffer solution components of the kit may be packaged either in aqueous media or in lyophilized form. The container means of the kit will generally include at least one vial, test tube, flask, bottle, syringe or other container means, into which a component may be placed, and preferably, suitably aliquoted. The kit also will generally contain a second, third or other additional container into which the additional components may be separately placed. However, various combinations of components may be comprised in a vial. The kits of the present invention also will typically include a means for containing the antibodies, and any other reagent containers in close confinement for commercial sale.

When the components of the kit are provided in one and/or more liquid solutions, the liquid solution is an aqueous solution, with a sterile aqueous solution being one preferred solution. Other solutions that may be included in the kit are those solutions involved in carrying out antibody binding to a modified base in RNA, isolation of antibody-bound RNA, sequencing of RNA molecules, separation of antibodies from bound RNA, and any other solutions needed in carrying out the methods of the present invention described herein.

The kit can also include instructions for employing the kit components, the use of any other reagent not included in the kit, and use or programming of the computer-readable medium. Preferably, the kit includes instructions for using the antibody that binds a modified base in RNA, necessary buffer solutions for carrying out methods of the present invention described herein, and a computer-readable medium having stored thereon instructions for comparing the abundance of an RNA transcript fragment in an isolated pool of RNA transcripts from a transcriptome to the abundance of that RNA transcript in the transcriptome prior to isolation thereof to identify isolated RNA transcripts that are present in higher abundance in the isolated pool relative to the transcriptome, where each of said isolated RNA transcripts that are present in a higher abundance in the isolated pool together characterize the modified base status of the transcriptome. Instructions may include variations that can be implemented.

These aspects of the present invention are further illustrated by the examples below.

EXAMPLES

The following examples are provided to illustrate embodiments of the present invention, but they are by no means intended to limit its scope.

Materials and Methods for Examples 1-13

$m^6A$ Immunoprecipitation/RNA-Seq (MeRIP-Seq)—

Total mouse brain RNA was subjected to RiboMinus treatment to reduce rRNA content as per the manufacturer's instructions (Invitrogen). RNA was then fragmented to 100 nt-sized fragments using Illumina Fragmentation Buffer according to the manufacturer's instructions, and subjected to two rounds of $m^6A$ immunoprecipitation. Sequencing libraries were prepared using the Illumina protocol for mRNA samples, and sequencing was performed on an Illumina GAIIx or an Illumina HiSeq2000 as indicated. Genomic alignment (mm9 from UCSC genome browser) was done using the Burrows-Wheeler Aligner (BWA) (Li et al., "Fast and Accurate Long-read Alignment with Burrows-Wheeler Transform," *Bioinformatics* 26:589-595 (2010), which is hereby incorporated by reference in its entirety) at default settings. Only those reads which (1) uniquely mapped to the genome and (2) had a Phred quality score greater or equal to 20 were analyzed.

Accession Numbers—

MeRIP-Seq data have been deposited in the GEO database under accession number GSE29714.

RNA Isolation—

Adult C57BL/6 mice (age 6-16 weeks) were sacrificed by $CO_2$ inhalation and cervical dislocation in accordance with the Weill Cornell Medical College Institutional Animal Care and Use Committee (IACUC). RNA from various tissues was immediately isolated using TRIZOL according to the manufacturer's instructions (Invitrogen). For isolation of embryonic rat brain RNA, timed-pregnant female dams were sacrificed by $CO_2$ inhalation and cervical dislocation, and embryos were immediately removed and their brains isolated for RNA collection. Postnatal and adult rats were sacrificed as described for adult mice. HEK293T cell RNA was isolated from 10 cm dishes of HEK293T cells using TRIZOL as above. For isolation of poly(A) RNA, total mouse brain RNA was subjected to two rounds of purification using oligo(dT)-coupled magnetic beads according to the manufacturer's instructions (Invitrogen). The uncaptured RNA after two rounds was designated as the "unhybridized RNA." Lastly, for MeRIP-Seq experiments, total RNA was isolated as above and subjected to RiboMinus treatment (Invitrogen) prior to immunoprecipitation. Notably, although these samples likely contain more mature, spliced mRNA than pre-mRNA, it was observed that the percentage of intronic reads in the input RNA samples is consistent with that of rRNA-depleted samples (51% of total intronic and exonic sequences were introns), indicating that intronic sequences are indeed present within the input RNA.

Antibodies—

Two independently-derived antibodies generated against $m^6A$ were used in these studies. One is a rabbit polyclonal antibody originally developed by a research group in Germany (Munns et al., "Characterization of Antibodies Specific for N6-Methyladenosine and for 7-Methylguanosine," *Biochemistry* 16:2163-2168 (1977), which is hereby incorporated by reference) and now commercially available through Synaptic Systems (SySy; Germany). The other is a separate rabbit polyclonal antibody of independent origin which was developed by a research group at New England Biolabs (NEB) (Kong et al., "Functional Analysis of Putative Restriction-Modification System Genes in the *Helicobacter pylori* J99 Genome," *Nucleic Acids Res.* 28:3216-3223 (2000), which is hereby incorporated by reference in its entirety).

Cell Culture—

Cortical neurons were isolated from embryonic day 18 (E18) or postnatal day 3 (P3) rats and cultured according to established methods (Cohen et al., "Neurotrophin-Mediated Dendrite-to-Nucleus Signaling Revealed by Microfluidic Compartmentalization of Dendrites," *Proc. Natl. Acad. Sci. U.S.A.* 108: 11246-11251 (2011), which is hereby incorporated by reference in its entirety). Briefly, cells were plated in Culture Media (Neurobasal supplemented with 1% penicillin/streptomycin, 1% Glutamax, and 2% NS21) (Chen et al., "NS21: Re-Defined and Modified Supplement B27 for Neuronal Cultures," *J. Neurosci. Methods* 171:239-247 (2008), which is hereby incorporated by reference in its entirety). After 3 DIV, half the media was replaced with Culture Media+20 μM 5'-fluoro-2'-deoxyuridine (FdU) to eliminate dividing glial cells and obtain neuron-enriched cultures, and on every third day thereafter, one-third of the media was replaced with fresh Culture Media. Neurons were grown for 8-10 DIV and RNA isolated as described above. Immortalized cell lines were cultured in appropriate media (American Type Culture Collection; ATCC) and RNA was isolated as described above.

FTO Overexpression—

Overexpression experiments were carried out by infecting HEK293T cells with FLAG-tagged human FTO lentivirus or no virus control. Cells were cultured for 48 hours, and total RNA was isolated using TRIZOL as above and then subjected to $m^6A$ immunoblotting. Additionally, heterologous overexpression of Flag-tagged human METTL3 was carried out in HEK293T cells using LIPOFECTAMINE 2000 according to the manufacturer's instructions (Invitrogen). RNA was isolated after 24 or 48 hours as above; however, increases in $m^6A$ levels detected by $m^6A$ immunoblotting were inconsistent.

$m^6A$ Immunoblotting—

RNA samples were quantified using UV spectrophotometry, and equal amounts were mixed 1:1 with glyoxal loading dye (Ambion) and denatured for 20 minutes at 50° C. Samples were then run on a 1% agarose gel for 1 hour at 70 V and transferred to a nylon membrane for 2-3 hours using the NORTHERNMAX-Gly kit according to the manufacturer's instructions (Ambion). RNA was UV crosslinked to the membrane, and membranes were blocked for 1 hour in 5% nonfat dry milk in 0.1% PBST (0.1% Tween-20® in 1×PBS, pH 7.4) (Blocking Buffer). Rabbit anti-$m^6A$ antibody (SySy or NEB) or was diluted 1:1000 in 0.1% PBST and incubated on the membranes for 1 hour (25° C.) to overnight (4° C.). Following extensive washing with 0.1% PBST, HRP-conjugated donkey anti-rabbit IgG (GE Healthcare) was diluted 1:2500 in Blocking Buffer and added to the membranes for 1 hour at 25° C. Membranes were washed again in 0.1% PBST and developed with enhanced chemiluminescence (ECL; GE Healthcare).

Dot Blot Assays—

Dot blots were performed essentially as described for $m^6A$ immunoblotting (above). Two 25 nt-long oligonucleotides (Midland) were designed to contain either $m^6A$ or A at a single internal position (5' AGTCGTTCATCT AGTTGCGGTGTAC 3' (SEQ ID NO:1)) and were spotted onto a nylon membrane (GE Healthcare). The membrane was then UV crosslinked, blocked, and exposed to rabbit anti-$m^6A$ antibody as described above. For competition assays, rabbit anti-$m^6A$ antibody was pre-mixed with competitor RNA or competitor NTP for 30 minutes at 25° C. Competitor NTPs used were: $N^6$-methyladenosine triphosphate, adenosine triphosphate, $N^1$-methyladenosine triphosphate, and 2'-O-methyladenosine triphosphate (TriLink). For experiments using competitor RNA, a PCR product was amplified from rat brain cDNA using the following primers:

```
                                        (SEQ ID NO: 2)
5' TAATACGACTCACTATAGGGTGTCACCAACTGGGA 3' Fwd
(T7 promoter sequence is italicized)
and
                                        (SEQ ID NO: 3)
5' ACCCTCATAGATGGGCACAG 3' Rev.
```

RNA was in vitro transcribed from this PCR product using the AmpliScribe T7-Flash kit (Epicentre). NTPs were added individually to the in vitro transcription reaction and included GTP, CTP, UTP and either $N^6$-methyladenosine triphosphate ($N^6$-MeATP) or adenosine triphosphate (ATP). Following pre-incubation with competitor NTPs or RNA, the $m^6A$ antibody was incubated on the membranes for 1 hour at 25° C. Membranes were then washed in 0.1% PBST, followed by incubation in secondary antibody (HRP-conjugated donkey anti-rabbit IgG, diluted 1:2500 in block) for 1 hour at 25° C. Membranes were again washed in 0.1% PBST and developed with ECL.

$m^6A$ DNA Immunoblotting—

Cells from dam+ (DH5alpha; Invitrogen) or dam− (K12 ER2925; New England Biolabs) *E. coli* strains were grown overnight at 37° C. in 5 ml cultures of Luria-Bertani (LB) broth. Genomic DNA was isolated from each cell line and randomly sheared using a Branson sonicator (5 rounds of 7 sec pulses at 20% amplitude with 1 sec intervals). DNA was then treated with RNase A for 30 minutes at 37° C. to remove any RNA and quantified with UV spectrophotometry. 1 μg of dam+ DNA and 1.5 μg of dam− DNA were loaded into a 1% agarose gel and electrophoresed for 40 minutes at 100 V. DNA was passively transferred to a nylon membrane (GE Healthcare) for ~2 hours with 20×SSC. Membrane was then UV crosslinked and blotted with anti-$m^6A$ as described above.

Densitometry—

Densitometry analysis of the relative abundance of $m^6A$ in immunoblot experiments was performed using the ImageJ software (Abramoff et al., "Image Processing with ImageJ," *Biophotonics International* 11:36-42 (2004), which is hereby incorporated by reference in its entirety). The levels of $m^6A$ across various samples were determined relative to the levels of ethidium bromide staining of the corresponding 28S rRNA band (images of 28S rRNA band intensity were acquired prior to transferring the RNA from the gel to the membrane during immunoblotting).

$m^6A$ Immunoprecipitation—

For immunoprecipitation of RNA for MeRIP-Seq experiments, 12 μl rabbit anti-$m^6A$ antibody (Synaptic Systems or New England Biolabs) was coupled to sheep anti-rabbit DYNABEADS (Invitrogen) in 300 μl 1 M IP Buffer (1 M NaCl, 10 mM sodium phosphate, 0.05% TRITON-X) for 2 hours at 4° C. Beads were then washed 3 times in 300 μl 140 mM IP Buffer (140 mM NaCl, 10 mM sodium phosphate, 0.05% TRITON-X). Fragmented RNA was denatured 5 minutes at 75° C., cooled on ice 2-3 minutes, and bound to antibody-coupled beads in 300 μl of 140 mM IP Buffer (2 hours at 4° C.). Beads were treated with 300 μl Elution Buffer (5 mM Tris-HCL pH 7.5, 1 mM EDTA pH 8.0, 0.05% SDS, 4.2 μl Proteinase K (20 mg/ml)) for 1.5 hours at 50° C., and RNA was recovered with phenol:chloroform extraction followed by ethanol precipitation.

To demonstrate the ability of the $m^6A$ antibody to immunoprecipitate targets that contain $m^6A$, in vitro immunoprecipitation experiments were performed. $m^6A$-containing DNA or RNA of known sequence was mixed with unmethylated DNA to achieve a heterogeneous population of both methylated and unmethylated targets, analogous to the mixture of both methylated and unmethylated RNA fragments that are used in MeRIP-Seq. The source of unmethylated DNA was a PCR product generated from rat brain cDNA using the following primers targeting β-actin:

```
                                    (SEQ ID NO: 4)
    5' TGTCACCAACTGGGACGATA 3' Fwd
and (SEQ ID NO: 5)
    5' ACCCTCATAGATGGGCACAG 3' Rev.
```

The source of methylated DNA was a 3 kb fragment of the pcDNA3.1 vector (Invitrogen) obtained by restriction enzyme digest with PvuII. The digested vector was grown in dam+ cells (DH5alpha, Invitrogen), and the presence of $m^6A$ was confirmed with dam−sensitive restriction enzyme digest. For experiments using methylated RNA as a source of $m^6A$, total mouse brain RNA was used in the input sample. For all assays, unmethylated DNA and methylated DNA/RNA were mixed 1:1 and used as the input sample. Immunoprecipitation using the $m^6A$ antibody was performed as described for MeRIP-Seq (above), and $m^6A$ target enrichment was measured with real-time quantitative PCR (qPCR; see below). For experiments using RNA as the source of $m^6A$, cDNA was generated from both input and immunoprecipitated samples using random hexamers and SUPERSCRIPT III reverse transcriptase according to the manufacturer's instructions (Invitrogen) and then subjected to real-time qPCR analysis. For control experiments, MeRIP was performed using rabbit IgG in place of the $m^6A$ antibody. All other experimental parameters were kept the same.

Real-Time Quantitative PCR—

Real-time qPCR reactions were performed using iQ SYBR Green Supermix (Bio-Rad) and an EPPENDORF MASTERCYCLER ep realplex thermocycler. The ratio of methylated DNA (pcDNA3.1 or U2snRNA cDNA) to unmethylated DNA (β-actin) was determined for each sample, and enrichment for $m^6A$ targets was calculated relative to the input sample. All samples were run in duplicate. Primers used to amplify each target are as follows:

```
β-actin:
                                    (SEQ ID NO: 6)
    5' TGTCACCAACTGGGACGATA 3' Fwd
and (SEQ ID NO: 7)
    5' ACCCTCATAGATGGGCACAG 3' Rev;

pcDNA3.1:
                                    (SEQ ID NO: 8)
    5' TGTAGGCGGTGCTACAGAGTTCTT 3' Fwd
and (SEQ ID NO: 9)
    5' TTTCTGCGCGTAATCTGCTGCTTG 3' Rev;

U2 snRNA:
                                    (SEQ ID NO: 10)
    5' GGCCTTTTGGCTAAGATCAAGTGT 3' Fwd
and (SEQ ID NO: 11)
    5' GGACGGAGCAAGCTCCTATTCCAA 3' Rev;

Rps14:
                                    (SEQ ID NO: 12)
    5' ACCTGGAGCCCAGTCAGCCC 3' Fwd
and (SEQ ID NO: 13)
    5' CACAGACGGCGACCACGACG 3' Rev;

Rps21:
                                    (SEQ ID NO: 14)
    5' CTGCGGAGGCACGAGCTACT 3' Fwd
and (SEQ ID NO: 15)
    5' TTCCGCGGCACGTACAGGTC 3' Rev;

Ndel1:
                                    (SEQ ID NO: 16)
    5' TGTCACCAACTGGGACGATA 3' Fwd
and (SEQ ID NO: 17)
    5' ACCCTCATAGATGGGCACAG 3' Rev;

Ptpn4:
                                    (SEQ ID NO: 18)
    5' CCTCCCATCCCGGTCTCCACC 3' Fwd
and (SEQ ID NO: 19)
    5' GGCTGCCCATCTTCAGGGGT 3' Rev;

Grm1:
                                    (SEQ ID NO: 20)
    5' GCCTCAGTGTGACGGTGGCC 3' Fwd
and (SEQ ID NO: 21)
    5' AGCTTGCCGTCACCGACGTG 3' Rev;

Drd1a:
                                    (SEQ ID NO: 22)
    5' TGTGTGGTTTGGCTGGGCGA 3' Fwd
and (SEQ ID NO: 23)
    5' TGGAGATGGAGCCTCGGGGC 3' Rev;

Tlr3:
                                    (SEQ ID NO: 24)
    5' TGCTCAGGAGGGTGGCCCTT 3' Fwd
and (SEQ ID NO: 25)
    5' CGGGGTTTGCGCGTTTCCAG 3' Rev.
```

3' Rapid Amplification of cDNA Ends (RACE)—

RACE-ready cDNA was generated from equal amounts of total poly(A) RNA, poly(A) tail-depleted RNA, or poly(A) tail-only RNA using a 1:1 ratio of the GeneRacer oligo(dT) primer (Invitrogen) and random hexamers according to the manufacturer's instructions (Invitrogen). PCR was carried out using PHUSION High-Fidelity PCR Master Mix (Finnzymes).

RNA Pull-Down—

In experiments designed to validate the presence of $m^6A$ in specific transcripts, RNAs were selectively pulled down using biotinylated (attached at the 3' or 5' end) DNA probes. These probes were 50 nt in length, and were complementary to target mRNAs. The probes (300 pg) were mixed with 10 µg total mouse brain RNA in 50 µl total volume of hybridization buffer (2×SSC, 40 U/ml RNaseOUT, 300 ng/ml salmon sperm DNA). Samples were denatured 3 minutes at 75° C. and hybridized 30 minutes at 37° C. with occasional mixing. Meanwhile, 100 µl of MyOne T1 streptavidin-coupled DYNABEADS (Invitrogen) were equilibrated by washing twice in 100 µl Binding/Washing (B&W) Buffer (5 mM Tris-HCl, 0.5 mM EDTA, 1 M NaCl), once in 0.1 M NaOH, and once in 0.1 M NaCl. Beads were then resuspended in 100 µl B&W Buffer+1 µg yeast tRNA (Roche) and incubated at room temperature for approximately 15 minutes. Buffer was then replaced with 50 µl B&W Buffer, and beads were added to the probe/RNA hybridization mix and incubated 10 minutes at room temperature with gentle rotation. Following 3 washes in B&W Buffer, 1 wash each in 0.5×SDS, 1×SSC, and 0.2×SSC, beads were resuspended in 100 µl Elution Buffer (10 mM EDTA, pH 8.0, 95% formamide), and biotinylated probe:RNA complexes were eluted by heating for 2 minutes at 90° C. Eluate was then digested with RNase H for 20 minutes at 37° C. and ethanol precipitated.

Unique Properties of MeRIP-Seq Data—

Although MeRIP-Seq is conceptually similar to CLIP-Seq, there are important technical differences between the two methods which necessitate the use of unique strategies for analyzing MeRIP-Seq data. In CLIP-Seq, endogenous RNA binding protein (RBP)-RNA interactions are stabilized by UV crosslinking and then partially digested with ribonucleases, leaving a unique "footprint" of RNA that is protected from digestion by the presence of the bound protein. The protein of interest is then immunoprecipitated (along with any bound RNAs). These RNA-RBP complexes are then end-labeled, separated by SDS-PAGE, and transferred to nitrocellulose. The short RNA fragments, or "tags," are then isolated in accordance with the predicted size of the RBP, allowing them to be separated from any non-RBP bound RNA. Finally, these short RNA tags are then subjected to high-throughput sequencing, and the location of RBP binding sites can be determined by identifying regions of the transcriptome that contain unique overlapping tags (Ule et al., "CLIP: A Method for Identifying Protein-RNA Interaction Sites in Living Cells," *Methods* 37:376-386 (2005), which is hereby incorporated by reference in its entirety). MeRIP-Seq, however, seeks to identify the location of a unique methylated base throughout the transcriptome. Instead of immunoprecipitating full-length RNA directly and then digesting it to produce protected fragments (as in CLIP-Seq), MeRIP-Seq digests the RNA first, then immunoprecipitates $m^6A$-containing RNA fragments with an antibody that recognizes $m^6A$. These fragments are then subjected to high-throughput sequencing, and are analogous to the tags sequenced in CLIP-Seq studies. The method for RNA fragmentation in MeRIP-Seq follows the recommendations of the sequencing platform used (Illumina) and digests RNAs to a range of sizes approximately 100 nt long. Therefore, one or more $m^6A$ residues could lie within each 100 nt-long tag that is sequenced. In contrast, CLIP-Seq tags are defined by the small regions in RNA that are protected from digestion by a bound RBP and thus identify a narrow region of RNA in which a given RBP binds.

This difference in the way CLIP-Seq and MeRIP-Seq tags are generated is important, because it translates to the use of different methods for identifying areas of CLIP-Seq and MeRIP-Seq tag clustering throughout the transcriptome. Both techniques are susceptible to non-specific immunoprecipitation of RNA, which can occur when RNA is binds to beads or other surfaces used in immunoprecipitation protocols. These non-specifically bound RNAs are presumably degraded by the ribonuclease digestion step in CLIP-Seq and are further excluded following the SDS-PAGE and subsequent size selection steps. However, such a step does not exist in the MeRIP-Seq protocol, as the addition of ribonucleases would lead to the degradation of $m^6A$-containing RNAs as well. Thus, MeRIP-Seq data requires the pool of RNA prior to $m^6A$ immunoprecipitation to be sequenced in parallel. This population of RNA provides a measure of the abundance of each individual transcript prior to immunoprecipitation; thus, a comparison of tags from $m^6A$ immunoprecipitation (the MeRIP sample) to those from RNA prior to immunoprecipitation (the non-IP sample) is necessary to distinguish the MeRIP tags that are significantly enriched due to recognition by the $m^6A$ antibody from those that are randomly immunoprecipitated. In addition, because MeRIP-Seq seeks to uncover information regarding the frequency of adenosine methylation (see below), it is necessary to take into account the abundance of individual transcripts prior to immunoprecipitation. Because $m^6A$ immunoprecipitation enriches for $m^6A$-containing transcripts, and thus changes the abundance of individual RNA fragments in the MeRIP sample, analyzing non-IP sample tags is necessary to determine the abundance of individual transcripts.

Identification of $m^6A$ Peaks Genome-Wide—

In order to identify regions that contain $m^6A$, a method for detecting MeRIP-Seq read peaks was developed according to their genomic annotations. To do this, the entire genome (mm9 and hg19 builds) was divided into 25 nt-wide discrete, non-overlapping windows and the number of reads in the MeRIP sample were compared to the number of reads in the non-IP (control) sample. Since the non-IP sample was generated from the same initial pool of RNA as the MeRIP sample, it serves as a measure of the abundance of individual transcripts that were in the MeRIP sample prior to immunoprecipitation. Thus, by comparing the number of reads in the MeRIP sample to those in the non-IP sample, any biases that might be caused by non-random fragmentation of the RNA or by variability in the abundance of individual transcripts were minimized.

The number of reads that mapped to a given window for the MeRIP sample and the non-IP sample were compared to the total number of reads in each, and Fisher's exact test was used to determine the probability of observing this under the null hypothesis for each window (the p-value). Fisher's exact test is non-parametric and makes no assumptions about the model underlying the data. To account for the multiple testing hypothesis with such a large number of independent statistical tests (i.e., the large number of individual windows), Benjamin-Hochberg was used to adjust the p-values to reduce the false discovery rate to 5%. A window was defined as significant when the adjusted p-value was ≤0.05 for each replicate. Then, Fisher's Method was used to combine p-values across replicates to calculate a final p-value for the window. This strategy made it possible to identify regions of MeRIP read clusters at high resolution (25 nt), while simultaneously filtering out those windows that reach significance by chance, because of artifacts in the data or because of sequencing errors. The present analysis revealed 93,074 significant 25 bp windows for all three replicates in the mouse tissue samples and 440,910 in the HEK293T tissue samples.

Figure 4A:
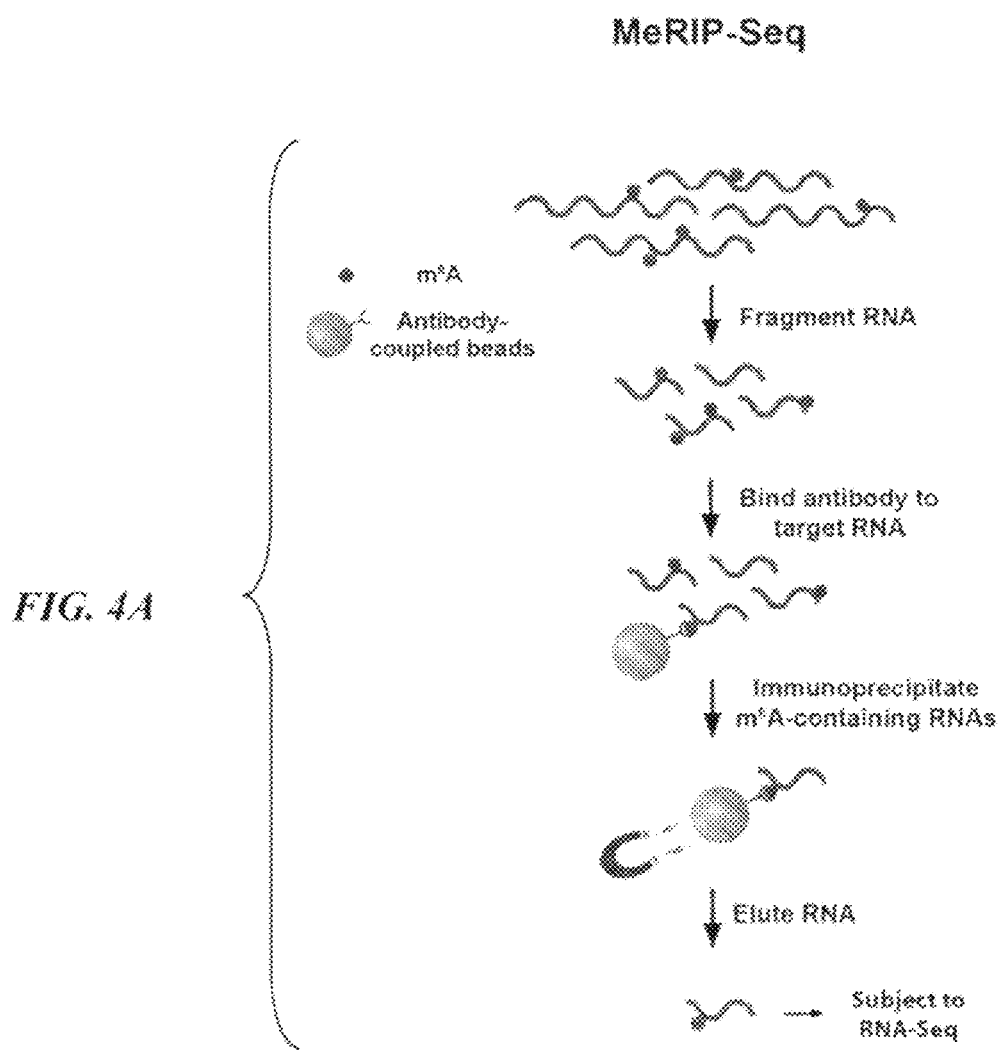
FIGS. 4A-4C show an outline of m⁶A immunoprecipitation/RNA-Seq (MeRIP-Seq) protocol and distribution of sequencing reads.
Figure 4B:
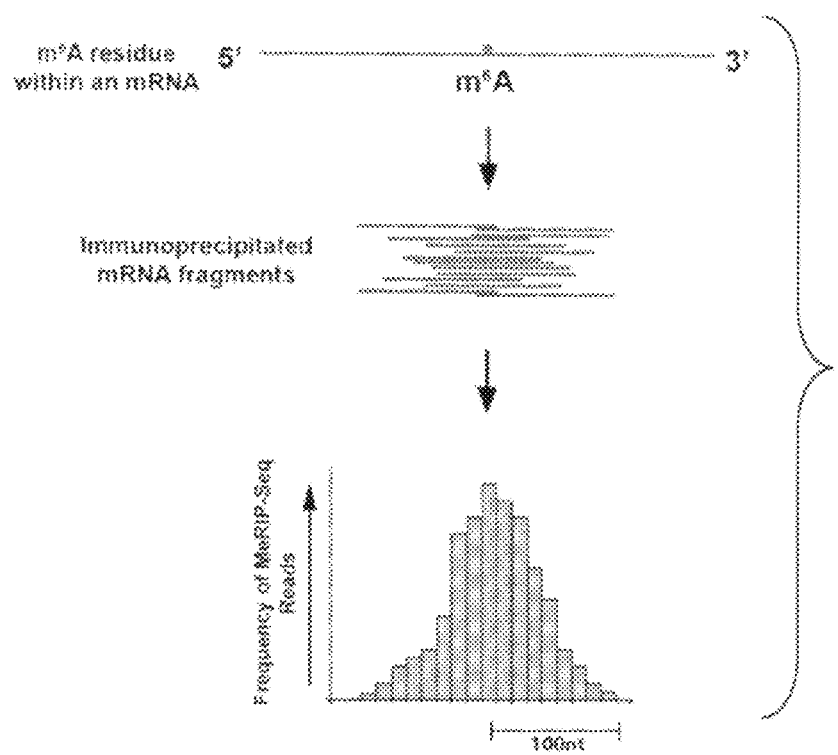
Figure 4C:
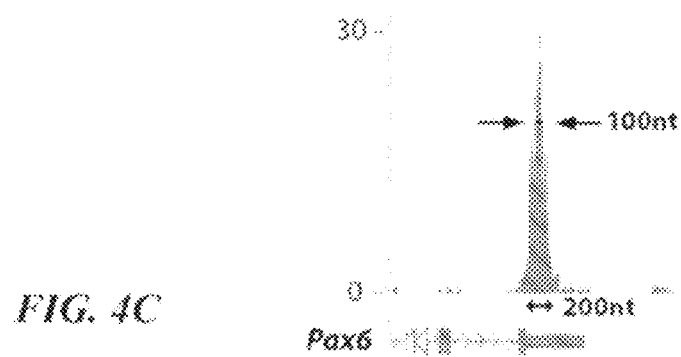

In order to identify m$^6$A peaks throughout the genome, the sites at which these significant 25 nt-wide windows clustered together to form distinct peaks were next determined. The size of the individual RNA fragments from which all samples were prepared was approximately 100 nt. For each immunoprecipitated fragment, an m$^6$A residue could technically exist at the 5'-most base of the fragment or at the 3'-most base of the fragment. Therefore, a single m$^6$A residue could be part of immunoprecipitated RNA fragments that at their extremes contain bases 100 nt upstream or 100 nt downstream of the actual m$^6$A site. Thus, when identifying m$^6$A peaks, it was predicted that they would be approximately 200 nt wide at their base (FIGS. 4A-4C).

To determine the 200 nt-wide regions of significant m$^6$A enrichment, adjacent significant windows were concatenated from the 25 nt analysis and concatenated windows that were smaller than 100 bp wide were filtered out. It was reasoned that because the RNA in each sample was sheared to approximately 100 nt-long fragments, MeRIP reads which clustered around m$^6$A sites would be at the highest density within the central 100 nt-wide region of the peak. Thus, 100 nt was selected as the minimum size of the concatenated windows required for peak definition. In some cases, the length of the concatenated windows spanned >200 nt. In such cases, these regions were considered to have n m$^6$A peaks, where n corresponds to the minimum number of m$^6$A peaks that could result in a concatenated window of that length. Using this method for peak calling, 41,072 peaks total across all MeRIP-Seq mouse samples and 57,236 peaks total across HEK293T samples were identified. Of these peaks, 13,471 m$^6$A were significant in all three mouse brain samples and 18,756 in all three HEK293T samples.

The stringent filtering criteria outlined above allowed the false discovery rate of the method of the present invention for identifying m$^6$A sites to be minimized. The drawback to this approach, of course, is that the final list of high-confidence m$^6$A sites identified is likely to be an underestimate of the true number of m$^6$A sites throughout the genome. The 41,072 significant windows identified from the 25 nt analysis (above) likely contain many valid m$^6$A sites, and provided is the list of coordinates for each of these significant windows.

Determining m$^6$A Peaks Across the Transcriptome—

Determining m$^6$A peaks across the genome (above) was necessary for identifying regions of m$^6$A localization within intronic and intergenic regions. However, to determine the enrichment and clustering of m$^6$A peaks within individual transcripts, m$^6$A peaks across the transcriptome were also identified. To do this, each RefSeq exon were split into windows approximately 25 nt in size, using all known annotated transcript forms of each gene. The actual size of the window was computed by counting how many 25 nt windows would be needed to span each exon, and then distributing the base pairs evenly across those windows to avoid the creation of small windows at the end of each exon. TopHat (Trapnell et al., "TopHat: Discovering Splice Junctions With RNA-Seq," *Bioinformatics* 25:1105-1111 (2009), which is hereby incorporated by reference in its entirety) was then used to align the original sequenced data to the genome, with RefSeq exon-exon splice junctions used for the known exon junctions parameter. The split size was also set to half of the sequence length of Sample 1 (16 nt), which had a smaller sequenced length than the other samples. The default split size (25 nt) was used for the other replicates.

The number of reads within each replicate that mapped to each window by using BEDTools' intersectBed was then determined. As with the genome-wide peak identification (above), the number of reads in the MeRIP sample was then compared to the number in the non-IP sample within each window and Fisher's exact test was used to compute p-values for the windows of each replicate. These p-values were then adjusted using Benjamini-Hochberg, and only those windows with p-values less than or equal to 0.05 in all samples were kept. Next, windows were concatenated, and those that did not join to span contiguous regions at least 100 bp in length across mature, spliced transcripts were filtered out. The remaining windows were split into peaks between 100-200 nt in size. This method identified 23,924 peaks across the transcriptome, which overlapped with 93% of the peaks in the high-confidence set (above).

The mergeBed program from BEDTools (Quinlan et al., "BEDTools: A Flexible Suite of Utilities for Comparing Genomic Features," *Bioinformatics* 26:841-842 (2010), which is hereby incorporated by reference in its entirety) was then used to join these peaks into contiguous regions across the genome and then re-split them into individual 100-200 nt peaks. This method allowed the removal of redundant peaks which mapped to the same area of two or more transcript variants of a given gene, and it resulted in a total of 17,830 m$^6$A peaks. To determine the overlap between these transcriptomics peaks and genomically-defined peaks in the "high-confidence" set (above), BEDTools' intersectBed was used. It was required that each peak must overlap at least 50% with another peak, setting the –f parameter to 0.5.

Estimation of False Discovery Rate for Identification of m$^6$A Peaks—

Analyses of both the BWA-aligned sequences across the genome and the TopHat-aligned sequences across the transcriptome are susceptible to the multiple testing problem, which is caused by the large number of 25 nt windows being independently tested in each analysis. To account for this, the Benjamini-Hochberg method was used for error correction, which seeks to estimate the threshold at which a certain false discovery rate (FDR) is achieved. An FDR of 0.05 was chosen to be used, and the p-values were adjusted accordingly per sample. However, it is likely that the FDR for the high-confidence set of m$^6$A peaks is actually lower than 0.05, because of the numerous filtration steps used to obtain this list of m$^6$A peaks (above). First, a window was only considered significant if the adjusted p-value was less than or equal to 0.05 in all three replicates. Second, only significant windows were used that continuously spanned a region of 100 nt or more when joined. Thus, while the FDR is estimated to be around 0.05 per sample, it is likely less for the list of high-confidence peaks.

Annotation of m$^6$A Peaks—

Peaks were annotated by applying BEDTools' intersectBed in a tiered fashion. First, RefSeq gene annotations were split into two subsets, those for protein coding genes and those for non-protein coding genes. The tiered system first mapped peaks to protein coding gene coding sequences, UTRs, exons, introns, and finally full genes, in that order. Those that mapped 90% were given priority, then 50%, and finally any by overlap. Then, the same was performed on non-protein coding gene annotations, in the same order. Duplicate mappings were removed such that a peak was mapped only once to any given RefSeq gene annotation. Because individual m$^6$A peaks often mapped to multiple transcript variants of the same RNA, only one transcript variant and RefSeq accession number were used per gene when generating the list of 4,654 unique genes in the high-confidence set of m⁶A peaks. Additionally, only one transcript variant per gene was reported in Table 3 and Table 5, infra, which list the m⁶A peaks from genes with the greatest enrichment and the greatest number of m⁶A peaks, respectively.

Distribution of m⁶A Peaks and Samples—

Figure 9A:
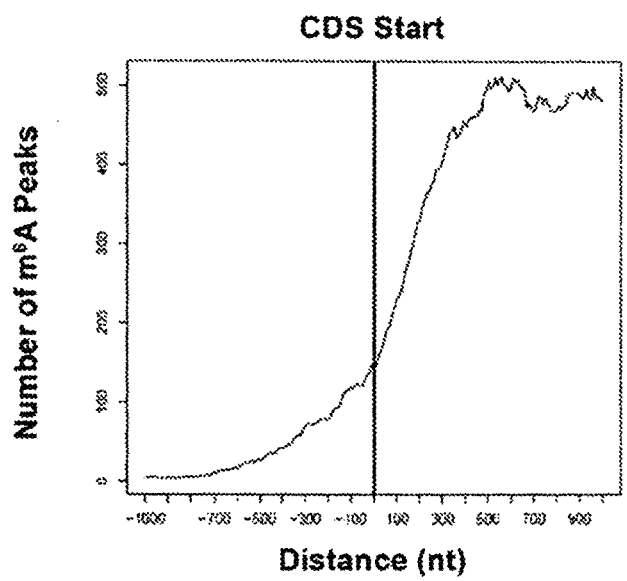
FIGS. 9A-9D illustrate features of adenosine methylation in the mouse and human transcriptomes.
Figure 9B:
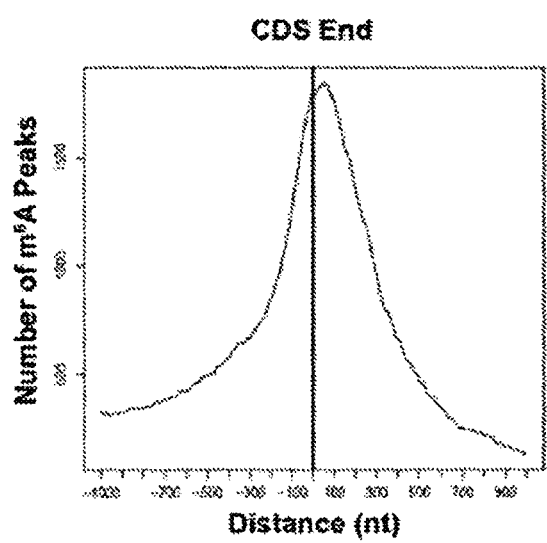
Figure 9C:
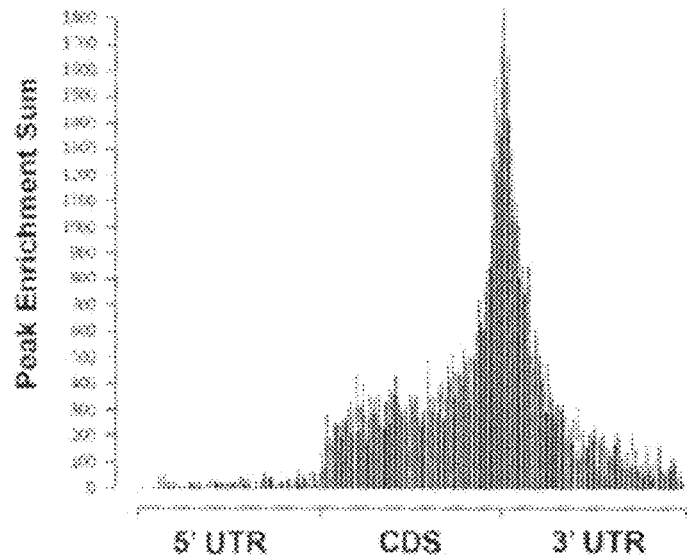
Figure 9D:
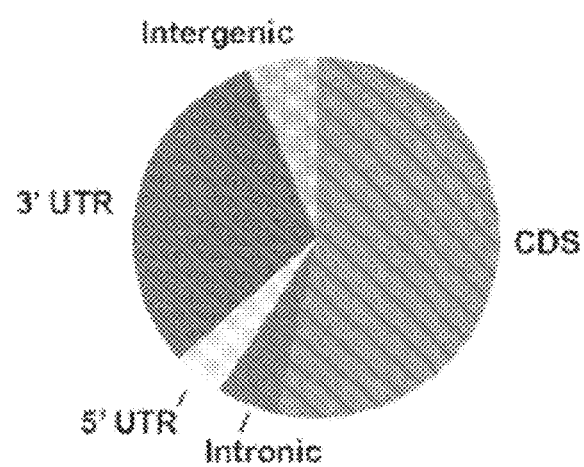

The peak annotations from above were then compiled into the pie chart distributions for the mouse brain peaks (FIG. 5C) and the HEK293T peaks (FIG. 9D). The distribution for the control data sets was computed in a similar tiered fashion, but by comparing RefSeq annotations against the original control datasets. These percentages were then averaged across the replicate controls.

Analysis of m⁶A Peak Distribution Along an mRNA—

First, a subset of the RefSeq gene annotations was derived by taking only one transcript variant of each gene. Next, overlapping transcript variants were removed from the set to reduce any ambiguity in determining which transcript a peak is from. Peaks were then mapped into this single-transcript-variant non-overlapping RefSeq subset. If the peak fell within a gene exon, then its position within the mature transcript was calculated using the exon lengths. This was then converted to a position within the 5' UTR, the coding sequence, or the 3' UTR segments, and divided by the length of that region and multiplied by 100 to determine a percentile for where this peak fell. The percentile bin that the peak fell into was then incremented, and the bins were plotted as a percentage of the total number of peaks in the dataset.

For plotting m⁶A enrichment (FIG. 9C), BEDTools' intersectBed was used to first calculate the number of reads that mapped to each peak, for each sample and replicate, which was then compiled into a single file to store peak read counts. A similar procedure was then performed on all RefSeq gene exons, and then tabulated by gene to get read counts from all samples for mature transcripts. The peak enrichment was computed for each peak by dividing the number of MeRIP reads by the number of control reads that mapped to that peak, each normalized for the total number of reads that were mapped, for each replicate, and then averaged across the three replicates. Peaks that had control RPKMs of less than 1 or that were in genes that had control RPKMs of less than 1 were filtered out. These are still peaks, given their high number of reads in the MeRIP samples, but the lack of reads in the control skews the enrichment score. The peaks were then mapped to percentile bins for the 5' UTR, CDS, and 3' UTR regions as above. The purpose of this plot was to show the distribution of potential m⁶A sites and their cumulative enrichment, and so the sum of the enrichment scores at bin was used to accurately determine both the peak enrichment and the number of peaks in each bin.

Determining the Most Frequently Methylated m⁶A Peaks—

Figure 8A:
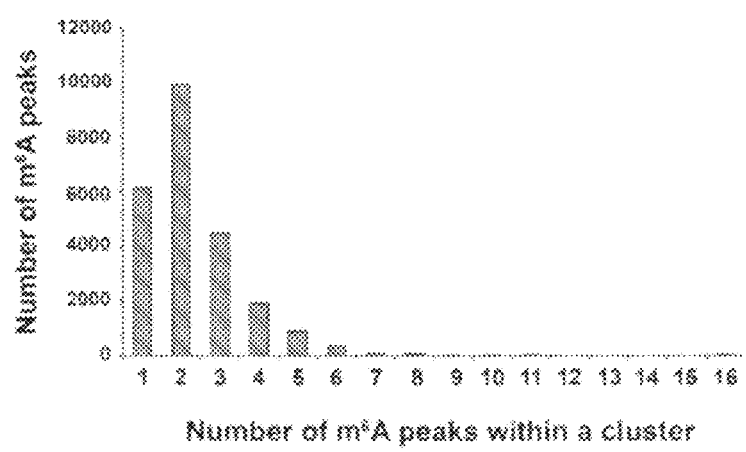
FIGS. 8A-8D show distribution of $m^6A$ Peaks in mouse brain and HEK293T cell RNA.
Figure 8B:
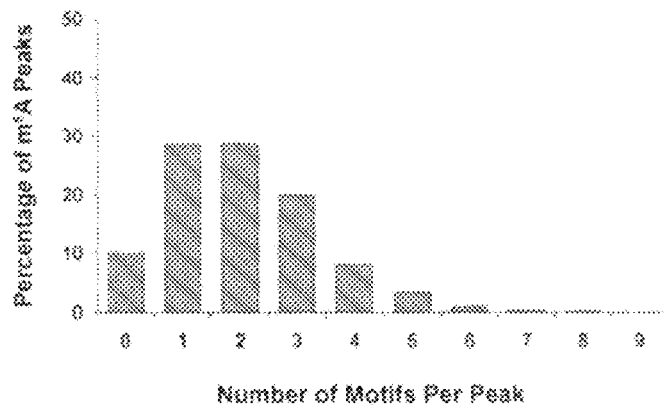
Figure 8C:
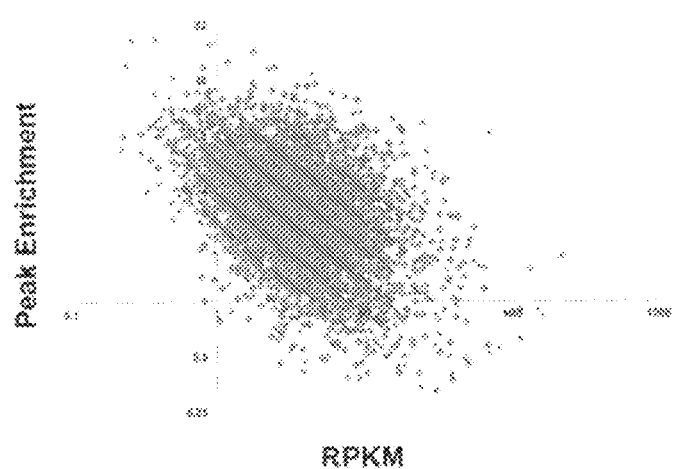
Figure 8D:
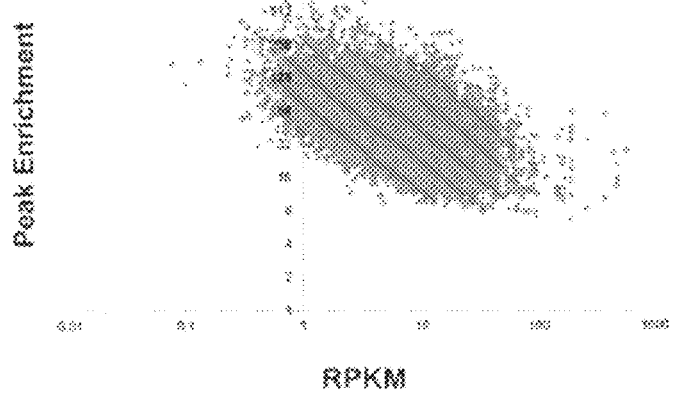

To determine the frequency of methylation at individual m⁶A peaks, the ratio of the number of reads in the MeRIP sample within the region defined by each m⁶A peak were calculated, normalized by the total number of reads mapped to the genome in that sample, to the RPKM of the gene that the peak resides in. This ratio was averaged across all three replicates, and then shown on a $\log_2$ scale. This method made it possible to determine the relative frequency of methylation at a given m⁶A peak. However, m⁶A peaks may be due to the presence one or more m⁶A residues. Therefore, the determination of the m⁶A peaks with high degrees of methylation could reflect either the stoichiometry of a single m⁶A residue, or a cluster of highly adjacent m⁶A residues, each with potentially low or varying stoichiometry. In many cases, single MeRIP-Seq peaks contained only one m⁶A consensus motif, suggesting a single methylation site (FIG. 8B); however, until m⁶A sites can be determined transcriptome-wide with single nucleotide resolution, it is impossible to know for sure whether an m⁶A peak corresponds to a single or multiple m⁶A residues.

m⁶A Enrichment vs RPKM—

To compute the enrichment of human and mouse m⁶A peaks, the normalized number of MeRIP reads by the normalized number of control reads that mapped to each peak were divided and averaged across replicates. The RPKM was computed for the gene transcript that the peak fell into, averaged across control replicates.

Distribution of m⁶A Surrounding CDS Start and End Sites—

Using the filtered subset of RefSeq annotations that had only one transcript variant per gene and no overlapping regions, a .bed file of 10-bp windows 1 kb upstream and downstream of both the coding sequence start and end sites was created. Windows were generated with the transcriptome coordinates of the specific transcript, taking into consideration the length limitations of each transcript. For example, the coding sequence start windows would stop at the beginning of the 5' UTR and the end of the coding sequence. These transcriptome windows were then translated into genomic coordinates and the peaks were translated as single by points at the center of each peak. BEDTools' intersectBed was used to count the number of peaks that fell into each window. The peak counts were then tabulated across all genes into two sets of 200 bins that represented 1 kbp upstream and downstream of both the CDSs and the CDSe. The bins were plotted with 100 bins on each side of the CDSs or CDSe, and the center point was computed as the average of the adjacent bins.

eRIP-Seq Gene Ontology—

Gene ontology ("GO") analysis was performed using the DAVID bioinformatics database (Huang da et al., "Bioinformatics Enrichment Tools: Paths Toward the Comprehensive Functional Analysis of Large Gene Lists," *Nucleic Acids Res.* 37:1-13 (2009); Huang da et al., "Systematic and Integrative Analysis of Large Gene Lists Using DAVID Bioinformatics Resources," *Nature Protocols* 4:44-57 (2009), which are hereby incorporated by reference in their entirety). GO classification for cellular component, biological process, and molecular function were performed at default settings. To provide additional validation of the results, two separate analyses were performed using two different lists of genes as background for the mouse brain dataset: 1) the list of genes expressed in all MeRIP and non-IP samples combined and 2) a list of random genes taken from the mouse transcriptome.

Evolutionary Conservation and Motif Statistics—

Analysis of phylogenetic conservation was done by comparing PhyloP (Pollard et al., "Detection of Nonneutral Substitution Rates on Mammalian Phylogenies," *Genome Res.* 20:110-121 (2010), which is hereby incorporated by reference in its entirety) scores of m⁶A peaks to those same peaks randomly shuffled within gene exons using BEDTools (Quinlan et al., "BEDTools: A Flexible Suite of Utilities for Comparing Genomic Features," *Bioinformatics* 26:841-842 (2010), which is hereby incorporated by reference). PhyloP scores were computed for each using completeMOTIFs, which uses the phastCons scores from vertebrates. Significant differences in the distributions of the PhyloP scores were determined with the Kolmogorov-Smirnov (K-S) test in the R programming environment, using the stats library package. Motif analysis was done using FIRE (Elemento et al., "A Universal Framework for Regulatory Element Discovery Across All Genomes and Data Types," *Mol. Cell* 28:337-350 (2007), which is hereby incorporated by reference in its entirety) with default RNA analysis parameters. For motif analysis, the sequence under the peaks located in RefSeq mRNAs were extracted and converted to the appropriate strand. MicroRNA analyses were performed using custom scripts and TargetScan miRNA predictions.

Analysis of $m^6A$ Localization to Splice Junctions—

The number of $m^6A$ peaks found at exon-exon junctions was determined by overlapping the set of 14,416 transcriptome-wide $m^6A$ peaks that fall within CDSs with exon-exon junctions compiled from known RefSeq exons. Four different sets of control "peaks" were also generated, which were used to establish a background level of overlap with exon-exon junctions. These control sets included 1) randomly generated peaks, 2) upstream adjacent region peaks, 3) downstream adjacent region peaks, and 4) mixed adjacent region peaks.

The set of random control peaks was generated with BEDTools' shuffleBed program to randomly shuffle regions of the same size as the $m^6A$ CDS peaks throughout coding sequence exons. Peaks were shuffled only to exons on the same chromosome, and the shuffleBed program was modified so that it would retain the transcript of the new exon to which it was mapped. By default, shuffleBed allows the new random peak to extend beyond the end of the exon; therefore, the code was further modified to allow it to map peaks up to 50 nt upstream of the start of an exon. To make this a fair comparison, the code was also modified to allow it to map peaks up to 50 nt upstream of the start of the exon. The peaks are between 100-200 nt in size, so 50 nt is enough to allow a peak to cross the 5' junction but not so much that a peak would end up being mapped completely out of the exon. These shuffled peaks were then mapped to transcriptome coordinates (the coordinates of mature transcripts for individual transcript variants of a gene).

The adjacent region control sets of peaks were generated by taking the regions immediately 5' (the upstream adjacent regions set), 3' (the downstream adjacent regions set), or either 5' or 3' (the mixed adjacent regions set) to each $m^6A$ peak within a CDS. The size of each control peak matched that of the adjacent $m^6A$ peak which was located either up- or downstream. Additionally, if the region adjacent to an $m^6A$ peak contained another $m^6A$ peak, the next available adjacent region which did not contain an $m^6A$ peak was used. This step ensured that the control peaks were adjacent to, but not overlapping with, $m^6A$ peaks.

After generating all four sets of control peaks, the number of exon-exon junctions that overlapped with the peaks within each set was determined as above.

Poly(A) Site Analysis—

To determine the degree of overlap between poly(A) cleavage sites and $m^6A$ peaks within 3' UTRs, a list of known poly(A) cleavage sites were used (Brockman et al., "PACdb: PolyA Cleavage Site and 3'-UTR Database," *Bioinformatics* 21:3691-3693 (2005), which is hereby incorporated by reference in its entirety) and examined to determine whether 50 nt regions upstream of each cleavage site overlapped with the regions of $m^6A$ peaks in 3' UTRs. The overlap between these poly(A) cleavage sites and randomly generated regions in the same 3' UTRs were also examined. These random regions were generated by using the BEDTools shuffleBed program with RefSeq 3' UTR as the inclusion regions and the chromosome flag set. Using shuffleBed, 100 different sets of random peaks were generated and the average of the number of intersections with polyA sites. BEDTools' intersectBed was used to determine the overlapping regions, with the –f flag set to 0.2 to require that at least one fifth of each window (20-40 nt) overlap with a polyA site. The peaks were shuffled a total of 100 times, and the average of the total number of overlaps with polyA sites was used for the random counts.

MicroRNA Expression Analysis—

A wildtype mouse brain miRNA expression profile, and mouse miRNA TargetScan target predictions were downloaded and mapped to RefSeq transcript 3' UTRs. $m^6A$ peaks were mapped to the same RefSeq transcript 3' UTRs. For each miRNA, the number of target transcripts were determined, i.e., the number of 3' UTRs with at least 1 miRNA target. For each miRNA, the number of $m^6A$ peaks found in all 3' UTRs targeted by the miRNA were determined. Then, the ratio between the number of $m^6A$ peaks and the number of target transcripts was calculated for each miRNA, so as to obtain an average number of $m^6A$ peaks per target 3' UTR. Using this miRNA expression profile, the 25 least and 25 most expressed miRNAs in mouse brain were identified and average numbers of $m^6A$ peaks per target 3' UTR for these two miRNA groups were compared using Wilcoxon tests and boxplots.

Comparison of Mouse Brain and HEK293T Datasets—

RefSeq gene annotations were used to compare the peaks found in the mouse brain tissue samples to those found in the HEK293T tissue cell line. The peaks were matched with RefSeq annotations, with priority given to coding sequences, then the UTRs, exons, introns, and lastly, full genes, using BEDTools' intersectBed. If a peak mapped to more than one CDS exon, for example, all matches were kept. Using Microsoft Excel, the official gene symbols present in each peak set were tabulated and compared to determine the gene symbols present in both datasets.

Analysis of $m^6A$-Containing Transcripts—

The pattern of $m^6A$ peaks gives hints as to the stage at which the RNA can become methylated. A small percentage of $m^6A$ peaks were observed within intronic regions, which suggests that at least some mRNAs are methylated as immature pre-mRNAs within the nucleus. The methylation of pre-mRNAs is consistent with the nuclear localization of MT-A70, the adenosine methyltransferase (Bokar et al., "Purification and cDNA Cloning of The AdoMet-Binding Subunit of the Human mRNA (N6-adenosine)-Methyltransferase," *RNA* 3:1233-1247 (1997), which is hereby incorporated by reference in its entirety). However, it was also found that 5% of $m^6A$ peaks throughout the transcriptome contain reads that span an exon-exon junction, indicating that mature, spliced transcripts contain $m^6A$ and that $m^6A$ might have roles in mRNA processing events that occur both within and outside of the nucleus.

A-to-I Editing Site Analysis—

It was sought to explore whether adenosine methylation serves to regulate the conversion of adenosine to inosine, which is mediated by ADAR enzymes. ADARs exhibit markedly reduced activity towards $m^6A$ compared to adenosine (Veliz et al., "Substrate Analogues for an RNA-Editing Adenosine Deaminase: Mechanistic Investigation and Inhibitor Design," *J. Am. Chem. Soc.* 125:10867-10876 (2003), which is hereby incorporated by reference in its entirety), raising the possibility that adenosine methylation may act as a regulatory mechanism to control editing. $m^6A$ peaks were compared to a list of 2,545 total A-to-I editing sites identified in mouse and human (Bahn et al., "Accurate Identification of A-To-I RNA Editing in Human by Transcriptome Sequencing," *Genome Res.* 1:142-150 (2011); Enstero et al., "A Computational Screen for Site Selective A-to-I Editing Detects Novel Sites in Neuron Specific Hu Proteins," *BMC Bioinformatics* 11:6 (2010); Li et al., "Widespread RNA and DNA Sequence Differences in the Human Transcriptome," *Science* 333:53-58 (2011); Maas et al., "Genome-Wide Evaluation and Discovery of Vertebrate A-to-I RNA Editing Sites," *Biochem. Biophys. Res. Commun.* 412:407-412 (2011); Neeman et al., "RNA Editing Level in the Mouse is Determined by the Genomic Repeat Repertoire," *RNA* 12: 1802-1809 (2006); Sakurai et al., "Inosine Cyanoethylation Identifies A-to-I RNA Editing Sites in the Human Transcriptome," *Nat. Chem. Biol.* 6:733-740 (2010); Wahlstedt et al., "Large-Scale mRNA Sequencing Determines Global Regulation of RNA Editing During Brain Development," *Genome Res.* 19:978-986 (2009), which are hereby incorporated by reference in their entirety). Human A-to-I editing sites were converted to mm9 genomic coordinates using LiftOver from the UCSC Genome Browser (Rhead et al., "The UCSC Genome Browser database: Update 2010," *Nucleic Acids Res.* 38:D613-619 (2010), which is hereby incorporated by reference in its entirety). Genomic regions defined by $m^6A$ peaks in the high-confidence set were used to look for overlaps with A-to-I sites. The random regions used as a reference for background overlap were generated using BEDTools' shuffleBed program (with the –incl flag set to known RefSeq genes). Random regions were set to be the same size as the regions of $m^6A$ peaks and were investigated for overlaps with A-to-I sites. This process was repeated for 100 permutations of random regions, and the average number of overlaps with A-to-I sites was determined.

This analysis revealed that only 10 of these A-to-I sites overlapped with $m^6A$ peaks, compared to an average of 8.25 overlaps in the control regions, indicating that $m^6A$ peaks are not significantly overrepresented at A-to-I editing sites. (p=0.54; chi-square test).

Although the presence of $m^6A$ would technically inhibit A-to-I editing and, therefore, potentially explain this lack of association, both A-to-I editing and $m^6A$ peaks exhibit substoichiometric modification (Iwamoto et al., "Estimating RNA Editing Efficiency of Five Editing Sites in the Serotonin 2C Receptor by Pyrosequencing," *RNA* 11:1596-1603 (2005); Narayan et al., "An In Vitro System for Accurate Methylation of Internal Adenosine Residues in Messenger RNA," *Science* 242:1159-1162 (1988); Rana et al., "Analysis and In Vitro Localization of Internal Methylated Adenine Residues in Dihydrofolate Reductase mRNA," *Nucleic Acids Res.* 18:4803-4808 (1990), each of which is hereby incorporated by reference in its entirety). Therefore, the absence of a correlation between these two modifications is unlikely to reflect a complete inhibition of A-to-I editing by adenosine methylation. Nevertheless, because a given adenosine could be methylated or deaminated at very low levels, the possibility that $m^6A$ inhibits A-to-I editing at some sites cannot be ruled out.

Example 1

Detection of $m^6A$ in Mammalian mRNA

Because $m^6A$ exhibits the same base pairing as unmodified adenosine, it is not readily detectable by standard sequencing or hybridization-based approaches. Additionally, $m^6A$ is not susceptible to chemical modifications which might otherwise facilitate its detection, such as bisulfite treatment which is used to detect $m^5C$ in DNA. The methods used thus far to detect $m^6A$ have involved treating cells with radiolabeled methionine, the precursor of the endogenous methylating agent S-adenosylmethionine, to impart radiolabeled methyl groups to adenosine (Csepany et al., "Sequence Specificity of mRNA N6-Adenosine Methyltransferase," *J. Biol. Chem.* 265:20117-20122 (1990); Dubin et al., "The Methylation State of Poly A-Containing Messenger RNA from Cultured Hamster Cells," *Nucleic Acids Res.* 2:1653-1668 (1975); Narayan et al., "An in vitro System for Accurate Methylation of Internal Adenosine Residues in Messenger RNA," *Science* 242:1159-1162 (1988), each of which is hereby incorporated by reference in its entirety). Radiolabeled $m^6A$ residues are subsequently mapped with thin-layer chromatography or HPLC.

Figure 1B:
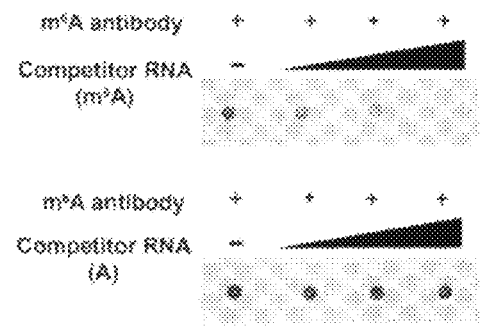
Figure 1C:
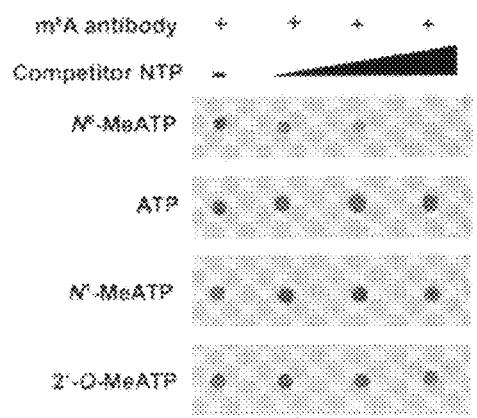
Figure 1D:
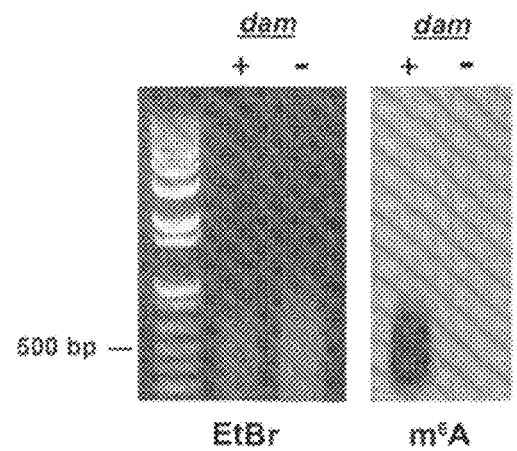

To simplify detection of $m^6A$, an immunoblotting strategy was developed. For these experiments, a previously described anti-$m^6A$ antibody was used (Bringmann et al., "Antibodies Specific for N6-Methyladenosine React with Intact snRNPs U2 and U4/U6," *FEBS Lett.* 213:309-315 (1987); Jia et al., "N6-Methyladenosine in Nuclear RNA Is a Major Substrate of the Obesity-Associated FTO," *Nat. Chem. Biol.* 7(12):885-887 (2011); Munns et al., "Characterization of Antibodies Specific for N6-Methyladenosine and for 7-Methylguanosine," *Biochemistry* 16:2163-2168 (1977), each of which is hereby incorporated by reference in its entirety). To ensure the specificity of this antibody for $m^6A$, dot blots were performed using modified oligonucleotides immobilized to a membrane. The $m^6A$ antibody selectively bound to oligonucleotides containing a single $m^6A$ residue, and exhibited negligible binding to oligonucleotides containing unmodified adenosine (FIG. 1A). The binding was competed by incubating the antibody with increasing concentrations of an $m^6A$-rich competitor RNA (FIG. 1B). However, RNA containing unmodified adenosine did not compete for binding. Furthermore, binding was competed by $N^6$-methyladenosine triphosphate, but not by ATP or other modified adenosine triphosphates including $N^1$-methyladenosine and 2'-O-methyladenosine (FIG. 1C). Finally, to examine the specificity of the antibody in the context of other nucleotide sequences, the inventors took advantage of the fact that the enzyme encoded by the DNA adenine methylase (dam) gene in *E. coli* methylates the $N^6$ position of adenosine in DNA. Upon subjecting digested DNA isolated from dam+ and dam– *E. coli* to immunoblotting using the $m^6A$ antibody, robust signals were found only in the DNA samples from the dam+ strain (FIG. 1D). Collectively, these data demonstrate the high sensitivity and selectivity of this antibody for $m^6A$, as well as its ability to detect $m^6A$ within cellular nucleotide pools.

Figure 2A:
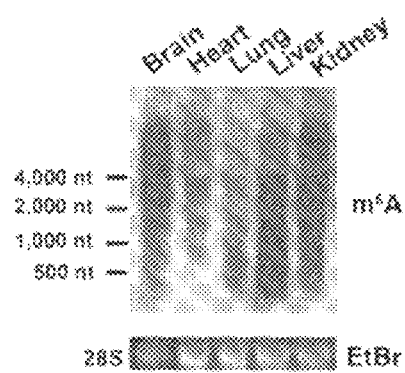
FIGS. 2A-2D demonstrate the distribution and dynamic cellular regulation of $m^6A$ in RNA.
Figure 2B:
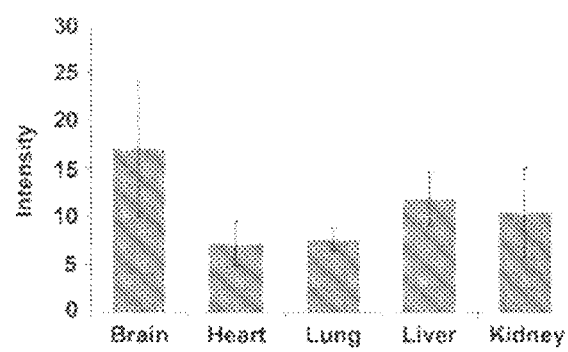
Figure 10A:
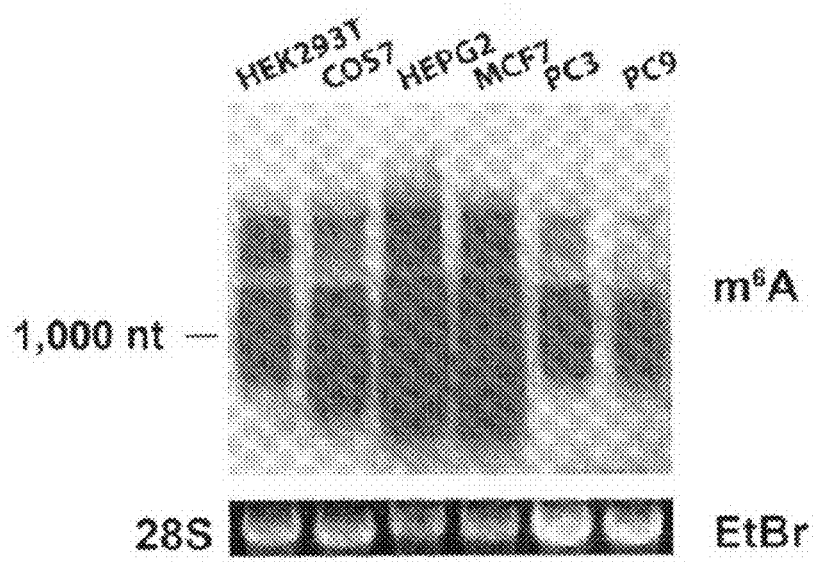
FIGS. 10A-10B show that $m^6A$-containing transcripts are found at varying levels across individual cell lines and are not detected in poly(A) tails.

To explore the abundance of $m^6A$ within various RNA populations, RNA was isolated from several mouse tissues and subjected to immunoblot analysis using the $m^6A$ antibody (FIG. 2A). It was found that $m^6A$ was present in all RNA samples tested, indicating that this modified nucleotide is widely distributed in many tissues, with particularly high enrichment in liver, kidney, and brain (FIG. 2B). In addition, large differences were observed in the $m^6A$ content of various immortalized cell lines, including several cancer cell lines, which further indicates that large differences in $m^6A$ levels exist in different cell populations (FIG. 10A).

Figure 2C:
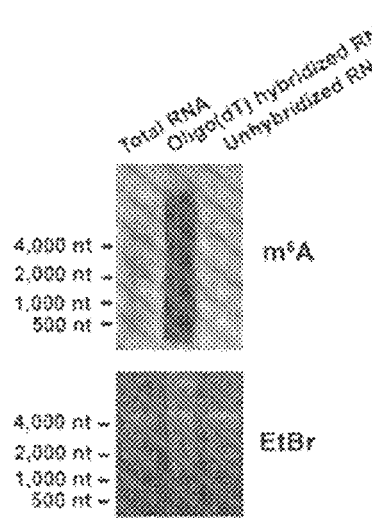
Figure 2D:
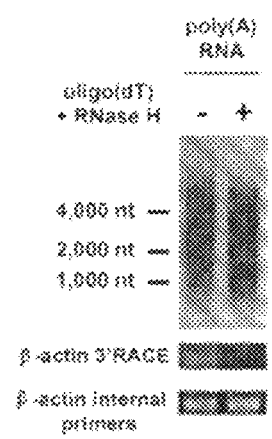

$m^6A$ immunoreactivity was detected in bands throughout the molecular weight range of the blot (~0.2 kb to ~10 kb), consistent with incorporation of $m^6A$ in mRNA. Indeed, fractionation of whole cellular RNA into polyadenylated and nonpolyadenylated RNAs indicates that $m^6A$ immunoreactivity is enriched in the polyadenylated RNA pool, which indicates that m⁶A in cellular RNA is localized to mature mRNA (FIG. 2C). To determine whether m⁶A is present in poly(A) tails, the poly(A) tail was selectively removed from cellular mRNA using oligo(dT) hybridization and RNase H treatment. Transcripts depleted of the poly(A) tail did not exhibit an appreciable reduction in m⁶A levels (FIG. 2D). In addition, immunoblotting poly(A) tails alone showed minimal m⁶A immunoreactivity. Together, these data demonstrate that m⁶A is primarily an internal modification which is largely absent from the poly(A) tail.

Example 2

Dynamic Regulation of m⁶A

Figure 10B:
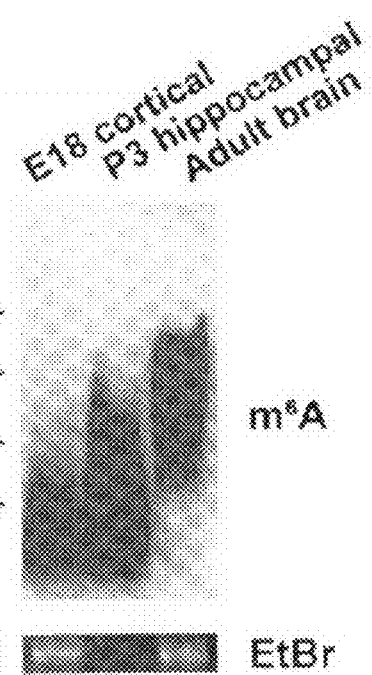
Figure 11A:
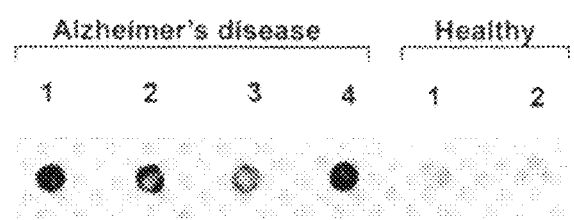
FIGS. 11A-11B show that $m^6A$ levels are altered in human disease tissues.
Figure 11B:
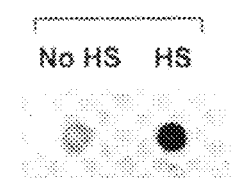

The observation that m⁶A is highly enriched within the brain prompted the inventors to investigate the temporal dynamics of m⁶A levels during different stages of neural development. Immunoblotting RNA samples with the m⁶A antibody indicates that m⁶A is present in mRNA at low levels throughout embryogenesis but increases dramatically by adulthood (FIG. 3A). A similar increase in m⁶A levels was also observed in RNA isolated from embryonic and postnatal rat brain cultured neurons (FIG. 10B), which indicates that upregulation of m⁶A levels accompanies neuronal maturation.

Next, it was asked whether adenosine methylation is a dynamically regulated post-transcriptional modification and whether its levels can be regulated by specific demethylating enzymes. In the search for potential demethylating enzymes that act to remove the methyl group from m⁶A, members of the family of Fe(II)- and 2-oxoglutarate-dependent oxygenases were the focus, several of which have previously been shown to demethylate both DNA and RNA (Falnes et al., "Repair of Methyl Lesions in DNA and RNA by Oxidative Demethylation," *Neuroscience* 145:1222-1232 (2007); Gerken et al., "The Obesity-Associated FTO Gene Encodes a 2-Oxoglutarate-Dependent Nucleic Acid Demethylase," *Science* 318:1469-1472 (2007), each of which is hereby incorporated by reference in its entirety). Consistent with the findings of Jia et al., "N6-Methyladenosine in Nuclear RNA Is a Major Substrate of the Obesity-Associated FTO," *Nat. Chem. Biol.* 7(12):885-887 (2011), which is hereby incorporated by reference in its entirety, it was observed that FTO decreased m⁶A levels when overexpressed in mammalian cells (FIG. 3B). Furthermore, it was found that overexpression of FTO resulted in a broad size range of RNAs that exhibit reduced m⁶A immunoreactivity (FIG. 3B).

Example 3

MeRIP-Seq Identifies m⁶A-Containing RNAs Throughout the Transcriptome

To obtain insight into potential roles for m⁶A, the characterization of its distribution throughout the transcriptome was sought. To do this, it was first determined whether the m⁶A antibody could be used to enrich m⁶A-containing RNAs. In vitro immunoprecipitation experiments showed that a single round of MeRIP produces ~70-fold enrichment, and two rounds produce over 130-fold enrichment for m⁶A-containing targets. To identify m⁶A sites throughout the transcriptome, a method that combines m⁶A-specific methylated RNA immunoprecipitation (MeRIP) with next-generation sequencing (RNA-Seq) was developed. The procedure for MeRIP-Seq (outlined in FIG. 4A) involves randomly fragmenting the RNA to approximately 100 nt-sized fragments prior to immunoprecipitation. Because an m⁶A site could lie anywhere along the length of a given immunoprecipitated 100 nt fragment, sequencing reads are expected to map to a region which contains the m⁶A site near its center. At its extremes, this region would be predicted to be roughly 200 nt wide (100 nt up- and downstream from the m⁶A site) (FIG. 4B, 4C).

Next, MeRIP-Seq was used to identify m⁶A sites in total mouse brain RNA. Reads from the MeRIP sample frequently mapped to mRNAs and clustered as distinct peaks. As predicted, these peaks frequently converged to approximately 100 nt-wide regions near their midpoint (FIG. 4C). Furthermore, enrichment of reads in these regions was not observed in the non-IP control sample, which was composed of the input RNA prior to m⁶A immunoprecipitation, demonstrating the specificity of these peaks.

To determine the location of these peaks throughout the transcriptome, and thus characterize the regions of m⁶A localization, an algorithm for identifying m⁶A peaks was developed (see Example 1, supra). Additionally, replicate MeRIP-Seq experiments were performed utilizing (1) a different sequencing platform (Illumina's GAIIx vs HiSeq2000), (2) independently prepared RNA samples from different animals, and (3) an unrelated m⁶A antibody (Kong et al., "Functional Analysis of Putative Restriction-Modification System Genes in the *Helicobacter pylori* J99 Genome," *Nucleic Acids Res.* 28:3216-3223 (2000), which is hereby incorporated by reference in its entirety), which exhibited similarly high specificity for m⁶A. The algorithm was employed to identify m⁶A peaks that met a minimum p-value ($p \leq 0.05$, Benjamini and Hochberg corrected) within each individual sample. From the three samples, a total of 41,072 distinct peaks in the RNAs of 8,843 genes were identified, which are named the "filtered" set of m⁶A peaks.

Of these peaks, 80% were detected in at least two different replicates. The high concordance between these samples indicates that MeRIP-Seq is highly reproducible across different sequencing platforms and using different m⁶A antibodies. For subsequent bioinformatic analyses, the list of 13,471 m⁶A peaks was used in RNAs from 4,654 genes which were detected in all three replicates. This list demonstrated the presence of m⁶A in a substantial fraction of the transcriptome and indicated that m⁶A is a common feature of mammalian mRNAs.

Example 4 m⁶A is Detected in Non-Coding RNAs

The majority of the high-confidence m⁶A peaks (94.5%) were found within mRNAs. However, it was also observed that 236 (1.1%) of the peaks mapped to non-coding RNAs (ncRNAs) that were annotated in the RefSeq database (Table 4). In addition, 588 m⁶A peaks did not map to a known RefSeq mRNA or ncRNA. To determine whether these unannotated peaks localize to ncRNAs predicted in other databases, they were aligned to genomic regions of a set of 32,211 ncRNAs from the RIKEN functional annotation of mouse (FANTOM3) dataset that were obtained from the mammalian noncoding RNA database (RNAdb; Pang et al., "RNAdb—A Comprehensive Mammalian Noncoding RNA Database," *Nucleic Acids Res.* 33:D125-130 (2005), which is hereby incorporated by reference in its entirety). It was found that 216 of these peaks mapped to a FANTOM3 ncRNA (Table 4). All of these ncRNAs were greater than 200 nt in length, indicating that long ncRNAs are substrates for adenosine methylation. Additionally, when a set of conserved human lincRNAs were interrogated (Cabili et al., "Integrative Annotation of Human Large Intergenic Noncoding RNAs Reveals Global Properties and Specific Subclasses," Genes Dev. 25:1915-1927 (2011), which is hereby incorporated by reference in its entirety) for overlaps with $m^6A$ peaks, nine additional peaks that overlapped with these lincRNAs were found (Table 4). Collectively, these data identify several classes of ncRNAs as targets of adenosine methylation.

Example 5

Biochemical Validation of $m^6A$-Containing Transcripts

Figure 5A:
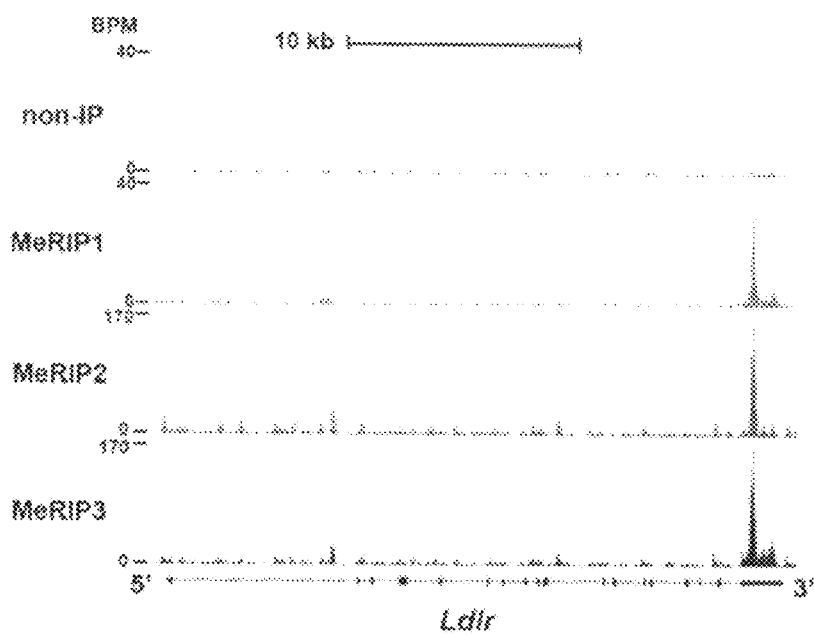
FIGS. 5A-5E show validation of m⁶A targets and characteristics of m⁶A localization.
Figure 5B:
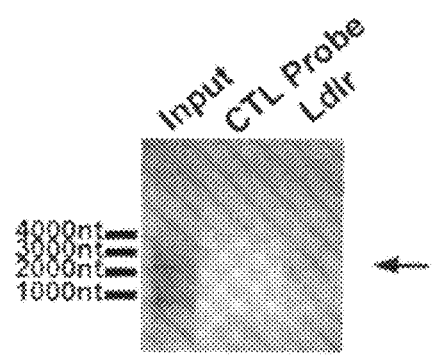
Figure 7A:
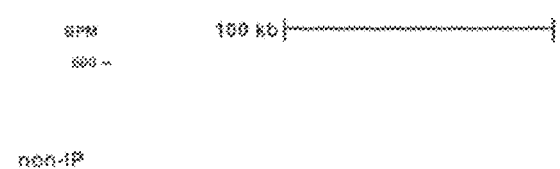
Figure 7A:
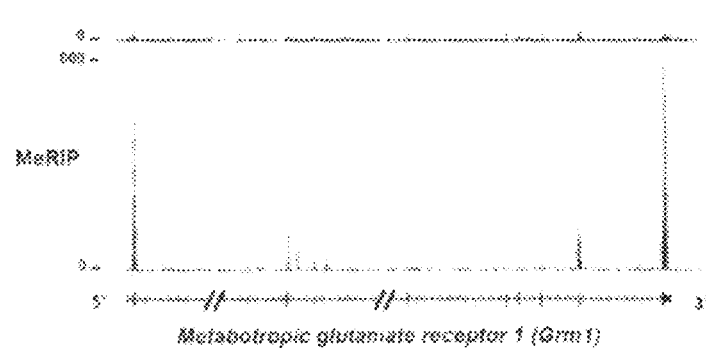
Figure 7E:
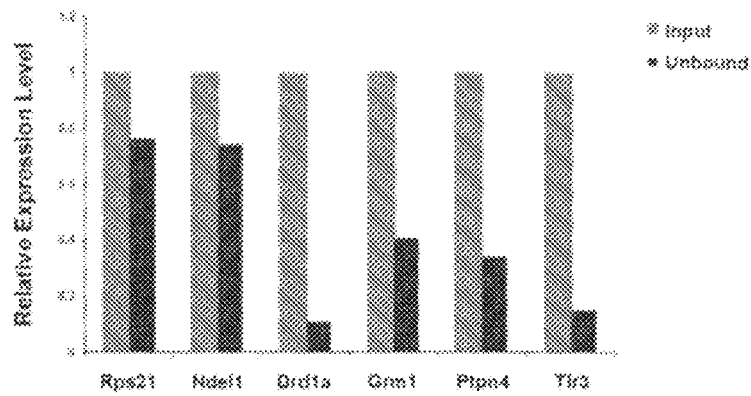

It was next sought to validate the presence of $m^6A$ in mRNAs identified with MeRIP-Seq. To do this, RNA pull-down assays were used to isolate individual mRNAs from total mouse brain RNA by hybridization to target-specific probes. Isolated mRNAs were then subjected to immunoblot analysis using the $m^6A$ antibody to detect the presence of $m^6A$. Using this method, the presence of $m^6A$ within low density lipoprotein receptor (Ldlr) (FIGS. 5A, 5B), metabotropic glutamate receptor 1 (Grm1), and dopamine receptor D1A (Drd1a) were validated (FIGS. 7A-7E). These mRNAs were chosen to demonstrate the present invention's ability to validate $m^6A$ presence in transcripts with multiple methylation sites (Grm1 and Drd1a) as well as those with single $m^6A$ peaks (Ldlr). To further demonstrate that MeRIP-Seq selectively enriches for these endogenous methylated targets, qRT-PCR was performed on the unbound fractions after RNA precipitation with the $m^6A$ antibody. As expected, substantial immunodepletion of Grm1, Drd1a, and other methylated targets in the unbound fraction was observed. In contrast, transcripts which lack $m^6A$ peaks, such as Rps21 and Ndel1, were detectable at high levels in the unbound fraction (FIG. 7E).

Example 6

$m^6A$-Containing mRNAs are Involved in Important Biological Pathways

To predict potential signaling pathways and cellular processes that involve $m^6A$, the DAVID bioinformatics database was used to identify the gene ontology (GO) terms that are enriched for $m^6A$-containing transcripts. It was found that genes encoding $m^6A$-containing RNAs are involved in a variety of cellular functions, including transcriptional regulation, RNA metabolism, and intracellular signaling cascades. In addition, it was observed that $m^6A$ peaks mapped to many genes linked to neurodevelopmental and neurological disorders, such as Bdnf, Dscam, Lis1, and Ube3a, as well as the neurexins and several neuroligins. Collectively, these data demonstrated that $m^6A$-containing RNAs are involved in a variety of biological pathways relevant to cellular signaling and disease.

Gene ontology (GO) analysis of genes encoding $m^6A$-containing RNAs was performed for biological process, cellular component, and molecular function. The GO term, the number of genes that fall within each category, the percentage of total genes encoding $m^6A$-containing mRNAs that fall within each category, the p-values obtained from GO enrichment analysis, the RefSeq IDs of the $m^6A$-containing RNAs of each term, the Bonferroni corrected-p-values, and the false discovery rate were all determined.

Since $m^6A$ is a physiological target of FTO, it was sought to determine whether mRNAs whose levels have previously been shown to be influenced by FTO activity contain $m^6A$. A list of 77 mRNAs whose levels are either up- or down-regulated in the liver, skeletal muscle, or white adipose tissue of mice homozygous for a nonsynonymous FTO point mutation were examined (Church et al., "A Mouse Model for the Metabolic Effects of the Human Fat Mass and Obesity Associated FTO Gene," PLoS Genet. 5:e1000599 (2009), which is hereby incorporated by reference in its entirety). mRNAs from seven genes which were significantly upregulated in FTO mutants (Acaca, Atf6, Bip, Gcdh, Irs1, Perk, and Xbp1) also contain $m^6A$ peaks. Intriguingly, some of these genes are involved in important metabolic pathways, raising the possibility that demethylation of the transcripts of these genes may contribute to the mechanism by which FTO regulates metabolism and energy homeostasis.

Example 7

Diverse Patterns of $m^6A$ Localization within Transcripts

Next, the pattern of adenosine methylation in mRNAs was characterized. mRNAs from many genes (46.0%) exhibit a single $m^6A$ peak, consistent with a single $m^6A$ site or a cluster of adjacent $m^6A$ residues. However, 37.3% contain two $m^6A$ peaks, 11.2% contain three peaks, and 5.5% contain four or more peaks. Several genes contain ten or more $m^6A$ peaks, suggesting the existence of multiple $m^6A$ residues along their length. Indeed, of the twenty genes that exhibited the largest number of $m^6A$ peaks, all had 15 or more $m^6A$ peaks along their length (Table 3, infra). Table 2 lists the top 20 mouse brain mRNAs identified by MeRIP-Seq as having the greatest number of $m^6A$ sites along their length.

TABLE 3 mRNAs Containing the Greatest Number of $m^6A$ Peaks.

| Chr | Start | End | RefSeq Accession | Name | # m6A Peaks |
| --- | --- | --- | --- | --- | --- |
| chr18 | 34380637 | 34481844 | NM_007462 | Apc | 24 |
| chr2 | 121115337 | 121136568 | NM_032393 | Mtap1a | 23 |
| chr9 | 15714636 | 16182675 | NM_001080814 | Fat3 | 21 |
| chr11 | 55064111 | 55125759 | NM_001029988 | Fat2 | 19 |
| chr13 | 55311142 | 55419686 | NM_008739 | Nsd1 | 19 |
| chr15 | 72636029 | 72640754 | NR_002864 | Peg13 | 18 |
| chr5 | 14514917 | 14863459 | NM_011995 | Pclo | 17 |
| chr5 | 42178777 | 42235554 | NM_001081422 | Bod11 | 17 |
| chr6 | 22825501 | 23002916 | NM_001081306 | Ptprz1 | 17 |
| chr14 | 93412919 | 94287951 | NM_001081377 | Pcdh9 | 17 |
| chr10 | 79764564 | 79781001 | NM_011789 | Apc2 | 17 |
| chr19 | 9063773 | 9093685 | NM_009643 | Ahnak | 17 |
| chr7 | 17079821 | 17200342 | NM_172739 | Grlf1 | 16 |
| chr1 | 30859186 | 30920101 | NM_001081080 | Phf3 | 16 |
| chr8 | 124122602 | 124175833 | NM_080855 | Zcchc14 | 16 |
| chr11 | 117515602 | 117624753 | NM_198022 | Tnrc6c | 16 |
| chr1 | 20880702 | 20928837 | NM_028829 | Paqr8 | 16 |
| chr4 | 34750358 | 34830197 | NM_013889 | Zfp292 | 16 |
| chr16 | 91648068 | 91663563 | NM_019973 | Son | 16 |
| chr5 | 107926763 | 107941575 | NM_001007574 | A830010M20Rik | 16 |

Additionally, of the genes that contain more than one $m^6A$ peak, 90.1% contain two or more contiguous $m^6A$ peaks, indicating that $m^6A$ sites are frequently clustered in adjacent regions along the transcript. Indeed, 32.8% of $m^6A$ peaks are part of clusters that contain three or more adjacent $m^6A$ peaks, indicating that m⁶A clustering is a common feature in methylated transcripts (FIG. 8A). 68 genes that have long (≥1 kb) stretches of contiguous m⁶A peaks were also identified (Table 4, infra), which likely indicates the presence of multiple m⁶A residues throughout these regions.

TABLE 4

Transcripts with Multiple Adjacent m⁶A Peaks.

| Chr | Start | End | RefSeq Accession | Name | Length Spanned |
|---|---|---|---|---|---|
| chr13 | 98016375 | 98016739 | NM_007930 | Enc1 | 1014 |
| chr9 | 58337925 | 58338199 | NM_176921 | 6030419C18Rik | 1024 |
| chr1 | 193732829 | 193733854 | NM_009579 | Slc30a1 | 1025 |
| chr2 | 160774888 | 160775913 | NM_173368 | Chd6 | 1025 |
| chr3 | 32418578 | 32419603 | NM_144519 | Zfp639 | 1025 |
| chr7 | 95279165 | 95280190 | NM_001081414 | Grm5 | 1025 |
| chr9 | 111294275 | 111295300 | NM_001164659 | Trank1 | 1025 |
| chrX | 61523268 | 61524293 | NM_178740 | Slitrk4 | 1025 |
| chr16 | 96223704 | 96224729 | NM_001103179 | Brwd1 | 1025 |
| chr2 | 79294197 | 79295205 | NM_010894 | Neurod1 | 1030 |
| chr3 | 16104675 | 16105424 | NM_172677 | Ythdf3 | 1049 |
| chr3 | 82196199 | 82197249 | NM_001081230 | Mtap9 | 1050 |
| chr3 | 107990483 | 107991533 | NM_146137 | Amigo1 | 1050 |
| chr9 | 16179392 | 16180442 | NM_001080814 | Fat3 | 1050 |
| chr9 | 101003350 | 101004400 | NM_001100451 | Msl2 | 1050 |
| chr1 | 49074547 | 49075597 | NM_001110148 | Mgat1 | 1050 |
| chr18 | 39645651 | 39646701 | NM_008173 | Nr3c1 | 1050 |
| chr1 | 58959643 | 58960718 | NM_172406 | Trak2 | 1075 |
| chr7 | 51716878 | 51717953 | NM_198250 | Lrrc4b | 1075 |
| chr8 | 124124353 | 124125427 | NM_080855 | Zcchc14 | 1075 |
| chr9 | 20241361 | 20242436 | NM_011753 | Zfp26 | 1075 |
| chr11 | 22735963 | 22737038 | NM_016888 | B3gnt2 | 1075 |
| chr12 | 93046957 | 93048034 | NM_001039089 | Sel11 | 1075 |
| chr9 | 110148798 | 110149894 | NM_013884 | Cspg5 | 1096 |
| chr1 | 136644451 | 136645551 | NM_009307 | Syt2 | 1100 |
| chr8 | 75338622 | 75339722 | NM_010687 | Large | 1100 |
| chr11 | 60883429 | 60884529 | NM_010603 | Kcnj12 | 1100 |
| chr19 | 23239297 | 23240397 | NM_010638 | Klf9 | 1100 |
| chr2 | 28084698 | 28085823 | NM_001038613 | Olfm1 | 1125 |
| chr2 | 28084698 | 28085823 | NM_019498 | Olfm1 | 1125 |
| chr13 | 60862120 | 60863245 | NM_029653 | Dapk1 | 1125 |
| chr11 | 79315458 | 79316529 | NM_019409 | Omg | 1140 |
| chr2 | 125565321 | 125566471 | NM_177608 | Secisbp21 | 1150 |
| chr17 | 5342062 | 5343212 | NM_001085355 | Arid1b | 1150 |
| chr8 | 34496846 | 34498001 | NM_152821 | Purg | 1155 |
| chr2 | 168007289 | 168008464 | NM_009628 | Adnp | 1175 |
| chr6 | 56728743 | 56729918 | NM_145958 | Kbtbd2 | 1175 |
| chr8 | 63149995 | 63151170 | NM_027756 | Mfap31 | 1175 |
| chrX | 163911865 | 163913040 | NM_001033330 | Frmpd4 | 1175 |
| chr11 | 20625687 | 20626862 | NM_181411 | Aftph | 1175 |
| chr3 | 27140122 | 27141322 | NM_178772 | Nceh1 | 1200 |
| chr10 | 34002445 | 34003645 | NM_009433 | Tspyl1 | 1200 |
| chr12 | 112948203 | 112949403 | NM_027404 | Bag5 | 1200 |
| chr17 | 32910441 | 32911641 | NM_172458 | Zfp871 | 1200 |
| chr4 | 68422805 | 68424030 | NM_019967 | Dbc1 | 1225 |
| chr7 | 71035186 | 71036436 | NM_021366 | Klf13 | 1250 |
| chr4 | 49598302 | 49599577 | NM_025944 | 2810432L12Rik | 1275 |
| chr7 | 13395301 | 13396576 | NM_026046 | Zfp329 | 1275 |
| chr6 | 8900268 | 8900307 | NM_008751 | Nxph1 | 1289 |
| chr18 | 37304447 | 37305772 | NM_001003672 | Pcdhac2 | 1325 |
| chr1 | 20926262 | 20927612 | NM_028829 | Paqr8 | 1350 |
| chr2 | 67955794 | 67957144 | NM_020283 | B3galt1 | 1350 |
| chr15 | 100870221 | 100871571 | NM_001077499 | Scn8a | 1350 |
| chr5 | 82223313 | 82224688 | NM_198702 | Lphn3 | 1375 |
| chr9 | 56466831 | 56468206 | NM_181074 | Lingo1 | 1375 |
| chr18 | 46664659 | 46666043 | NM_173423 | Fem1c | 1384 |
| chr2 | 140485333 | 140486733 | NM_001172160 | Flrt3 | 1400 |
| chr12 | 42179629 | 42181029 | NM_010733 | Lrrn3 | 1400 |
| chr4 | 11887956 | 11889380 | NM_001098231 | Pdp1 | 1424 |
| chr2 | 83719391 | 83720816 | NM_175514 | Fam171b | 1425 |
| chr9 | 111174998 | 111176523 | NM_175266 | Epm2aip1 | 1525 |
| chr5 | 58111684 | 58113234 | NM_001122758 | Pcdh7 | 1550 |
| chr10 | 112364133 | 112365733 | NM_001033474 | Atxn7l3b | 1600 |
| chr6 | 77193821 | 77195446 | NM_028880 | Lrrtm1 | 1625 |
| chr15 | 80709571 | 80711271 | NM_144812 | Tnrc6b | 1700 |
| chr2 | 97469495 | 97471220 | NM_178725 | Lrrc4c | 1725 |

TABLE 4-continued

Transcripts with Multiple Adjacent m⁶A Peaks.

| Chr | Start | End | RefSeq Accession | Name | Length Spanned |
|---|---|---|---|---|---|
| chr11 | 117582888 | 117584738 | NM_198022 | Tnrc6c | 1850 |
| chr15 | 72636954 | 72640029 | NR_002864 | Peg13 | 3075 |

Shown in Table 4 are the 68 RNAs in mouse brain that have long (≥1 kb) stretches of contiguous m⁶A peaks. The genomic coordinates for each region of adjacent peaks are given (Chr; Start; End), as well as the RefSeq accession number and gene symbol for the transcript that contains each cluster of peaks. The distance that each set of contiguous peaks spans is also provided (Length Spanned). These sites of multiple contiguous m⁶A peaks are likely to represent regions of highly clustered m⁶A residues.

It was next determined which mRNAs contain m⁶A sites with the highest degree of methylation. To do this, a method of calculating the level of m⁶A enrichment at individual m⁶A peaks was developed, which normalized the number of MeRIP sample reads within each peak to the abundance of the individual transcript in which the peak resides (see Example 1, supra). The genes which contain the most enriched m⁶A peaks are listed in Table 5, infra. In particular, Table 5 shows the top twenty genes which contain m⁶A peaks with the highest levels of enrichment.

TABLE 5

Genes Encoding Transcripts with the Highest Degree of m6A Enrichment.

| Chr | Peak Start | Peak End | RefSeq Accession | Gene Symbol | Enrichment Score |
|---|---|---|---|---|---|
| chr6 | 58856032 | 58856214 | NM_021432 | Nap1l5 | 3.859 |
| chr3 | 30717625 | 30717825 | NM_027016 | Sec62 | 3.693 |
| chr3 | 88566067 | 88566234 | NM_018804 | Syt11 | 3.452 |
| chr6 | 58855850 | 58856032 | NM_021432 | Nap1l5 | 3.327 |
| chr19 | 5801367 | 5801534 | NR_002847 | Malat1 | 3.322 |
| chr12 | 110898950 | 110899150 | NR_028261 | Rian | 3.222 |
| chr10 | 34018834 | 34018993 | NM_030203 | Tspyl4 | 3.162 |
| chr17 | 6138575 | 6138775 | NM_054040 | Tulp4 | 2.984 |
| chr2 | 34631357 | 34631514 | NM_001163434 | Hspa5 | 2.935 |
| chr2 | 102630175 | 102630350 | NM_001077514 | Slc1a2 | 2.933 |
| chr11 | 7072225 | 7072425 | NM_009622 | Adcy1 | 2.865 |
| chr2 | 158211200 | 158211350 | NM_175692 | Snhg11 | 2.788 |
| chr15 | 37326800 | 37327000 | NM_134094 | Ncald | 2.685 |
| chr2 | 102629600 | 102629788 | NM_001077514 | Slc1a2 | 2.672 |
| chr15 | 37327000 | 37327200 | NM_134094 | Ncald | 2.656 |
| chr10 | 80644950 | 80645125 | NM_007907 | Eef2 | 2.451 |
| chr2 | 102629788 | 102629975 | NM_001077514 | Slc1a2 | 2.392 |
| chr11 | 59251613 | 59251750 | NM_144521 | Snap47 | 2.306 |
| chr15 | 74581075 | 74581267 | NM_011838 | Lynx1 | 2.258 |
| chr2 | 158211050 | 158211200 | NM_175692 | Snhg11 | 2.102 |

Importantly, because MeRIP-Seq identifies m⁶A sites at a resolution of 200 nt, there could be multiple individual m⁶A residues within the area covered by each peak. Therefore, the peaks with the highest levels of local m⁶A enrichment may represent a single adenosine residue which exhibits a high degree of methylation, or multiple adjacent m⁶A residues with a lower stoichiometry of methylation. In either case, however, the high levels of methylation observed at these sites likely indicate transcripts that are most influenced by m⁶A-dependent regulatory processes.

Example 8

$m^6A$ is Enriched Near Stop Codons and in 3' UTRs of mRNAs

Figure 5C:
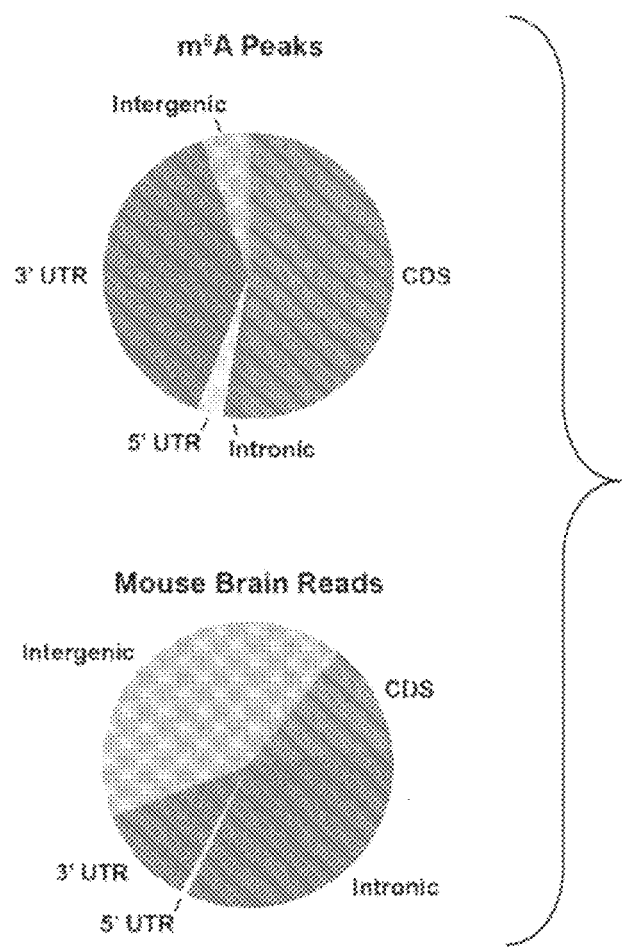

The distribution of $m^6A$ peaks within regions of the transcriptome in the high confidence set was next examined. The majority (94.8%) of $m^6A$ peaks occur within intragenic regions (FIG. 5C). These $m^6A$ peaks are abundant in coding sequences (CDS; 50.9%), and untranslated regions (UTRs; 41.9%), with relatively few in intronic regions (2.0%) (FIG. 5C). Additionally, $m^6A$ peaks are less abundant in the 5' UTR (7.0% of UTR peaks) than in the 3' UTR (93.0% of UTR peaks) (FIG. 5C). This distribution deviates substantially from the distribution of reads in the non-IP sample, indicating the high degree of enrichment of $m^6A$ peaks in the CDS and UTRs (FIG. 5C). Although a low percentage of $m^6A$ peaks was observed in intronic regions, because the samples were not enriched for unspliced pre-mRNAs, it is possible that additional methylated intronic sequences exist.

Figure 5D:
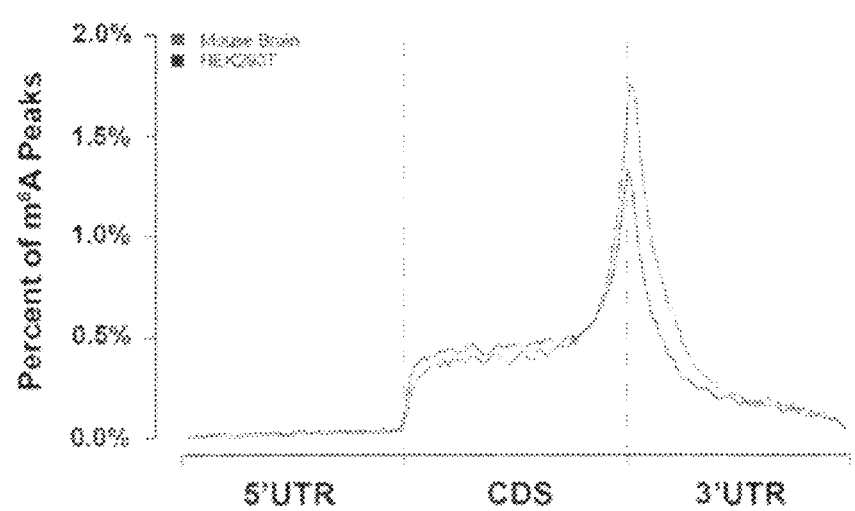

Next, it was sought to determine if $m^6A$ peaks are preferentially found in certain portions of transcripts. To do this, each $m^6A$ peak was assigned to either a 5' UTR, CDS, or 3' UTR category, and assigned it to one of 100 bins a based on its location along the 5' UTR, CDS, or 3' UTR. These data show that $m^6A$ occurs at low levels in the 5' UTR and the 5' end of the CDS. In the CDS, the percentage of $m^6A$ peaks increases steadily along transcript length and is on average 5-6 fold higher at the end of the CDS than at the beginning (FIG. 5D). In the 3' UTR, the peaks are enriched near the stop codon and decrease in abundance along the length of the 3' UTR. Indeed, 61% of $m^6A$ peaks are in the first quarter of the 3' UTR and a quarter of all $m^6A$ peaks across the entire transcriptome are found within the first 26% of the 3' UTR (FIG. 5D). Mapping the number of $m^6A$ peaks 1 kb up and downstream of CDS end sites further demonstrated the high levels of methylation in the vicinity of the stop codon (FIG. 9A, 9B). Collectively, these data indicate that $m^6A$ peaks are highly clustered in the vicinity of the stop codon in mRNAs.

Example 9

$m^6A$ Occurs in Highly Conserved Regions within Unique Sequence Motifs

Figure 6A:
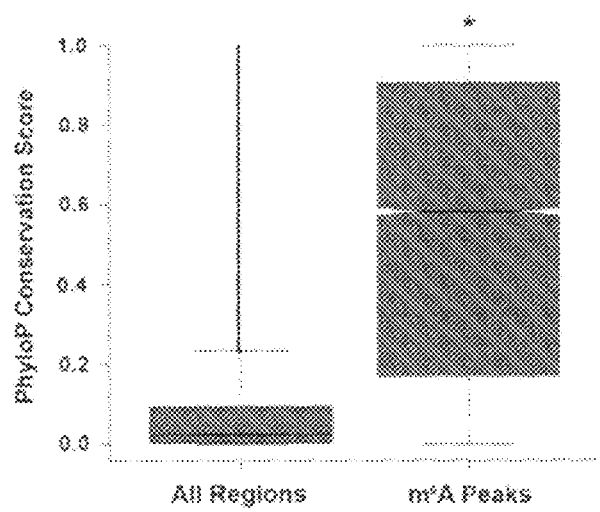

Next, it was asked whether $m^6A$ sites are conserved across species. PhyloP scores were compared across 30 vertebrates (Pollard et al., "Detection of Nonneutral Substitution Rates on Mammalian Phylogenies," *Genome Res.* 20:110-121 (2010), which is hereby incorporated by reference in its entirety) of $m^6A$ peak regions to those of random regions of the same size in gene exons. The distribution of conservation scores of the $m^6A$ peaks was significantly different from that of the random regions ($p \leq 2.2 \times 10^{-16}$, Kolmogorov-Smirnov (K-S) test, FIG. 6A) and $m^6A$ peaks' median conservation score (0.578) was much higher than that of the random regions (0.023). The fact that $m^6A$ frequently occurs in evolutionarily conserved sequences indicates that $m^6A$-containing regions are maintained through selection pressure.

Because the tools for transcriptome-wide localization of $m^6A$ sites have until now been unavailable, only a few studies to date have examined the sequence contexts of $m^6A$ formation (Pollard et al., "Detection of Nonneutral Substitution Rates on Mammalian Phylogenies," *Genome Res.* 20:110-121 (2010); Dimock et al., "Sequence Specificity of Internal Methylation in B77 Avian Sarcoma Virus RNA Subunits," *Biochemistry* 16:471-478 (1977); Wei et al., "5'-Terminal and Internal Methylated Nucleotide Sequences in HeLa Cell mRNA," *Biochemistry* 15:397-401 (1976), each of which is hereby incorporated by reference in its entirety). Using methods such as RNase T1 fingerprinting of radiolabeled RNA followed by separation by thin-layer chromatography, these studies reported that $m^6A$ exists within two unique sequence contexts: GAC and AAC (underlined adenosines indicate $m^6A$). Subsequently, an extended $m^6A$ consensus sequence was identified: PuPu ACX (Pu=purine; X=A, C, or U). However, since the methods used in these studies are not practical for use in a high-throughput manner, it is unclear whether these motifs are relevant to the transcriptome-wide $m^6A$ sites identified by MeRIP-Seq.

Therefore, the sequence motifs that are enriched within $m^6A$ peaks were sought to be identified. To do this, FIRE, a sensitive and unbiased tool for discovering RNA regulatory elements (Elemento et al., "A Universal Framework for Regulatory Element Discovery Across all Genomes and Data Types," *Mol. Cell* 28:337-350 (2007), which is hereby incorporated by reference in its entirety) was used. Remarkably, FIRE independently identified the GAC and AAC motif, G[AG]ACU, and related variants ([AC]GAC[GU], GGAC, [AU][CG]G[AG]AC, and UGAC) as being highly enriched in $m^6A$ peaks (FIG. 6B). For example, the G[AG] ACU motif occurs in 42% of all $m^6A$ mRNA peaks and in a much lower fraction (21%) of non-$m^6A$ control peaks from the same mRNAs ($p<1.0 \times 10^{-124}$, chi-square test). Altogether, it was found that >90% of all $m^6A$ peaks contain at least one of the motifs identified by FIRE.

Figure 6D:
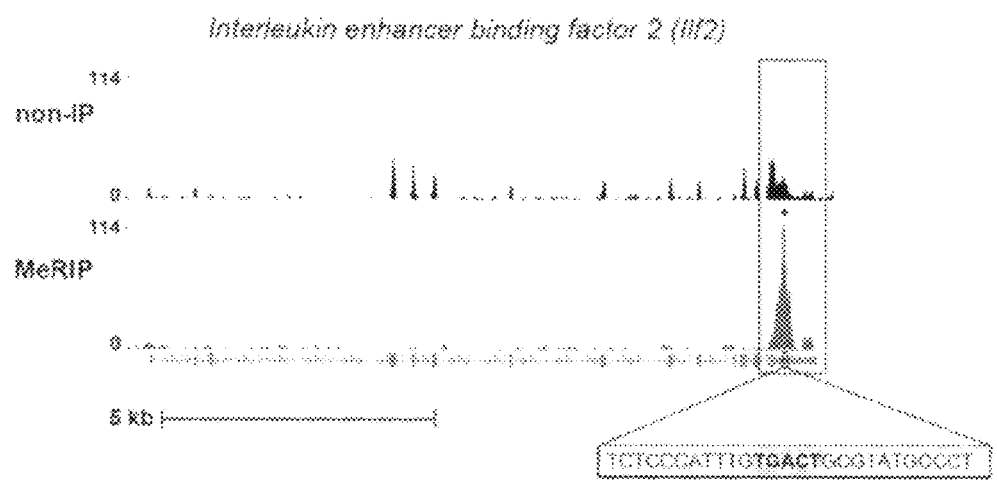

Next, the position of the motifs within $m^6A$ peaks was examined. Nearly 30% of $m^6A$ peaks have only one motif (FIG. 8B), indicating that these peaks are likely to contain only a single methylated residue. Motifs are also preferentially found in the center of $m^6A$ peaks (FIG. 6C, 6D), indicating that these peaks derive from a centrally located methylated adenosine residue. Notably, other RNA regulatory elements, such as AU-rich elements, poly(A) signals, or binding sites for known RNA-binding proteins, were not identified by FIRE, indicating that $m^6A$ is unlikely to primarily function by modifying these known regulatory elements.

Example 10

Relationship Between $m^6A$ Sites and Polyadenylation Signals in 3' UTRs

FIRE did not identify an enrichment of poly(A) signals (PASs), which are involved in 3' UTR end processing, in $m^6A$ peaks. However, PASs exhibit considerable sequence heterogeneity beyond the canonical AAUAAA consensus (Tian et al., "A Large-Scale Analysis of mRNA Polyadenylation of Human and Mouse Genes," *Nucleic Acids Res.* 33:201-212 (2005), which is hereby incorporated by reference in its entirety). This sequence heterogeneity might allow these PASs to evade detection by FIRE, despite being enriched in $m^6A$ peaks. Therefore, further investigation was sought to determine whether $m^6A$ peaks within 3' UTRs are enriched at PASs. A high-confidence list was obtained (Brockman et al., "PACdb: PolyA Cleavage Site and 3'-UTR Database," *Bioinformatics* 21:3691-3693 (2005), which is hereby incorporated by reference in its entirety) of poly(A) cleavage sites (the site downstream of a PAS where the mRNA is actually cleaved and polyadenylated) for the mRNAs that contain $m^6A$ peaks within their 3' UTRs. Next, it was examined whether $m^6A$ peaks were enriched near these sites by determining the number of 3' UTR $m^6A$ peaks that fell within 50 nt upstream of each cleavage site. Since a PAS is located approximately 10-30 nt upstream of an actual mRNA cleavage site (see Proudfoot, "Poly(A) Signals," *Cell* 64:671-674 (1991), which is hereby incorporated by reference in its entirety), these 50 nt-long regions are expected to contain the PAS. Of the 6,288 $m^6A$ peaks found within 3' UTRs, 1,042 (16.6%) overlapped with the 50 nt-long regions upstream of poly(A) cleavage sites, compared to 1,070 (17.0%) control peaks, which were generated from random nonoverlapping regions of the same 3' UTRs. Thus, these data demonstrate that $m^6A$ do not have a significant association with known PASs (p=0.39; chi-square test).

Example 11

$m^6A$ is not Enriched at Splice Junctions

Prior studies that used nonspecific methylation inhibitors to explore possible functions for $m^6A$ revealed impaired splicing in a small number of RNAs (Carroll et al., "N6-Methyladenosine Residues in an Intron-Specific Region of Prolactin Pre-mRNA," *Mol. Cell Biol.* 10:4456-4465 (1990); Stoltzfus et al., "Accumulation of Spliced Avian Retrovirus mRNA is Inhibited in S-Adenosylmethionine-Depleted Chicken Embryo Fibroblasts," *J. Virol.* 42:918-931 (1982), each of which is hereby incorporated by reference in its entirety). Therefore, it was asked whether the localization of $m^6A$ peaks is compatible with a role for influencing the binding of splicing factors. However, only 80 splice junctions were found in regions contiguous with $m^6A$ peaks, significantly less than the overlap seen with a set of randomly-generated peaks (9,531; p=0.0; chi-square test). Thus, unlike CLIP-Seq tag clusters from RNA-binding proteins that influence splicing (Licatalosi et al., "HITS-CLIP Yields Genome-Wide Insights into Brain Alternative RNA Processing," *Nature* 456:464-469 (2008), which is hereby incorporated by reference in its entirety), $m^6A$ peaks did not significantly coincide with exon-exon junctions, indicating that $m^6A$ is unlikely to primarily function to directly influence the binding of splicing factors.

Example 12

Relationship Between $m^6A$ and MicroRNA Binding Sites within 3' UTRs

Figure 6E:
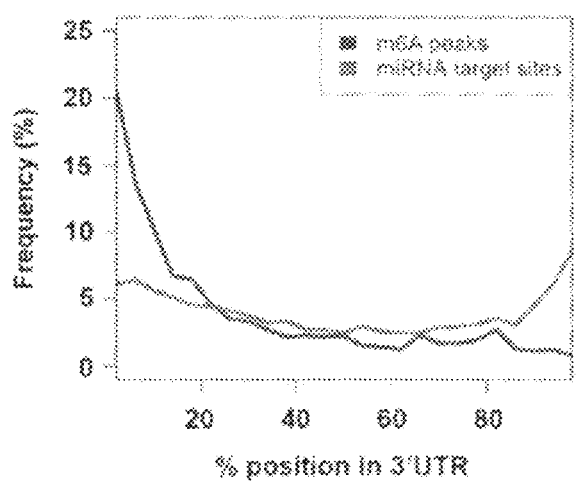

The strong enrichment of $m^6A$ peaks in 3' UTRs prompted the investigation of whether $m^6A$ peaks are found near microRNA (miRNA) binding sites, which are also frequently observed within 3' UTRs. It was found that 67% of 3' UTRs that contain $m^6A$ peaks also contain at least one TargetScan-predicted miRNA binding site. Since ~30% of genes have miRNA binding sites in their 3' UTRs (Lewis et al., "Conserved Seed Pairing, Often Flanked by Adenosines, Indicates that Thousands of Human Genes are MicroRNA Targets," *Cell* 120:15-20 (2005), which is hereby incorporated by reference in its entirety), this is a significantly greater association than what would be expected by chance alone. Intriguingly, it was also found that in 3' UTRs with both $m^6A$ peaks and miRNA binding sites, the $m^6A$ peaks precede miRNA binding sites 62% of the time. Moreover, it was found that the overall distribution of $m^6A$ peaks and miRNA binding sites within 3' UTRs are anti-correlated; while $m^6A$ peaks are most abundant near the stop codon and generally decrease in frequency along 3' UTR length, miRNA target sites are more enriched near the 3' end of 3' UTRs (FIG. 6E). The reason for this inverse localization pattern is unknown, although it could indicate that a certain spatial separation is necessary for $m^6A$ to influence the function of a downstream bound miRNA or vice versa.

Figure 6F:
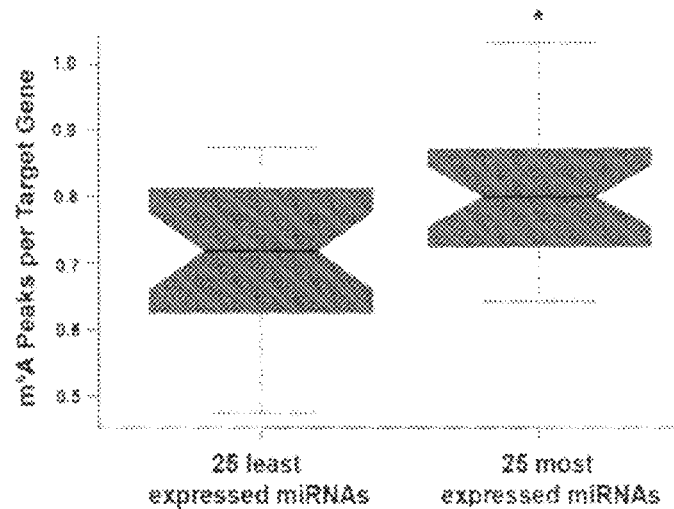

Next, it was sought to determine whether miRNA-targeted transcripts in the brain are more likely to contain $m^6A$. To test this, TargetScan was used to identify the target transcripts of the 25 most highly expressed and 25 least highly expressed miRNAs within the brain. Intriguingly, it was observed that the most highly expressed miRNAs have a significantly greater percentage of target transcripts that contain $m^6A$ (p<0.05, Wilcoxon test; FIG. 6F). These data indicate that miRNA levels may control methylation of their target transcripts.

Example 13

Prominent Features of $m^6A$ Distribution are Conserved in the Human Transcriptome Next it was asked whether the enrichment of $m^6A$ in the 3' UTR is also observed in other species. Therefore, $m^6A$ was profiled in HEK293T cells, a human cell line with high levels of adenosine methylation (FIG. 3B). A high-confidence list of $m^6A$ peaks was generated using three MeRIP-Seq biological replicates and confirmed by both $m^6A$ antibodies. It was found that the distribution of $m^6A$ peaks in HEK293T cells closely mirrored the distribution in mouse brain, with 31% and 53% of $m^6A$ peaks falling within the 3' UTR and the CDS, respectively (FIG. 5D, FIG. 9D). As with the pattern of $m^6A$ distribution in the mouse brain transcriptome, HEK293T $m^6A$ peaks were predominantly localized near stop codons (FIG. 5D and FIG. 9C).

Figure 5E:
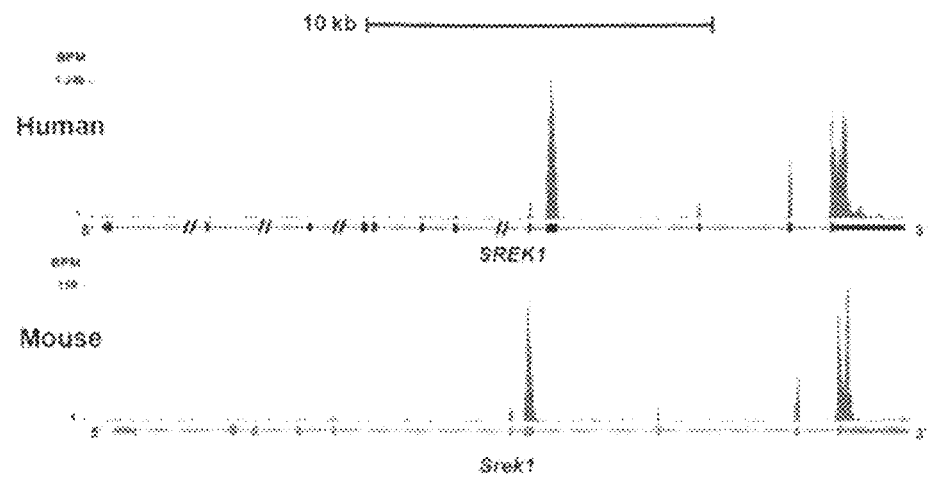

In total, 18,756 peaks were identified in RNAs encoded by 5,768 genes in HEK293T cells. Additionally, transcripts were found from 2,145 and 3,259 genes and were methylated only in the mouse brain and HEK293T datasets, respectively, and transcripts from 2,509 genes were methylated in both datasets. Interestingly, among the transcripts methylated in both tissues, $m^6A$ peaks were often localized to the same distinct regions of both orthologs (FIG. 5E). Collectively, these data indicated that $m^6A$ peaks are enriched near the stop codon in human transcripts and that many sites of methylation are conserved in mouse and human transcripts.

Discussion of Examples 1-13

Unlike DNA, which undergoes cytosine methylation and hydroxymethylation, dynamic internal modifications of mRNA other than RNA editing have not been established. Recent evidence that the obesity risk gene, FTO, is a physiologic $m^6A$ demethylase suggests that $m^6A$ has central roles in cellular function. Here, MeRIP-Seq (the method of the present invention) is used to provide the first transcriptome-wide characterization of $m^6A$. It is shown that $m^6A$ is a reversible and widespread modification which is primarily located in evolutionarily conserved regions and is particularly enriched near the stop codon. It was found that many features of $m^6A$ localization are conserved between the human and mouse transcriptomes, and a previously unidentified link between $m^6A$ and miRNA signaling was uncovered. Collectively, these studies reveal that $m^6A$ is a widespread and dynamically regulated base modification in mRNA, and they identify mRNAs which are most likely to be influenced by signaling pathways that influence $m^6A$ levels.

One of the most striking features of $m^6A$ localization is its prevalence within 3' UTRs. The 3' UTR is an important region for RNA regulation, as it can influence RNA stability, subcellular localization, and translation regulation. Several of these events are regulated by RNA binding proteins (RBPs) that bind to cis-acting structural motifs or consensus sequences within the 3' UTR and act to coordinate RNA processing. Conceivably, $m^6A$ may influence the affinity of specific RBPs for their target mRNAs, analogous to the recruitment of methyl-CpG binding protein 2 (MeCP2) to methylated cytosine residues in DNA (Lewis et al., "Purification, Sequence, and Cellular Localization of a Novel Chromosomal Protein that Binds to Methylated DNA," Cell 69:905-914 (1992), which is hereby incorporated by reference in its entirety). Given the abundance of $m^6A$ throughout the transcriptome and its widespread localization, such a role for $m^6A$ would be likely to have important consequences for the regulation of numerous mRNAs.

The profiling of $m^6A$ in HEK293T cells in the present invention revealed thousands of transcripts that are also methylated in the mouse brain. In many cases, the patterns of $m^6A$ localization within these transcripts are nearly identical, suggesting that some RNAs possess highly conserved methylation profiles. However, many transcripts were also uncovered that exhibit distinct cell type-specific methylation patterns, demonstrating that $m^6A$ is also capable of being differentially regulated within unique cellular environments.

The finding of the present invention that a large proportion of 3' UTRs that contain $m^6A$ peaks also contain miRNA binding sites is highly suggestive of an association between $m^6A$ and miRNA function. Additionally, this analysis also indicated an inverse localization of $m^6A$ peaks and miRNA binding sites within 3' UTRs, with $m^6A$ sites typically preceding, but not overlapping, the miRNA sites in the 3' UTRs. Although miRNAs can inhibit their target mRNAs by promoting either transcript degradation or translational repression (Guo et al., "Mammalian MicroRNAs Predominantly Act to Decrease Target mRNA Levels," Nature 466: 835-840 (2010); Hendrickson et al., "Concordant Regulation of Translation and mRNA Abundance for Hundreds of Targets of a Human MicroRNA," PLoS Biol 7(11):e1000238 (2009), each of which is hereby incorporated by reference in its entirety), the factors that determine which fate predominates are not well understood. Conceivably, the proximity of $m^6A$ to a miRNA binding site could influence the mechanism of miRNA-mediated transcript inhibition. Additionally, it is possible that miRNA binding influences $m^6A$ levels within 3' UTRs. Indeed, the finding of the present invention that abundant miRNAs are more significantly enriched in $m^6A$ peaks than weakly expressed miRNAs raises the possibility that miRNAs regulate methylation status.

A surprising result of these studies is the finding that $m^6A$ is highly enriched near stop codons. This recurrent localization within transcripts indicates that adenosine methylation in the vicinity of the stop codon may be of functional importance. Interestingly, the consensus for adenosine methylation is relatively short, and sequences that match the consensus are found throughout the transcriptome. However, despite the frequency of $m^6A$ consensus sites, methylation occurs primarily near stop codons.

The finding that FTO demethylates $m^6A$ suggests that misregulation of pathways controlled by adenosine methylation ultimately affect physiologic processes in humans. Although $m^6A$ is found in many classes of RNA, it is intriguing to speculate that FTO mutations mediate their effects by affected $m^6A$ in mRNA. Indeed, the present finding that FTO can demethylate diverse mRNAs is consistent with this model.

The present invention demonstrates that $m^6A$ is a widespread modification found in a large fraction of cellular mRNA. The pervasive nature of this modification indicates that adenosine methylation has important roles in RNA biology. Much how cytosine methylation and hydroxymethylation in DNA are important epigenetic regulators of the genome, the present data demonstrate that adenosine methylation in RNA is a reversible modification that is likely to influence a wide variety of biological pathways and physiological processes.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of characterizing a modified base status of a transcriptome, said method comprising:
    contacting a transcriptome comprising (i) coding and non-coding RNA transcripts and (ii) one or more modified bases, with an antibody specific to the one or more modified bases under conditions effective to bind the antibody to the one or more modified bases, wherein the one or more modified bases is $N^6$-methyladenosine ($m^6A$);
    isolating, from the transcriptome, a pool of RNA transcripts to which the antibody binds; and
    identifying isolated coding and non-coding RNA transcripts that are present in a higher abundance in the isolated pool relative to the transcriptome, wherein each of said isolated RNA transcripts that are present in a higher abundance in the isolated pool together characterize the modified base status of the transcriptome.

2. The method according to claim 1, wherein the antibody is coupled to a magnetic bead or a paramagnetic bead.

3. The method according to claim 1, wherein said isolating is carried out by immunoprecipitation.

4. The method according to claim 1 further comprising:
    fragmenting RNA transcripts of the transcriptome before said contacting to form RNA transcript fragments, wherein the isolated RNA transcripts are RNA transcript fragments.

5. The method according to claim 4, wherein said RNA transcript fragments are about 100 nucleotides in length.

6. The method according to claim 4 further comprising:
    sequencing the RNA transcript fragments and isolated RNA transcript fragments.

7. The method according to claim 4 further comprising:
    measuring the abundance of both the RNA transcript fragments of the transcriptome and the isolated RNA transcript fragments.

8. The method according to claim 4, wherein said identifying comprises comparing the abundance of an RNA transcript fragment in the isolated pool to the abundance of that RNA transcript fragment in the transcriptome prior to said isolating.

9. The method according to claim 1 further comprising:
obtaining a transcriptome from a cell or a tissue.

10. The method according to claim 9, wherein said obtaining is from a single cell type.

11. The method according to claim 9, wherein said obtaining is from a single tissue type.

12. The method according to claim 9, wherein said obtaining is from a diseased tissue.

13. The method according to claim 9, wherein said obtaining is from a non-diseased tissue.

14. The method according to claim 9, wherein said obtaining is from a diseased cell.

15. The method according to claim 9, wherein said obtaining is from a non-diseased cell.

16. The method according to claim 1 further comprising:
comparing the modified base status of a transcriptome from a first cell type or tissue type to the modified base status of a transcriptome from a second cell type or tissue type.

17. The method according to claim 16, wherein the first cell type or tissue type is from a non-diseased cell or tissue and the second cell type or tissue type is from a diseased cell or tissue.

18. The method according to claim 1, further comprising:
crosslinking the antibody specific to the one or more modified bases to the one or more modified bases.

19. The method according to claim 18, wherein the crosslinking is UV-crosslinking.

\* \* \* \* \*

SEQUENCE LISTING

<160> NUMBER OF SEQ ID NOS: 26

<210> SEQ ID NO 1
<211> LENGTH: 25
<212> TYPE: DNA
<213> ORGANISM: artificial
<220> FEATURE:
<223> OTHER INFORMATION: Oligonucleotide

<400> SEQUENCE: 1
agtcgttcat ctagttgcgg tgtac                                      25

<210> SEQ ID NO 2
<211> LENGTH: 35
<212> TYPE: DNA
<213> ORGANISM: artificial
<220> FEATURE:
<223> OTHER INFORMATION: Primer

<400> SEQUENCE: 2
taatacgact cactataggg tgtcaccaac tggga                    35

<210> SEQ ID NO 3
<211> LENGTH: 20
<212> TYPE: DNA
<213> ORGANISM: artificial
<220> FEATURE:
<223> OTHER INFORMATION: Primer

<400> SEQUENCE: 3
accctcatag atgggcacag                                    20

<210> SEQ ID NO 4
<211> LENGTH: 20
<212> TYPE: DNA
<213> ORGANISM: artificial
<220> FEATURE:
<223> OTHER INFORMATION: Primer

<400> SEQUENCE: 4
tgtcaccaac tgggacgata                                    20

<210> SEQ ID NO 5
<211> LENGTH: 20
<212> TYPE: DNA
<213> ORGANISM: artificial
<220> FEATURE:
<223> OTHER INFORMATION: Primer

<400> SEQUENCE: 5
accctcatag atgggcacag                                    20

<210> SEQ ID NO 6
<211> LENGTH: 20
<212> TYPE: DNA
<213> ORGANISM: artificial
<220> FEATURE:
<223> OTHER INFORMATION: Primer

<400> SEQUENCE: 6
tgtcaccaac tgggacgata                                    20

<210> SEQ ID NO 7
<211> LENGTH: 20
<212> TYPE: DNA
<213> ORGANISM: artificial
<220> FEATURE:
<223> OTHER INFORMATION: Primer

<400> SEQUENCE: 7
accctcatag atgggcacag                                    20

<210> SEQ ID NO 8
<211> LENGTH: 24
<212> TYPE: DNA
<213> ORGANISM: artificial
<220> FEATURE:
<223> OTHER INFORMATION: Primer

<400> SEQUENCE: 8
tgtaggcggt gctacagagt tctt                               24

<210> SEQ ID NO 9
<211> LENGTH: 24
<212> TYPE: DNA

<213> ORGANISM: artificial
<220> FEATURE:
<223> OTHER INFORMATION: Primer

<400> SEQUENCE: 9
tttctgcgcg taatctgctg cttg                                          24

<210> SEQ ID NO 10
<211> LENGTH: 24
<212> TYPE: DNA
<213> ORGANISM: artificial
<220> FEATURE:
<223> OTHER INFORMATION: Primer

<400> SEQUENCE: 10
ggccttttgg ctaagatcaa gtgt                                          24

<210> SEQ ID NO 11
<211> LENGTH: 24
<212> TYPE: DNA
<213> ORGANISM: artificial
<220> FEATURE:
<223> OTHER INFORMATION: Primer

<400> SEQUENCE: 11
ggacggagca agctcctatt ccaa                                          24

<210> SEQ ID NO 12
<211> LENGTH: 20
<212> TYPE: DNA
<213> ORGANISM: artificial
<220> FEATURE:
<223> OTHER INFORMATION: Primer

<400> SEQUENCE: 12
acctggagcc cagtcagccc                                               20

<210> SEQ ID NO 13
<211> LENGTH: 20
<212> TYPE: DNA
<213> ORGANISM: artificial
<220> FEATURE:
<223> OTHER INFORMATION: Primer

<400> SEQUENCE: 13
cacagacggc gaccacgacg                                               20

<210> SEQ ID NO 14
<211> LENGTH: 20
<212> TYPE: DNA
<213> ORGANISM: artificial
<220> FEATURE:
<223> OTHER INFORMATION: Primer

<400> SEQUENCE: 14
ctgcggaggc acgagctact                                               20

<210> SEQ ID NO 15
<211> LENGTH: 20
<212> TYPE: DNA
<213> ORGANISM: artificial
<220> FEATURE:
<223> OTHER INFORMATION: Primer

<400> SEQUENCE: 15
ttccgcggca cgtacaggtc                                               20

```
<210> SEQ ID NO 16
<211> LENGTH: 20
<212> TYPE: DNA
<213> ORGANISM: artificial
<220> FEATURE:
<223> OTHER INFORMATION: Primer

<400> SEQUENCE: 16
tgtcaccaac tgggacgata                                                 20

<210> SEQ ID NO 17
<211> LENGTH: 20
<212> TYPE: DNA
<213> ORGANISM: artificial
<220> FEATURE:
<223> OTHER INFORMATION: Primer

<400> SEQUENCE: 17
accctcatag atgggcacag                                                 20

<210> SEQ ID NO 18
<211> LENGTH: 21
<212> TYPE: DNA
<213> ORGANISM: artificial
<220> FEATURE:
<223> OTHER INFORMATION: Primer

<400> SEQUENCE: 18
cctcccatcc cggtctccac c                                               21

<210> SEQ ID NO 19
<211> LENGTH: 20
<212> TYPE: DNA
<213> ORGANISM: artificial
<220> FEATURE:
<223> OTHER INFORMATION: Primer

<400> SEQUENCE: 19
ggctgcccat cttcaggggt                                                 20

<210> SEQ ID NO 20
<211> LENGTH: 20
<212> TYPE: DNA
<213> ORGANISM: artificial
<220> FEATURE:
<223> OTHER INFORMATION: Primer

<400> SEQUENCE: 20
gcctcagtgt gacggtggcc                                                 20

<210> SEQ ID NO 21
<211> LENGTH: 20
<212> TYPE: DNA
<213> ORGANISM: artificial
<220> FEATURE:
<223> OTHER INFORMATION: Primer

<400> SEQUENCE: 21
agcttgccgt caccgacgtg                                                 20

<210> SEQ ID NO 22
<211> LENGTH: 20
<212> TYPE: DNA
<213> ORGANISM: artificial
<220> FEATURE:
```

```
<223> OTHER INFORMATION: Primer

<400> SEQUENCE: 22
tgtgtggttt ggctgggcga                                              20

<210> SEQ ID NO 23
<211> LENGTH: 20
<212> TYPE: DNA
<213> ORGANISM: artificial
<220> FEATURE:
<223> OTHER INFORMATION: Primer

<400> SEQUENCE: 23
tggagatgga gcctcggggc                                              20

<210> SEQ ID NO 24
<211> LENGTH: 20
<212> TYPE: DNA
<213> ORGANISM: artificial
<220> FEATURE:
<223> OTHER INFORMATION: Primer

<400> SEQUENCE: 24
tgctcaggag ggtggccctt                                              20

<210> SEQ ID NO 25
<211> LENGTH: 20
<212> TYPE: DNA
<213> ORGANISM: artificial
<220> FEATURE:
<223> OTHER INFORMATION: Primer

<400> SEQUENCE: 25
cggggtttgc gcgtttccag                                              20

<210> SEQ ID NO 26
<211> LENGTH: 27
<212> TYPE: DNA
<213> ORGANISM: artificial
<220> FEATURE:
<223> OTHER INFORMATION: m6A motif

<400> SEQUENCE: 26
tctcccattt gtgactgcgt atgccct                                      27
```